United States Patent
Lin et al.

(10) Patent No.: US 9,527,838 B2
(45) Date of Patent: Dec. 27, 2016

(54) 2-PYRIDINECARBOXAMIDE DERIVATIVES, COMPOSITIONS CONTAINING SUCH COMPOUNDS, AND METHODS OF TREATMENT

(71) Applicant: Merck Sharp & Dohme Corp., Rahway, NJ (US)

(72) Inventors: Songnian Lin, Holmdel, NJ (US); Emma R. Parmee, Doylestown, PA (US); Jiayi Xu, Marlboro, NJ (US)

(73) Assignee: Merck Sharp & Dohme Corp., Rahwah, NJ (US)

( * ) Notice: Subject to any disclaimer, the term of this patent is extended or adjusted under 35 U.S.C. 154(b) by 0 days.

(21) Appl. No.: 14/652,944

(22) PCT Filed: Dec. 12, 2013

(86) PCT No.: PCT/US2013/074584
§ 371 (c)(1),
(2) Date: Jun. 17, 2015

(87) PCT Pub. No.: WO2014/099584
PCT Pub. Date: Jun. 26, 2014

(65) Prior Publication Data
US 2015/0336946 A1    Nov. 26, 2015

Related U.S. Application Data

(60) Provisional application No. 61/738,146, filed on Dec. 17, 2012.

(51) Int. Cl.
| | | |
|---|---|---|
| C07D 417/14 | (2006.01) | |
| A61K 31/675 | (2006.01) | |
| A61K 31/4439 | (2006.01) | |
| C07D 417/12 | (2006.01) | |
| A61K 31/444 | (2006.01) | |
| C07F 9/6558 | (2006.01) | |
| C07D 401/12 | (2006.01) | |

(52) U.S. Cl.
CPC ........... C07D 417/12 (2013.01); A61K 31/444 (2013.01); A61K 31/4439 (2013.01); A61K 31/675 (2013.01); C07D 401/12 (2013.01); C07D 417/14 (2013.01); C07F 9/65583 (2013.01)

(58) Field of Classification Search
CPC . C07D 417/14; C07D 417/12; A61K 31/4439; A61K 31/444; A61K 31/675; C07F 9/65583
USPC ..................................................... 546/268.1
See application file for complete search history.

(56) References Cited

U.S. PATENT DOCUMENTS

| | | | | |
|---|---|---|---|---|
| 7,629,362 B2 * | 12/2009 | Mitsuya | ............... | C07D 471/04 514/342 |
| 8,344,003 B2 * | 1/2013 | Mitsuya | ............... | C07D 471/04 514/342 |
| 8,765,789 B2 * | 7/2014 | Mitsuya | ............... | C07D 471/04 514/333 |
| 2006/0258701 A1 | 11/2006 | Mitsuya et al. | | |
| 2008/0090799 A1 | 4/2008 | Hashimoto et al. | | |
| 2010/0041660 A1 * | 2/2010 | Mitsuya | ............... | C07D 471/04 514/242 |
| 2010/0190980 A1 * | 7/2010 | Umemiya | ............ | C07D 401/14 544/238 |
| 2010/0261699 A1 | 10/2010 | Hasimoto et al. | | |
| 2013/0085156 A1 * | 4/2013 | Mitsuya | ............... | C07D 471/04 514/303 |

FOREIGN PATENT DOCUMENTS

| | | |
|---|---|---|
| EP | 2157090 A1 | 2/2010 |
| WO | 2014/099578 A1 | 6/2014 |

OTHER PUBLICATIONS

Matschinsky; Handbook of Experimental Pharmacology 2011, 203, 357-401.*
Otaegui; FASEB Journal 2003, 17, 2097-2099.*
Kumari, et al., "Comparative Docking Assessment of Glucokinase Interactions wit hits Allosteric Activators", Current Chemical Genomics, vol. 2, pp. 76-89 (2002).
International Search Report for PCT/US2013/074584 mailed Apr. 14, 2014.
Written Opinion for PCT/US2013/074584 mailed Apr. 14, 2014.
Mitsuya et al., Discovery of novel 3,6-disubstituted 2-pyridinecarboxamide derivatives as GK activators, Biorganic & Medicinal Chemistry Letters, 2009, pp. 2718-2721, 19.

* cited by examiner

*Primary Examiner* — Noble Jarrell
*Assistant Examiner* — Daniel Carcanague
(74) *Attorney, Agent, or Firm* — Anna L. Cocuzzo; Catherine D. Fitch

(57) ABSTRACT

Novel pyridine-2-carboxamide derivatives of formula I and pharmaceutically acceptable salts thereof are disclosed as useful for treating or preventing type 2 diabetes and similar conditions. The compounds are effective as glucokinase activating agents. Pharmaceutical compositions and methods of treatment are also included. The present invention relates to novel pyridine-2-carboxamide derivatives and salts thereof which are effective as glucokinase activating agents. Moreover, it relates to compositions containing such compounds, and methods of treatment.

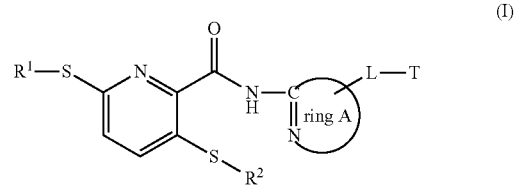

(I)

13 Claims, No Drawings

2-PYRIDINECARBOXAMIDE DERIVATIVES, COMPOSITIONS CONTAINING SUCH COMPOUNDS, AND METHODS OF TREATMENT

FIELD OF THE INVENTION

The present invention relates to novel pyridine-2-carboxamide derivatives and salts thereof which are effective as glucokinase activating agents. Moreover, it relates to compositions containing such compounds, and methods of treatment.

CROSS-REFERENCE TO RELATED APPLICATIONS

This application is a U.S. National Phase application under 35 U.S.C. §371 of PCT/US2013/074584, filed Dec. 12, 2013, which published as WO 2014/099584 on Jun. 26, 2014, which claims priority from U.S. provisional application 61/738,146 filed Dec. 17, 2012.

BACKGROUND OF THE INVENTION

The present invention relates to glucokinase activators. In particular, the present invention is directed to compounds useful for the treatment of diabetes, especially type 2 diabetes, as well as related diseases and conditions such as obesity and metabolic syndrome.

Glucokinase (GK)(ATP: D-hexose 6-phosphotransferase, EC 2.7.1.1) is one of 4 types of hexokinase (hexokinase IV) in mammals. Hexokinase is an enzyme that acts in the first stage of the glycolytic pathway catalyzing the reaction from glucose to glucose 6-phosphate. Glucokinase is localized mainly in the liver and the beta cells of the pancreas where it controls the rate-determining step of glucose metabolism. Notably, in 3 types of hexokinase (I, II, and III) other than glucokinase, the enzyme activities are saturated at a 1 mM or lower concentration of glucose, whereas the Km of glucokinase for glucose is 8 mM, which value is proximate to the physiological blood sugar level. Therefore, the intracellular glucose metabolism is accelerated through glucokinase in response to the change of blood sugar level from normal (5 mM) to postprandial elevation (10-15 mM).

Results in recombinant mice expressing glucokinase have demonstrated that in fact glucokinase plays an important role in the generalized homeostasis of glucose. Though mice in which the glucokinase gene has been destroyed result in death shortly after birth (Grupe A, et al., "Transgenic knockouts reveal a critical requirement for pancreatic beta cell glucokinase in maintaining glucose homeostasis", Cell, 83, 1995, P. 69-78.), the blood sugar level is decreased in normal and diabetic mice where glucokinase is generated in excess (Ferre T, et al., "Correction of diabetic alterations by glucokinase", Proceedings of the National Academy of Sciences of the U.S.A., 93, 1996, P. 7225-7230). With increase of the glucose concentration, the reactions of the pancreatic beta cells and hepatocytes move toward decreasing the blood sugar level.

This means that glucokinase works as a glucose sensor in humans and plays an important role in glucose homeostasis. As such, it is believed that for a large number of type II diabetic patients, it may be possible to regulate blood sugar level utilizing a glucokinase sensor system.

The disclosed glucokinase-activating substances are expected to accelerate insulin secretion in the pancreatic beta cells, and accelerate sugar uptake and inhibit sugar release in liver. Thus, they are considered useful as therapeutic agents in the treatment of type II diabetes.

It has furthermore been elucidated that the occurrence of glucokinase of the pancreatic beta cell type is localized in the brain of rats, particularly in the feeding center (ventromedial hypothalamus; VMH). About 20% of the neurocytes in VMH, called the glucose responsive neuron, are believed to play an important role in control of body weight. Feeding of rats is decreased when glucose is administered into the brain, while inhibition of the glucose metabolism by intracerebral administration of a glucose analog, glucosamine, causes hyperphagia. From electrophysiological experiments, it has been recognized that the glucose responsive neuron is activated in response to the physiological change of glucose concentration (5-20 mM), but its activity is inhibited by inhibiting the glucose metabolism with glucosamine. The same mechanism through glucokinase has been assumed in the sensor system for the glucose concentration in VHM as in the insulin secretion in the pancreatic beta cells. Therefore, in addition to the action in the liver and pancreatic beta cells, a glucokinase-activating substance in VMH is expected to improve not only the blood sugar lever but also obesity which is a problem in a large number of type II diabetic patients.

SUMMARY OF THE INVENTION

The present invention addresses compounds represented by the formula:

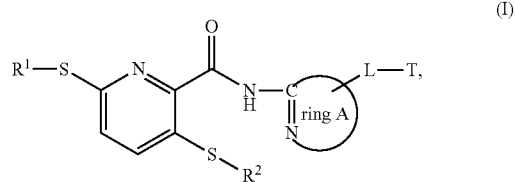

(I)

and pharmaceutically acceptable salts thereof. The present invention further relates to methods of treating diabetes and related diseases and conditions.

DETAILED DESCRIPTION OF THE INVENTION

The present invention addresses the following compounds, compounds of (1)-(23):

(1) A compound of the formula (I):

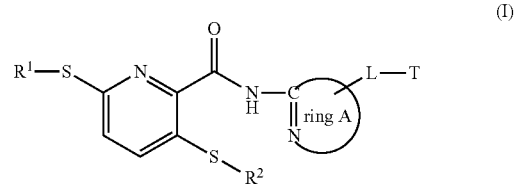

(I)

or a pharmaceutically acceptable salt thereof, wherein:
$R^1$ and $R^2$ individually represent $C_{1-6}$alkyl, 6- to 10-membered aryl group, 5- to 10-membered heteroaryl group, a 5- to 7-membered cycloalkyl group, or a 5- to 7-membered aliphatic heterocyclic group optionally substituted with 1-4 substituents independently selected from: halogen, hydroxy, oxo, $C_{1-6}$alkyl, $C_{1-6}$alkylO$C_{1-6}$alkyl, $C_{1-6}$alkoxy, CN, NR³R⁴, C(O)$_{1-2}$C$_{1-6}$alkyl, C$_{1-6}$alkylC(O)$_{1-2}$C$_{1-6}$ alkyl, C$_{1-6}$alkylS(O)$_{0-2}$, S(O)$_{0-2}$ or arylC$_{1-6}$alkyl, wherein alkyl and alkoxy substituents are further optionally substituted by 1-4 substituents independently selected from: halogen or C$_{1-6}$alkyl where said C$_{1-6}$alkyl is optionally substituted by 1-6 halogens;

ring A represents a 5- to 7-membered monocyclic or 9- to 10-membered bicyclic heteroaryl group in which the carbon atom attached to the amide nitrogen atom contained in formula (I) forms C=N together with the nitrogen atom in the ring, wherein ring A, in addition to the -L-T substituent, is further optionally substituted with 1-4 substituents independently selected from: halogen, hydroxy, C$_{1-6}$alkyl, C$_{1-6}$alkylOC$_{1-6}$alkyl, C$_{1-6}$alkoxy, C$_{1-6}$alkylS(O)$_{0-2}$, CN, NR³R⁴, C(O)$_{1-2}$C$_{1-6}$alkyl, C$_{1-6}$alkylC(O)$_{1-2}$C$_{1-6}$alkyl, S(O)$_{0-2}$ or arylC$_{1-6}$alkyl, wherein the alkyl and alkoxy substituents are further optionally substituted by 1-4 substituents independently selected from: halogen, C$_{1-6}$alkyl or C$_{1-6}$alkoxy where the alkyl and alkoxy substituents are optionally substituted by 1-6 halogens.

L represents C$_{1-6}$alkyl, C$_{1-6}$alkylOC$_{1-6}$ alkyl, C$_{1-6}$ alkoxy, NR³R⁴, C$_{1-6}$ alkylNR³R⁴, S(O)$_{0-2}$C$_{1-6}$alkyl or S(O)$_{0-2}$, wherein the alkyl and alkoxy groups are further optionally substituted by 1-4 substituents independently selected from: halogen or C$_{1-6}$alkyl where said C$_{1-6}$alkyl is optionally substituted by 1-6 halogens, T represents CO₂R, CONR³R⁴, or P(O)(OR⁵)₂, and R, R³, R⁴, and R⁵ are individually selected from hydrogen or C$_{1-6}$alkyl.

(2) A compound of the formula (I):

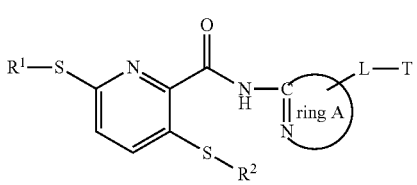

or a pharmaceutically acceptable salt thereof, wherein:

R¹ and R² individually represent 6- to 10-membered aryl group, 5- to 10-membered heteroaryl group, a 5- to 7-membered cycloalkyl group, or a 5- to 7-membered aliphatic heterocyclic group optionally substituted with 1-4 substituents independently selected from: halogen, hydroxy, oxo, C$_{1-6}$alkyl, C$_{1-6}$alkylOC$_{1-6}$alkyl, C$_{1-6}$alkoxy, CN, NR³R⁴, C(O)$_{1-2}$C$_{1-6}$alkyl, C$_{1-6}$alkylC(O)$_{1-2}$C$_{1-6}$ alkyl, C$_{1-6}$alkyl S(O)$_{0-2}$, S(O)$_{0-2}$ or arylC$_{1-6}$alkyl, wherein the alkyl and alkoxy substituents are further optionally substituted by 1-4 substituents independently selected from: halogen or C$_{1-6}$alkyl where said C$_{1-6}$alkyl is optionally substituted by 1-6 halogens;

ring A represents a 5- to 7-membered monocyclic or 9- to 10-membered bicyclic heteroaryl group in which the carbon atom attached to the amide nitrogen atom contained in formula (I) forms C=N together with the nitrogen atom in the ring, wherein ring A, in addition to the -L-T substituent, is further optionally substituted with 1-4 substituents independently selected from: halogen, hydroxy, C$_{1-6}$alkyl, C$_{1-6}$alkylOC$_{1-6}$alkyl, C$_{1-6}$alkoxy, C$_{1-6}$alkylS(O)$_{0-2}$, CN, NR³R⁴, C(O)$_{1-2}$C$_{1-6}$alkyl, C$_{1-6}$alkylC(O)$_{1-2}$C$_{1-6}$alkyl, S(O)$_{0-2}$ or arylC$_{1-6}$alkyl, wherein the alkyl and alkoxy substituents are further optionally substituted by 1-4 substituents independently selected from: halogen, C$_{1-6}$alkyl or C$_{1-6}$alkoxy where the alkyl or alkoxy substituents are optionally substituted by 1-6 halogens.

L represents C$_{1-6}$alkyl, C$_{1-6}$alkylOC$_{1-6}$ alkyl, C$_{1-6}$ alkoxy, NR³R⁴, C$_{1-6}$ alkylNR³R⁴, S(O)$_{0-2}$C$_{1-6}$alkyl or S(O)$_{0-2}$, wherein the alkyl and alkoxy groups are further optionally substituted by 1-4 substituents independently selected from: halogen or C$_{1-6}$alkyl where said C$_{1-6}$alkyl is optionally substituted by 1-6 halogens, T represents CO₂R, CONR³R⁴, or P(O)(OR⁵)₂, and R, R³, R⁴, and R⁵ are individually selected from hydrogen or C$_{1-6}$alkyl.

(3) A compound of (1) or (2), wherein R¹ is a 5-6-membered aryl or heteroaryl group, optionally substituted with 1-4 substituents independently selected from: halogen, hydroxy, oxo, C$_{1-6}$alkyl, C$_{1-6}$alkylOC$_{1-6}$alkyl, C$_{1-6}$alkoxy, CN, NR³R⁴, C(O)$_{1-2}$C$_{1-6}$alkyl, C$_{1-6}$alkylC(O)$_{1-2}$C$_{1-6}$alkyl, C$_{1-6}$alkylS(O)$_{0-2}$, S(O)$_{0-2}$ or arylC$_{1-6}$alkyl, wherein the alkyl and alkoxy substituents are further optionally substituted by 1-4 substituents independently selected from: halogen or C$_{1-6}$alkyl where said C$_{1-6}$alkyl is optionally substituted by 1-6 halogens; or a pharmaceutically acceptable salt thereof.

(4) A compound of any of (1)-(3), wherein R¹ is a phenyl group, isothiazolyl group, imidazolyl group, oxazolyl group, thiadiazolyl group, thienyl group, triazolyl group, tetrazolyl group, pyridyl group, pyrimidinyl group, furyl group, thiazolyl group, isoxazolyl group or pyrazolyl group, optionally substituted with 1-4 substituents independently selected from: halogen, hydroxy, oxo, C$_{1-6}$alkyl, C$_{1-6}$alkylOC$_{1-6}$ alkyl, C$_{1-6}$alkoxy, CN, NR³R⁴, C(O)$_{1-2}$C$_{1-6}$alkyl, C$_{1-6}$alkylC(O)$_{1-2}$C$_{1-6}$alkyl, C$_{1-6}$alkylS(O)$_{0-2}$ or S(O)$_{0-2}$, wherein the alkyl and alkoxy substituents are further optionally substituted by 1-4 substituents independently selected from: halogen or C$_{1-6}$alkyl where said C$_{1-6}$alkyl is optionally substituted by 1-6 halogens; or a pharmaceutically acceptable salt thereof.

(5) A compound of any of (1)-(4), wherein R¹ is a 5-6-membered aryl or heteroaryl group, optionally substituted with 1-4 substituents independently selected from: halogen or C$_{1-6}$alkyl, wherein C$_{1-6}$alkyl is further optionally substituted by 1-6 halogen substituents; or a pharmaceutically acceptable salt thereof.

(6) A compound of any of (1)-(5), wherein R¹ is triazolyl, pyridyl or phenyl, optionally substituted with 1-4 substituents independently selected from: halogen, hydroxy, oxo, C$_{1-6}$alkyl, C$_{1-6}$alkylOC$_{1-6}$alkyl, C$_{1-6}$alkoxy, CN, NR³R⁴, C(O)$_{1-2}$C$_{1-6}$alkyl, C$_{1-6}$alkylC(O)$_{1-2}$C$_{1-6}$ alkyl, C$_{1-6}$alkyl S(O)$_{0-2}$ or S(O)$_{0-2}$, wherein the alkyl and alkoxy substituents are further optionally substituted by 1-4 substituents independently selected from: halogen or C$_{1-6}$alkyl where said C$_{1-6}$alkyl is optionally substituted by 1-6 halogens; or a pharmaceutically acceptable salt thereof.

(7) A compound of any of (1)-(6), wherein R¹ is triazolyl, pyridyl or phenyl, optionally substituted with 1-4 substituents independently selected from: halogen or C$_{1-6}$alkyl, wherein the alkyl is further optionally substituted by 1-6 halogen substituents; or a pharmaceutically acceptable salt thereof.

(8) A compound of any of (1)-(7), wherein R¹ is triazolyl substituted with a methyl group; or a pharmaceutically acceptable salt thereof.

(9) A compound of any of (1)-(7), wherein R¹ is pyridyl; or a pharmaceutically acceptable salt thereof.

(10) A compound of any of (1)-(7), wherein R¹ is phenyl substituted with fluorine; or a pharmaceutically acceptable salt thereof.

(11) A compound of any of (1)-(10), wherein $R^2$ is a 5-6-membered aryl or heteroaryl group, optionally substituted with 1-4 substituents independently selected from: halogen, hydroxy, $C_{1-6}$alkyl, $C_{1-6}$alkylO$C_{1-6}$alkyl, $C_{1-6}$alkoxy, CN, $NR^3R^4$, $C(O)_{1-2}C_{1-6}$alkyl, $C_{1-6}$alkyl $C(O)_{1-2}C_{1-6}$alkyl, $C_{1-6}$alkylS$(O)_{0-2}$ or $S(O)_{0-2}$, wherein the alkyl and alkoxy substituents are further optionally substituted by 1-4 substituents independently selected from: halogen or $C_{1-6}$alkyl where said $C_{1-6}$alkyl is optionally substituted by 1-6 halogens; or a pharmaceutically acceptable salt thereof.

(12) A compound of any of (1)-(11), wherein $R^2$ is a phenyl group, isothiazolyl group, imidazolyl group, oxazolyl group, thiadiazolyl group, thienyl group, triazolyl group, tetrazolyl group, pyridyl group, pyrimidinyl group, furyl group, thiazolyl group, isoxazolyl group or pyrazolyl group, optionally substituted with 1-4 substituents independently selected from: halogen, hydroxy, $C_{1-6}$alkyl, $C_{1-6}$alkylO$C_{1-6}$alkyl, $C_{1-6}$alkoxy, CN, $NR^3R^4$, $C(O)_{1-2}C_{1-6}$alkyl, $C_{1-6}$alkylC$(O)_{1-2}C_{1-6}$alkyl, $C_{1-6}$alkylS$(O)_{0-2}$ or $S(O)_{0-2}$, wherein the alkyl and alkoxy substituents are further optionally substituted by 1-4 substituents independently selected from: halogen or $C_{1-6}$alkyl where said $C_{1-6}$alkyl is optionally substituted by 1-6 halogens; or a pharmaceutically acceptable salt thereof.

(13) A compound of any of (1)-(12), wherein $R^2$ is phenyl, optionally substituted with 1-4 substituents independently selected from: halogen, $C_{1-6}$alkoxy, or $C_{1-6}$alkyl, wherein the alkyl and alkoxy substituents are further optionally substituted by 1-6 halogen substituents; or a pharmaceutically acceptable salt thereof.

(14) A compound of any of (1)-(13), wherein ring A is a 5-6-membered aryl or heteroaryl group, substituted as described above for ring A; or a pharmaceutically acceptable salt thereof.

(15) A compound of any of (1)-(14), wherein ring A is a phenyl group, isothiazolyl group, imidazolyl group, oxazolyl group, thiadiazolyl group, thienyl group, triazolyl group, tetrazolyl group, pyridyl group, pyrimidinyl group, furyl group, thiazolyl group, isoxazolyl group or pyrazolyl group, substituted as described above for ring A; or a pharmaceutically acceptable salt thereof.

(16) A compound of any of (1)-(15), wherein ring A is thiazolyl or phenyl, substituted as described above for ring A; or a pharmaceutically acceptable salt thereof.

(17) A compound of any of (1)-(16), wherein ring A is thiazolyl or phenyl, substituted by -L-T; or a pharmaceutically acceptable salt thereof.

(18) A compound of any of (1)-(17), wherein L represents $C_{1-6}$alkyl or $S(O)_{0-2}C_{1-6}$ alkyl, further optionally substituted by 1-6 halogen substituents; or a pharmaceutically acceptable salt thereof.

(19) A compound of any of (1)-(18), wherein L represents $SCH_2$—, $SC(CH_3)_2$—, —$SCH_2C(CH_3)_2$—, —$CH_2CH_2$— or —$CH_2$—; or a pharmaceutically acceptable salt thereof.

(20) A compound of any of (1)-(19) wherein T is $CO_2R$; or a pharmaceutically acceptable salt thereof.

(21) A compound of any of (1)-(19) wherein T is $CONR^3R^4$; or a pharmaceutically acceptable salt thereof.

(22) A compound of any of (1)-(19) wherein T is $P(O)(OR^5)_2$; or a pharmaceutically acceptable salt thereof.

(23) A compound of (I) which is elsewhere disclosed herein or is:
Ethyl ({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetate;

({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetic acid;

3-[(4-methoxyphenyl)sulfanyl]-N-(5-{[2-(methylamino)-2-oxoethyl]sulfanyl}-1,3-thiazol-2-yl)-6-[(4-methyl-4H-1,2,4-triazol-3-yl)sulfanyl]pyridine-2-carboxamide;

2-({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)-2-methylpropanoic acid;

Ethyl 3-({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)-2,2-dimethylpropanoate;

3-({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)-2,2-dimethylpropanoic acid;

Methyl 3-{2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}propanoate;

3-{2-[({3-[(4-Methoxyphenyl)sulfanyl]-6-[(4-methyl-4H-1,2,4-triazol-3-yl)sulfanyl]pyridin-2-yl}carbonyl)amino]-1,3-thiazol-5-yl}propanoic acid;

N-[4-(2-Amino-2-oxoethyl)phenyl]-3-[(4-methoxyphenyl)sulfanyl]-6-[(4-methyl-4H-1,2,4-triazol-3-yl)sulfanyl]pyridine-2-carboxamide;

Ethyl ({2-[({3-[(4-methoxyphenyl)sulfanyl]-6-(pyridin-2-ylsulfanyl)pyridin-2-yl}carbonyl)amino]-1,3-thiazol-5-yl}sulfanyl)acetate yridine-2-carboxamide;

({2-[({3-[(4-Methoxyphenyl)sulfanyl]-6-(pyridin-2-ylsulfanyl)pyridin-2-yl}carbonyl)amino]-1,3-thiazol-5-yl}sulfanyl)acetic acid;

Ethyl {5-chloro-2-[({3-[(4-methoxyphenyl)sulfanyl]-6-(pyridin-2-ylsulfanyl)pyridin-2-yl}carbonyl)amino]-1,3-thiazol-4-yl}acetate;

{5-Chloro-2-[({3-[(4-methoxyphenyl)sulfanyl]-6-(pyridin-2-ylsulfanyl)pyridin-2-yl}carbonyl)amino]-1,3-thiazol-4-yl}acetic acid;

Methyl 3-{2-[({3-[(4-methoxyphenyl)sulfanyl]-6-(pyridin-2-ylsulfanyl)pyridin-2-yl}carbonyl)amino]-1,3-thiazol-5-yl}propanoate;

3-{2-[({3-[(4-Methoxyphenyl)sulfanyl]-6-(pyridin-2-ylsulfanyl)pyridin-2-yl}carbonyl)amino]-1,3-thiazol-5-yl}propanoic acid;

Ethyl {2-[({3-[(4-methoxyphenyl)sulfanyl]-6-(pyridin-2-ylsulfanyl)pyridin-2-yl}carbonyl)amino]-1,3-thiazol-4-yl}acetate;

{2-[({3-[(4-Methoxyphenyl)sulfanyl]-6-(pyridin-2-ylsulfanyl)pyridin-2-yl}carbonyl)amino]-1,3-thiazol-4-yl}acetic acid;

Ethyl ({5-[({3-[(4-fluorophenyl)sulfanyl]-6-[(4-methyl-4H-1,2,4-triazol-3-yl)sulfanyl]pyridin-2-yl}carbonyl)amino]thiophen-2-yl}sulfanyl)acetate;

({2-[({3-[(4-Fluorophenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetic acid;

Ethyl 3-({5-[({3-[(4-fluorophenyl)sulfanyl]-6-[(4-methyl-4H-1,2,4-triazol-3-yl)sulfanyl]pyridin-2-yl}carbonyl)amino]thiophen-2-yl}sulfanyl)-2,2-dimethylpropanoate;

3-({2-[({3-[(4-Fluorophenyl)sulfanyl]-6-[(4-methyl-4H-1,2,4-triazol-3-yl)sulfanyl]pyridin-2-yl}carbonyl)amino]-1,3-thiazol-5-yl}sulfanyl)-2,2-dimethylpropanoic acid;

Ethyl {2-[({3-[(4-fluorophenyl)sulfanyl]-6-[(4-methyl-4H-1,2,4-triazol-3-yl)sulfanyl]pyridin-2-yl}carbonyl)amino]-1,3-thiazol-5-yl}acetate;

{2-[({3-[(4-Fluorophenyl)sulfanyl]-6-[(4-methyl-4H-1,2,4-triazol-3-yl)sulfanyl]pyridin-2-yl}carbonyl)amino]-1,3-thiazol-5-yl}acetic acid;

Ethyl {5-chloro-2-[({3-[(4-fluorophenyl)sulfanyl]-6-[(4-methyl-4H-1,2,4-triazol-3-yl)sulfanyl]pyridin-2-yl}carbonyl)amino]-1,3-thiazol-4-yl}acetate;

{5-Chloro-2-[({3-[(4-fluorophenyl)sulfanyl]-6-[(4-methyl-4H-1,2,4-triazol-3-yl)sulfanyl]pyridin-2-yl}carbonyl)amino]-1,3-thiazol-4-yl}acetic acid;

Diethyl ({2-[({3-[(4-fluorophenyl)sulfanyl]-6-[(4-methyl-4H-1,2,4-triazol-3-yl)sulfanyl]pyridin-2-yl}carbonyl)amino]-1,3-thiazol-5-yl}methyl)phosphonate;

Ethyl ({5-[({3,6-bis[(4-fluorophenyl)sulfanyl]pyridin-2-yl}carbonyl)amino]thiophen-2-yl}sulfanyl)acetate;

({2-[({3,6-Bis[(4-fluorophenyl)sulfanyl]pyridin-2-yl}carbonyl)amino]-1,3-thiazol-5-yl}sulfanyl)acetic acid;

Ethyl {2-[({3,6-bis[(4-fluorophenyl)sulfanyl]pyridin-2-yl}carbonyl)amino]-5-chloro-1,3-thiazol-4-yl}acetate;

{2-[({3,6-Bis[(4-fluorophenyl)sulfanyl]pyridin-2-yl}carbonyl)amino]-5-chloro-1,3-thiazol-4-yl}acetic acid;

Ethyl {5-chloro-2-[({3-[(4-fluorophenyl)sulfanyl]-6-(pyridin-2-ylsulfanyl)pyridin-2-yl}carbonyl)amino]-1,3-thiazol-4-yl}acetate;

{5-Chloro-2-[({3-[(4-fluorophenyl)sulfanyl]-6-(pyridin-2-ylsulfanyl)pyridin-2-yl}carbonyl)amino]-1,3-thiazol-4-yl}acetic acid;

Ethyl {2-[({3-[(4-fluorophenyl)sulfanyl]-6-(pyridin-2-ylsulfanyl)pyridin-2-yl}carbonyl)amino]-1,3-thiazol-4-yl}acetate;

{2-[({3-[(4-Fluorophenyl)sulfanyl]-6-(pyridin-2-ylsulfanyl)pyridin-2-yl}carbonyl)amino]-1,3-thiazol-4-yl}acetic acid;

Ethyl ({2-[({3-[(4-fluorophenyl)sulfanyl]-6-(pyridin-2-ylsulfanyl)pyridin-2-yl}carbonyl)amino]-1,3-thiazol-5-yl}sulfanyl)acetate;

({2-[({3-[(4-Fluorophenyl)sulfanyl]-6-(pyridin-2-ylsulfanyl)pyridin-2-yl}carbonyl)amino]-1,3-thiazol-5-yl}sulfanyl)acetic acid;

Ethyl 3-({2-[({3-[(4-fluorophenyl)sulfanyl]-6-(pyridin-2-ylsulfanyl)pyridin-2-yl}carbonyl)amino]-1,3-thiazol-5-yl}sulfanyl)-2,2-dimethylpropanoate;

3-({2-[({3-[(4-Fluorophenyl)sulfanyl]-6-(pyridin-2-ylsulfanyl)pyridin-2-yl}carbonyl)amino]-1,3-thiazol-5-yl}sulfanyl)-2,2-dimethylpropanoic acid;

Methyl 3-{2-[({3-[(4-fluorophenyl)sulfanyl]-6-(pyridin-2-ylsulfanyl)pyridin-2-yl}carbonyl)amino]-1,3-thiazol-5-yl}propanoate;

3-{2-[({3-[(4-Fluorophenyl)sulfanyl]-6-(pyridin-2-ylsulfanyl)pyridin-2-yl}carbonyl)amino]-1,3-thiazol-5-yl}propanoic acid;

Ethyl (5-chloro-2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-4-yl)acetate;

(5-Chloro-2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-4-yl)acetic acid;

Ethyl [(2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)sulfanyl]acetate;

[(2-{[(6-[(4-Methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)sulfanyl]acetic acid;

Diethyl [(2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)methyl]phosphonate;

Ethyl (2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-4-yl)acetate;

(2-{[(6-[(4-Methyl-4H-1,2,4-triazol-3-yl)sulfanyl]-3-{[4-(trifluoromethyl)phenyl]sulfanyl}pyridin-2-yl)carbonyl]amino}-1,3-thiazol-4-yl)acetic acid;

Methyl 3-(2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)propanoate;

3-(2-{[(6-[(4-Methyl-4H-1,2,4-triazol-3-yl)sulfanyl]-3-{[4-(trifluoromethyl)phenyl]sulfanyl}pyridin-2-yl)carbonyl}amino]-1,3-thiazol-5-yl)propanoic acid;

Diethyl ({2-[({3-[(3,4-dichlorophenyl)sulfanyl]-6-[(4-methyl-4H-1,2,4-triazol-3-yl)sulfanyl]pyridin-2-yl}carbonyl)amino]-1,3-thiazol-5-yl}methyl)phosphonate;

Ethyl ({2-[({3-[(3,4-dichlorophenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetate;

({2-[({3-[(3,4-Dichlorophenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetic acid;

Ethyl {5-chloro-2-[({3-[(3,4-dichlorophenyl)sulfanyl]-6-[(4-methyl-4H-1,2,4-triazol-3-yl)sulfanyl]pyridin-2-yl}carbonyl)amino]-1,3-thiazol-4-yl}acetate;

{5-Chloro-2-[({3-[(3,4-dichlorophenyl)sulfanyl]-6-[(4-methyl-4H-1,2,4-triazol-3-yl)sulfanyl]pyridin-2-yl}carbonyl)amino]-1,3-thiazol-4-yl}acetic acid; or a pharmaceutically acceptable salt thereof.

The present invention also relates to pharmaceutical compositions comprising compounds of any of (1)-(23) and a pharmaceutically acceptable carrier.

Additionally, the present invention relates to use of a compound of any of (1)-(23) in the manufacture of a medicament for use in treating obesity or diabetes.

The present invention relates to the use of a compound of any of (1)-(23) in therapy, for example, in the treatment of diabetes.

The present invention further relates to a method for the treatment of a obesity or diabetes comprising administering to an individual a pharmaceutical composition comprising a compound of any of (1)-(23).

Another embodiment of the present invention includes a method of treating a condition selected from: (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension or other conditions and disorders where insulin resistance is a component, in a mammalian patient in need of such treatment, comprising administering to the patient a compound of any of (1)-(23) in an amount that is effective to treat said condition.

Yet another embodiment of the present invention include a method of treating a condition selected from: (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis,

(14) pancreatitis, (15) abdominal obesity, (16) neurodegenerative disease, (17) retinopathy, (18) nephropathy, (19) neuropathy, (20) Syndrome X, (21) hypertension or other conditions and disorders where insulin resistance is a component, in a mammalian patient in need of such treatment, comprising administering to the patient a compound of any of (1)-(23), and a compound from one of the following classes of compounds:

(1) dipeptidyl peptidase-IV (DPP-4) inhibitors (e.g., sitagliptin, alogliptin, linagliptin, vildagliptin, saxagliptin, teneligliptin, MK-3102);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro, SBS1000 and oral and inhalable formulations of insulin and insulin analogs);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., NOXG15, LY2409021);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, GSK2374697, ADX72231, RG7685, NN9924, ZYOG1, CJC-1131, and BEM-51077, including intranasal, transdermal, and once-weekly formulations thereof), and oxyntomodulin and oxyntomodulin analogs and derivatives;

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) other glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, evacetrapib and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators, such as MB1055, ETC 1002;

(21) other agonists of the G-protein-coupled receptors: (i) GPR-109, (ii) GPR-119 (e.g., MBX2982, APD597, GSK1292263, HM47000, and PSN821), and (iii) GPR-40 (e.g., TAK875, CNX011, CNX 01162, CNX 01167, JTT 851, SARI, MR 1704, TUG 770, TUG 469, TUG499, ASP 4178);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, ertugliflozin, remogloflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab);

(36) bromocriptine mesylate and rapid-release formulations thereof;

(37) GPR 120 agonists (such as KDT501), said compounds being administered to the patient in an amount that is effective to treat said condition.

The invention is further described herein using the terms defined below unless otherwise specified.

"Alkyl", as well as other groups having the prefix "alk", such as alkoxy, and the like, means carbon chains which may be linear or branched, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like.

"Alkoxy" refers to an alkyl group linked to oxygen.

"Aryl", alone or in combination, relates to a phenyl, naphthyl or indanyl group. In specific embodiments, the "aryl" is phenyl. The abbreviation "Ph" represents phenyl.

"Cycloalkyl" means a saturated cyclic hydrocarbon radical having the number of carbon atoms designated. If no number of atoms is specified, 3-7 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Heteroaryl" (HAR) unless otherwise specified, means an aromatic or partially aromatic heterocycle that contains at least one ring heteroatom selected from oxygen ("O"), sulfur ("S") and nitrogen ("N"). Heteroaryls thus includes heteroaryls fused to other kinds of rings, such as aryls, cycloalkyls and heterocycles that are not aromatic. Examples of heteroaryl groups include: pyrrolyl or pyrrole, isoxazolyl or isoxazole, isothiazolyl or isothiazole, pyrazolyl or pyrazole, pyridyl, oxazolyl or oxazole, oxadiazolyl or oxadiazole, thiadiazolyl or thiadiazole, thiazolyl or thiazole, imidazolyl or imidazole, triazolyl or triazole, tetrazolyl or tetrazole, furyl, triazinyl, thienyl, pyrimidyl, benzisoxazolyl or benzisoxazole, benzoxazolyl or benzoazole, benzothiazolyl or benzothiazole, benzothiadiazolyl or benzothiadiazole, dihydrobenzofuranyl or dihydrobenzofurane, indolinyl or indoline, pyridazinyl or pyridazine, indazolyl or indazole, isoindolyl or isoindole, dihydrobenzothienyl, indolizinyl or indolizine, cinnolinyl or cinnoline, phthalazinyl or phthalazine, quinazolinyl or quinazoline, naphthyridinyl or naphthyridine, carbazolyl or carbazole, benzodioxolyl or benzodioxole, quinoxalinyl or quinoxaline, purinyl or purine, furazanyl or furazane, isobenzylfuranyl or isobenzylfurane, benzimidazolyl or benzimidazole, benzofuranyl or benzofurane, benzothienyl or benzothiene, quinolyl or quinoline, oxo-dihydroqunoline, indolyl or indole, oxindole, isoquinolyl or isoquinoline, dibenzofuranyl or dibenzofurane, and the like. For heterocyclic and heteroaryl groups, rings and ring systems containing from 5-15 atoms are included, forming 1-3 rings.

"Heterocycle" or "heterocyclic" refers to nonaromatic cyclic ring structures in which one or more atoms in the ring, the heteroatom(s), is an element other than carbon. Heteroatoms are typically O, S or N atoms.

"Halogen" (Halo) includes fluorine, chlorine, bromine and iodine.

Unless expressly depicted or described otherwise, variables depicted in a structural formula with a "floating" bond, such as substituent -L-T, are permitted on any available carbon atom in the ring to which each is attached.

Substitution, where applicable, may be on any available carbon atom that results in a stable structure. Furthermore, where language indicates that certain groups or substituents are further optionally substituted, that language includes all groups or substituents having that feature. For example, use of the language "wherein the alkyl, alkoxy, $NR^3R^4$ or $S(O)_{0-2}$ substituents are further optionally substituted" indicates that any substituents possessing an alkyl, alkoxy, $NR^3R^4$ or $S(O)_{0-2}$ component can be substituted within that component.

Also, number ranges where provided (e.g., 1-4, 0-3, etc.) expressly include each and every number in that range as a discrete embodiment.

Atoms of the compounds described herein may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of any of (1)-(23). For example, different isotopic forms of hydrogen (H) include protium ($^1H$) and deuterium ($^2H$). Protium is the predominant hydrogen isotope found in nature. Enriching for deuterium may yield certain therapeutic advantages, such as increasing in vivo half-life or reducing dosage requirements, or may provide a compound useful as a standard for characterization of biological samples. Isotopically-enriched compounds of any of (1)-(23) described herein can be prepared without undue experimentation by conventional techniques well known to those skilled in the art or by processes analogous to those described in the Schemes and Examples herein using appropriate isotopically-enriched reagents and/or intermediates.

Individual tautomers of the compounds of any of (1)-(23), as well as mixtures thereof, are encompassed herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced within the compounds of (1)-(23). The present invention includes all such possible stereoisomers as substantially pure resolved enantiomers, racemic mixtures thereof, as well as mixtures of diastereomers. Except where otherwise specified, the formulae encompassing compounds of the present invention are shown without a definitive stereochemistry at certain positions. The present invention therefore may be understood to include all stereoisomers of compounds of any of (1)-(23) and pharmaceutically acceptable salts thereof.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of any of (1)-(23) may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of any of (1)-(23) are also included in the present invention.

Of import, the disclosed compounds have glucokinase activation activity, and therefore they are useful as therapeutic agents and/or preventive agents for diabetes mellitus as well as for diabetic complication.

Diabetic complication means diseases caused by development of diabetes mellitus and includes, for example, diabetic nephropathy, diabetic retinopathy, diabetic neurosis, diabetic arteriosclerosis, and so on.

The compounds of the present invention are considered of potential utility in the treatment of both insulin dependent diabetes mellitus (IDDM) and non-insulin dependent diabetes mellitus (NIDDM).

Insulin dependent diabetes mellitus (IDDM) is a "multifactorial autoimmune disease for which susceptibility is determined by environmental and genetic factors"; see Tisch, R. and McDevitt, H. (1996) Cell 85. 291-297. Insulin dependent diabetes mellitus is classified as type I and type II depending on the predisposition.

In type II diabetes mellitus, the blood sugar after meals is markedly maintained at a high level for a long period of time in comparison with that of healthy persons.

Compounds disclosed herein may be used in the manufacture of medicaments for treating one or more of the following diseases or conditions, including, without limitation:

(1) noninsulin dependent diabetes mellitus (type 2 diabetes);
(2) hyperglycemia;
(3) metabolic syndrome/syndrome X;
(4) obesity;
(5) ischemia and myocardial infarction;
(6) neurological disorders such as Alzheimer's disease, schizophrenia, and impaired cognition;
(5) hypercholesterolemia;
(6) hypertriglyceridemia (elevated levels of triglyceride-rich-lipoproteins);
(7) mixed or diabetic dyslipidemia;
(8) low HDL cholesterol;
(9) high LDL cholesterol;
(10) hyperapobetalipoproteinemia; and
(11) atherosclerosis.

The present invention also relates to a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound of any of (1)-(23) or a pharmaceutically acceptable salt thereof. The compound may be used alone or advantageously may be administered with a cholesterol biosynthesis inhibitor, particularly an HMG-CoA reductase inhibitor (e.g., simvastatin, atorvastatin, and the like). The compound may also be used advantageously in combination with other lipid lowering drugs such as cholesterol absorption inhibitors (e.g., stanol esters, sterol glycosides or azetidinones such as ezetimibe), ACAT inhibitors (e.g., avasimibe), CETP inhibitors (e.g. anacetrapib), niacin, bile acid sequestrants, microsomal triglyceride transport inhibitors, and bile acid reuptake inhibitors. Such combination treatments are useful for the treatment or control of conditions such as hypercholesterolemia, atherosclerosis, hyperlipidemia, hypertriglyceridemia, dyslipidemia, high LDL, and low HDL.

Another aspect of the invention provides a method for the treatment and control of obesity or metabolic syndrome, which comprises administering to a patient in need of such treatment a therapeutically effective amount of a compound of (1)-(23). The compound may be used alone or advantageously may be administered with an anti-obesity agent, such as a lipase inhibitor (e.g., orlistat,) or a monoamine neurotransmitter uptake inhibitor (e.g., sibutramine or phentermine) The compound may also be used advantageously in combination with CB-1 inverse agonists or antagonists (e.g., rimonabant or taranabant).

The present invention further relates to a method of treating hyperglycemia, diabetes or insulin resistance in a mammalian patient in need of such treatment which comprises administering to said patient a compound of any of (1)-(23) in an amount that is effective to treat hyperglycemia, diabetes or insulin resistance.

Yet another aspect of the invention that is of interest relates to a method of treating atherosclerosis in a mammalian patient in need of such treatment, comprising administering to said patient a compound of any of (1)-(23) in an amount that is effective to treat atherosclerosis.

Yet another aspect of the invention that is of interest relates to a method of delaying the onset of one of the aforementioned conditions and disorders where insulin resistance is a component in a mammalian patient in need thereof, comprising administering to the patient a compound of any of (1)-(23) in an amount that is effective to delay the onset of said condition.

Yet another aspect of the invention that is of interest relates to a method of reducing the risk of developing one of the aforementioned conditions and disorders where insulin resistance is a component in a mammalian patient in need thereof, comprising administering to the patient a compound of any of (1)-(23) in an amount that is effective to reduce the risk of developing said condition.

Yet another aspect of the invention that is of interest relates to a method of treating a condition or reducing the risk of developing a condition or delaying the onset of a condition selected from the group consisting of (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient a compound of any of (1)-(23) in an amount that is effective to treat said condition, and a compound selected from the group consisting of:

(1) dipeptidyl peptidase-IV (DPP-4) inhibitors (e.g., sitagliptin, alogliptin, linagliptin, vildagliptin, saxagliptin, teneligliptin, omarigliptin);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro, SBS1000 and oral and inhalable formulations of insulin and insulin analogs);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., NOXG15, LY2409021);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, GSK2374697, ADX72231, RG7685, NN9924, ZYOG1, CJC-1131, and BEM-51077, including intranasal, transdermal, and once-weekly formulations thereof), and oxyntomodulin and oxyntomodulin analogs and derivatives;

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) other glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, evacetrapib and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators, such as MB1055, ETC 1002;

(21) other agonists of the G-protein-coupled receptors: (i) GPR-109, (ii) GPR-119 (e.g., MBX2982, APD597, GSK1292263, HM47000, and PSN821), and (iii) GPR-40 (e.g., TAK875, CNX011, CNX 01162, CNX 01167, JTT 851, SARI, MR 1704, TUG 770, TUG 469, TUG499, ASP 4178);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, ertugliflozin, remogloflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab);

(36) bromocriptine mesylate and rapid-release formulations thereof;

(37) GPR 120 agonists (such as KDT501); said compounds being administered to the patient in an amount that is effective to treat said condition.

For dosing purposes, any suitable route of administration may be employed for providing a mammal, especially a human, with an effective amount of a compound of the present invention. Dosage forms may include tablets, troches, dispersions, suspensions, solutions, capsules, creams, ointments, aerosols, and the like. Most preferably, compounds of any of (1)-(23) are administered orally. The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus or other diseases for which compounds of any of (1)-(23) are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 350 milligrams. For a particularly potent compound, the dosage for an adult human may be as low as 0.1 mg. The dosage regimen may be adjusted within this range or even outside of this range to provide the optimal therapeutic response. Oral administration will usually be carried out using tablets or capsules. Examples of doses in tablets and capsules are 0.1 mg, 0.25 mg, 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 12 mg, 15 mg, 20 mg, 25 mg, 50 mg, 100 mg, 200 mg, 350 mg, 500 mg, 700 mg, 750 mg, 800 mg and 1000 mg. Other oral forms may also have the same or similar dosages.

Another aspect of the invention that is of interest is a pharmaceutical composition comprised of a compound of any of (1)-(23) in combination with a pharmaceutically acceptable carrier. The pharmaceutical compositions of the present invention comprise a compound of any of (1)-(23) as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, palmitate, pamoate (embonate), pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

A pharmaceutical composition may also comprise a prodrug, or a pharmaceutically acceptable salt thereof, if a prodrug is administered.

The compositions are typically suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the condition being treated and on the particular active ingredient selected. They may be conveniently presented in unit dosage form and prepared by any of the methods well-known in the art.

In practical use, compounds of any of (1)-(23) can be combined as the active ingredient in intimate admixture with the pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage form. Solid pharmaceutical carriers are therefore typically employed. If desired, tablets may be coated by standard aqueous or nonaqueous techniques. Such compositions and preparations typically comprise at least about 0.1 percent of active compound, the remainder of the composition being the carrier. The percentage of active compound in these compositions may, of course, be varied and is conveniently between about 2 percent to about 60 percent of the weight of the dosage form. The amount of active compound in such therapeutically useful compositions is such that an effective dosage will be delivered.

Alternatively, the active compound can be administered intranasally as, for example, in the form of liquid drops or a spray.

The tablets, capsules and the like also typically contain a binder. Examples of suitable binders include gum tragacanth, acacia, gelatin and a synthetic or semisynthetic starch derivative, such as hydroxypropylmethylcellulose (HPMC); excipients such as dicalcium phosphate; a disintegrating agent such as corn starch, potato starch, alginic acid; a lubricant such as magnesium stearate; and in some instances, a sweetening agent such as sucrose, lactose or saccharin. When the dosage form employed is a capsule, it may contain, in addition to the components described above, a liquid carrier such as fatty oil.

Various other materials may be present as coatings or to modify the physical form of the dosage unit. For instance, tablets may be coated with shellac, sugar or both. Syrups and elixirs typically contain, in addition to the active ingredient, sucrose as a sweetening agent, methyl or propylparabens as a preservative, a dye and a flavoring such as cherry or orange flavor.

The compounds of any of (1)-(23) may also be administered parenterally. Solutions or suspensions of these active compounds can be prepared in water, saline or another biocompatible vehicle, suitably mixed with a surfactant, buffer, and the like. Dispersions can also be prepared in glycerol, liquid polyethylene glycols and mixtures thereof in an oil. Under ordinary conditions of storage and use, these preparations can also contain a preservative to prevent the growth of microorganisms.

The pharmaceutical forms suitable for injectable use include sterile aqueous solutions and dispersions, and sterile powders for the extemporaneous preparation of sterile injectable solutions and dispersions. The preparation should be prepared under sterile conditions and be fluid to the extent that easy syringability exists. It should be sufficiently stable under the conditions of manufacture and storage and preserved against the growth of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and suitable oils.

As discussed supra, compounds of the present invention may be used in combination with other drugs that may also be useful in the treatment or amelioration of the individual diseases and conditions described herein. Such other drugs may be administered by a route and in an amount commonly used therefore, contemporaneously or sequentially with a compound of any of (1)-(23). In the treatment of patients who have type 2 diabetes, insulin resistance, obesity, metabolic syndrome, neurological disorders, and co-morbidities that accompany these diseases, more than one drug is commonly administered. The compounds of this invention may generally be administered to a patient who is already taking one or more other drugs for these conditions.

When a compound of any of (1)-(23) is used contemporaneously with one or more other drugs, a pharmaceutical composition in unit dosage form containing such other drugs and the compound of any of (1)-(23) is preferred. However, the combination therapy also includes therapies in which a compound of any of (1)-(23) and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of any of (1)-(23).

Examples of other active ingredients that may be administered separately or in the same pharmaceutical composition in combination with a compound of any of (1)-(23) include, but are not limited to:

(1) dipeptidyl peptidase-IV (DPP-4) inhibitors (e.g., sitagliptin, alogliptin, linagliptin, vildagliptin, saxagliptin, teneligliptin, MK-3102);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) dual agonists (e.g., ZYH2, ZYH1, GFT505, chiglitazar, muraglitazar, PPARα/γ aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO partial 2004/020409, WO 2004/020408, and WO 2004/066963); and (4) PPARγ agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro, SBS1000 and oral and inhalable formulations of insulin and insulin analogs);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., NOXG15, LY2409021);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, GSK2374697, ADX72231, RG7685, NN9924, ZYOG1, CJC-1131, and BEM-51077, including intranasal, transdermal, and once-weekly formulations thereof), and oxyntomodulin and oxyntomodulin analogs and derivatives;

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) other glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, evacetrapib and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators, such as MB1055, ETC 1002;

(21) other agonists of the G-protein-coupled receptors: (i) GPR-109, (ii) GPR-119 (e.g., MBX2982, APD597, GSK1292263, HM47000, and PSN821), and (iii) GPR-40 (e.g., TAK875, CNX011, CNX 01162, CNX 01167, JTT 851, SARI, MR 1704, TUG 770, TUG 469, TUG499, ASP 4178);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, ertugliflozin, remogloflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab);

(36) bromocriptine mesylate and rapid-release formulations thereof; or (37) GPR 120 agonists (such as KDT501).

Another aspect of the invention that is of interest relates to the use of a compound of any of (1)-(23) in the manufacture of a medicament for use in treating a disease or condition described herein.

The glucokinase-activating capability of the compounds (I) may be determined according to methods previously described (e.g., Diabetes, 45, 1671-1677, 1996).

The glucokinase activity can, for instance, be determined without directly measuring glucose-6-phosphate by measuring the amount of Thio-NADH generated during the production of phosphogluconolactone from glucose-6-phosphate by a reporter enzyme glucose-6-phosphate dehydrogenase.

To test the exemplified compounds, the following assay was employed. Recombinant human liver glucokinase was expressed as a FLAG fusion protein in *E. coli*, and purified on ANTIFLAG M2 AFFINITY GEL (Sigma). The assay was carried out at 30° C. in a 96-well plate. In the plate was distributed 69 μl each of assay buffer (25 mM Hepes Buffer: pH=7.2, 2 mM $MgCl_2$, 1 mM ATP, 0.5 mM TNAD, 1 mM dithiothreitol), to which was added 1 μl of a DMSO solution of the compound or DMSO as control. Then, 20 μl of pre-ice-cooled enzyme mixture (FLAG-GK, 20 U/ml G6PDH) was distributed thereto, to which was added 10 μl of 25 mM glucose as substrate to initiate the reaction (final glucose concentration=2.5 mM). After starting the reaction, the absorbance at 405 nm was measured every 30 seconds for 10 minutes to evaluate the compound based on the initial increase for 5 minutes. FLAG-GK was added so that the increase of absorbance after 5 minutes fell between 0.05 to 0.1 in the presence of 1% DMSO.

The OD values of the respective compounds were measured in the respective concentrations, wherein the OD value of DMSO as control is regarded as 100%. From the OD values at the respective concentrations, Emax (%, 2.5 mM Glu) and EC50 (nM, 2.5 mM Glu) were calculated and used as indicators of the GK activation capability of the compounds. According to the above assay, the GK activation capability of the exemplified compounds of the present invention was determined. The following table shows the results.

TABLE

| Ex. # | EC50 | Emax |
|---|---|---|
| 1 | 7.5 | 470.9 |
| 2 | 56.8 | 446.1 |
| 3 | 10.8 | 572.1 |
| 4 | 65.1 | 416.8 |
| 5 | 14.3 | 490.4 |
| 6 | 16.0 | 425.4 |
| 7 | 23.4 | 549.9 |
| 8 | 58.7 | 625.6 |
| 9 | 1891 | 190.6 |
| 10 | 35.2 | 498 |
| 11 | 10.9 | 509.4 |
| 12 | 47.6 | 427.1 |
| 13 | 9.0 | 583.8 |
| 14 | 289.6 | 486.4 |
| 15 | 139.6 | 645.1 |
| 16 | 274.6 | 524 |
| 17 | 106.4 | 698.1 |
| 18 | 13.4 | 436.2 |
| 19 | 23.1 | 426.1 |
| 20 | 16.9 | 460.2 |
| 21 | 17.2 | 473.4 |
| 22 | 49.3 | 534.6 |
| 23 | 137.2 | 656.9 |
| 24 | 8.0 | 378 |
| 25 | 18.6 | 525.2 |
| 26 | 136.4 | 376.6 |
| 27 | 386.5 | 182.1 |
| 28 | 171.8 | 342.9 |
| 29 | 15970 | 158.4 |
| 30 | 16.3 | 393.3 |
| 31 | 127.3 | 436.4 |
| 32 | 16.1 | 642.7 |
| 33 | 4661 | 455.5 |
| 34 | 413.2 | 761.7 |
| 35 | 83.8 | 504 |
| 36 | 34 | 514.1 |
| 37 | 129 | 450.2 |
| 38 | 32.0 | 550.5 |
| 39 | 726.5 | 467.8 |
| 40 | 427.7 | 657.8 |
| 41 | 18.9 | 296.3 |
| 42 | 44 | 465.9 |
| 43 | 28.3 | 384 |
| 44 | 33.7 | 349.3 |
| 45 | 349.5 | 272.6 |
| 46 | 66.3 | 465.7 |
| 47 | 222.1 | 633.4 |
| 48 | 71.8 | 428.4 |
| 49 | 173 | 549.4 |
| 50 | 57.1 | 378.6 |
| 51 | 6.2 | 478.6 |
| 52 | 16.6 | 430.6 |
| 53 | 7.6 | 426.1 |
| 54 | 23.3 | 522.6 |

As shown in the table, the compounds of the present invention have sufficient GK activation capability when Emax and EC50 are employed as indicators. Furthermore, the disclosed and exemplified compounds have the potential to be more liver-preferring over the pancreas, enabling the disclosed and exemplified compounds to potentially reduce the risk of hypoglycemia in individuals being treated.

The compounds of the invention can be prepared using the synthetic schemes described herein as well as any of several alternate methods which will be apparent to a chemist skilled in the art. The following abbreviations may be used in the synthetic schemes or Examples: AcCl is acetyl chloride; DCM is dichloromethane; DIEA is N,N-Diisopropylethylamine; DMA is dimethylacetamide; DMAP is dimethylaminopyridine; DMF is N,N-dimethylformamide; DMI is 1,3-dimethyl-2-Imidazolidinone; DMSO is dimethyl sulfoxide; DTT is dithiothreitol; EDC or EDCI is 1-ethyl-3-[3-(dimethylamino)propyl]-carbodiimide HCl; EtOAc is ethyl acetate; EtOH is ethanol; h is hours; HCl is hydrochloric acid; HOBt is 1-hydroxybenzotriazole; HPLC is high performance liquid chromatography; LAH is lithium aluminum hydride; M is molar; min is minutes; mmol is millimole; NCS is N-chlorosuccinimide; rt or RT is room temperature; SM is starting material; TEA is triethylamine; TFA is trifluoroacetic acid; THF is tetrahydrofuran; TLC is thin layer chromatography; and TNAD is thionicotinamide-adenine dinucleotide.

General Schemes

Certain compounds of formula I in the invention may be prepared starting from the compound of formula VII by Method A as shown in the following Reaction Scheme. A person of skilled in the art will understand that additional methods may also be used. A person skilled in the art will appreciate that alternative reagents, temperatures and solvents may be used to effect the same transformation. In other words, the compounds of the invention can be made using organic synthesis using starting materials, reagents and reactions well known in the art.

Method A converted to the corresponding tert-butyl esters of formula VI using any conventional esterification methods.

Thus resulting compound VI may be isolated and purified by conventional means, for example, extraction, vacuum condensation, chromatography, and so on.

Step 2

In this step, the $X_1$ group of formula VI can be displaced by an arylthio group in the presence of a base, such as potassium carbonate and cesium carbonate, in a polar solvent, such as DMF, at ambient temperature or a slightly higher temperature.

Thus resulting compound V may be isolated and purified by conventional means, for example, extraction, vacuum condensation, chromatography, and so on.

Step 3

In this step, the $X_2$ group of formula V can be displaced by an arylthio or heteroaryl thio group in the presence of a base, such as potassium tert-butoxide, potassium carbonate and cesium carbonate, in a polar solvent, such as DMF and DMA, usually at higher temperature.

Thus resulting compound IV may be isolated and purified by conventional means, for example, concentration extraction, vacuum condensation, chromatography, and so on.

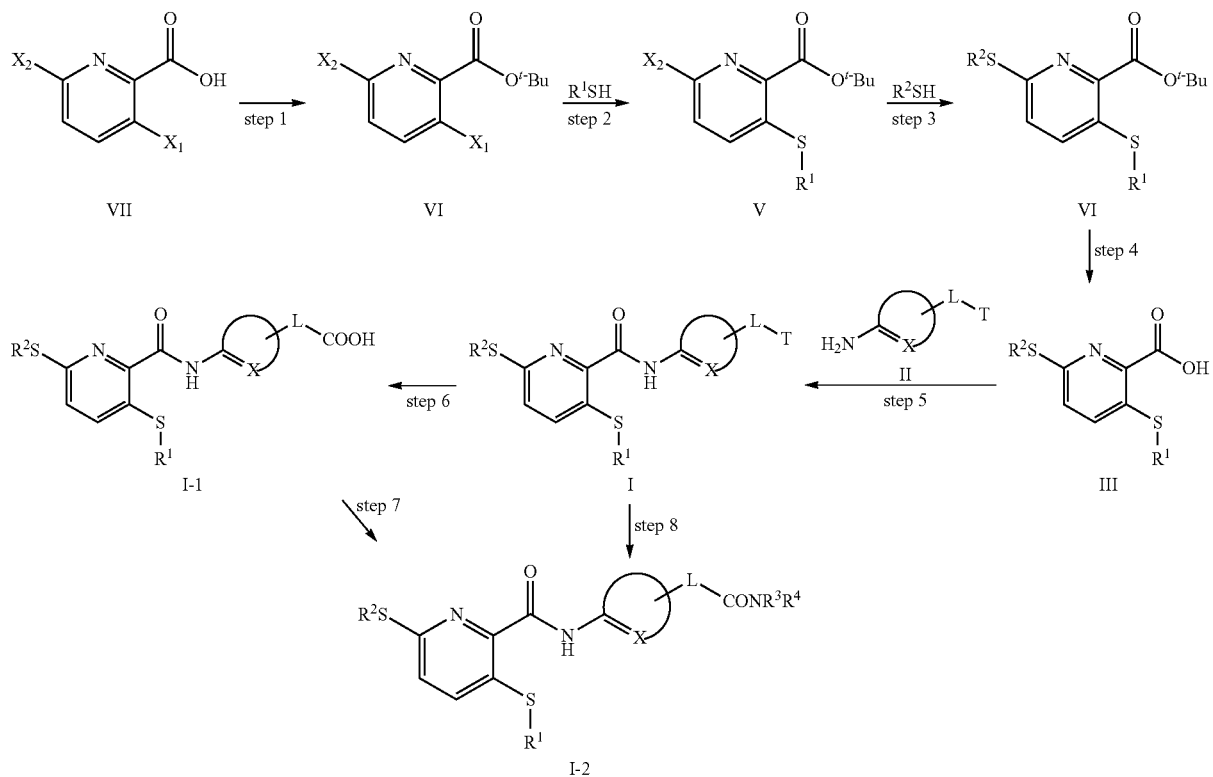

wherein $X_1$ and $X_2$ are functional groups that will be converted into aryl- or heteroaryl-thio groups, preferably chloro or fluoro;

$R^1$, $R^2$, $R^3$, $R^4$, L, T and X are as above.

Step 1

The carboxylic acids of formula VII wherein $X_1$ and $X_2$ are both chloro is commercially available. The carboxylic acids of formula VII wherein $X_1$ is fluoro and $X_2$ is chloro is also commercially available. The carboxylic acids can be Step 4

In this step, the tert-butyl ester prepared from Step 3 can be converted to the corresponding carboxylic acid by the treatment of a strong acid, such as TFA, HCl and so on.

Thus resulting compound III may be isolated and purified by conventional means, for example, concentration, extraction, vacuum condensation, chromatography, and so on. Alternatively, the compound III may be used in the subsequent step without purification.

Step 5

In this step, acid III is allowed to react with the amino compound (II) to give compound I. The reaction may be carried by performing amide-formation reactions by a method as described previously (for example, Comprehensive Organic Synthesis, 6, Pergamon Press, 1991), by a method according thereto, or by a combination of these and ordinary methods.

Thus resulting compound I may be isolated and purified by conventional means, for example, concentration, extraction, vacuum condensation, chromatography, and so on.

Step 6

In this step, compound I wherein T is an carboxylic ester group may be saponified by the treatment of a base followed by acidification to give the corresponding carboxylic acid I-1. The base used in this step may be alkali hydroxides, such as lithium hydroxide and sodium hydroxide.

Thus resulting compound I-1 may be isolated and purified by conventional means, for example, concentration, extraction, vacuum condensation, chromatography, and so on.

Step 7

In this step, carboxylic acid I-1 is allowed to reacted with an amine to give the corresponding carboxamde. The reaction may be carried by performing amide-formation reactions by a method as described previously for example, Comprehensive Organic Synthesis, 6, Pergamon Press, 1991), by a method according thereto, or by a combination of these and ordinary methods.

Thus resulting compound I-2 may be isolated and purified by conventional means, for example, concentration, extraction, vacuum condensation, chromatography, and so on.

Step 8

In this step, compound I wherein T is an carboxylic ester group may be transformed into the corresponding carboxamide I-2 by heating with an amine or by the reaction with an amine in the presence of a Lewis acid, such as trimethylaluminum, etc, with or without heating.

Thus resulting compound I-2 may be isolated and purified by conventional means, for example, concentration, extraction, vacuum condensation, chromatography, and so on.

Alternatively, certain compounds of formula I in the invention may be prepared starting from the compound of formula X by Method B as shown in the following Reaction Scheme.

Method B

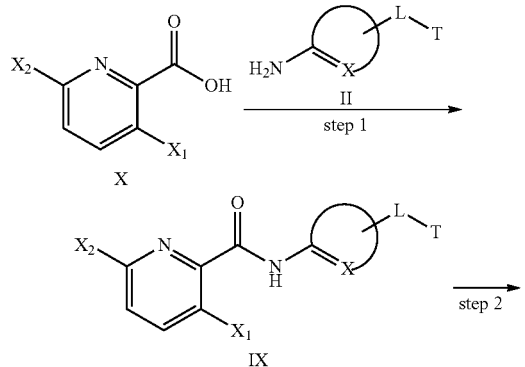

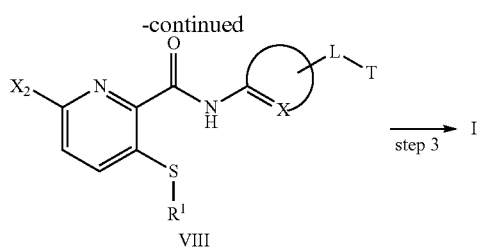

Step 1

In this step, acid X is allowed to react with the amino compound (II) to give compound IX. The reaction may be carried by performing amide-formation reactions by a method as described previously (for example, Comprehensive Organic Synthesis, 6, Pergamon Press, 1991), by a method according thereto, or by a combination of these and ordinary methods.

Thus resulting compound IX may be isolated and purified by conventional means, for example, concentration, extraction, vacuum condensation, chromatography, and so on.

Step 2

In this step, the $X_1$ group of formula IX can be displaced by an arylthio group in the presence of a base, such as potassium carbonate and cesium carbonate, in a polar solvent, such as DMF, at ambient temperature or a slightly higher temperature.

Thus resulting compound VIII may be isolated and purified by conventional means, for example, extraction, vacuum condensation, chromatography, and so on.

Step 3

In this step, the $X_2$ group of formula VIII can be displaced by an arylthio or heteroaryl thio group in the presence of a base, such as potassium tert-butoxide, potassium carbonate and cesium carbonate, in a polar solvent, such as DMF and DMA, usually at higher temperature.

Thus resulting compound I may be isolated and purified by conventional means, for example, concentration extraction, vacuum condensation, chromatography, and so on.

INTERMEDIATES

Preparation of ethyl [(2-amino-1,3-thiazol-5-yl)sulfanyl]acetate

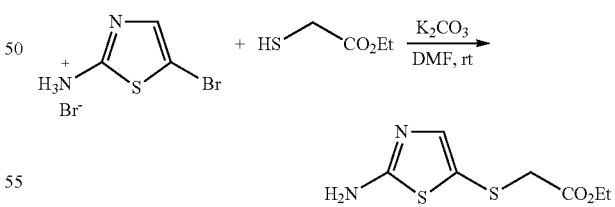

A flask charged with a magnetic stirring bar, 5-bromo-2-aminothiazole hydrobromide salt (3.00 g, 11.54 mmol), potassium carbonate (4.78 g, 34.60 mmol) and anhydrous DMF (10 mL) was purged with nitrogen and cooled in an ice-water bath. To the stirring suspension was added ethyl thioglycolate (1.387 g, 11.54 mmol). The mixture was allowed to warm to rt and stirred for 16 h. It was diluted with ethyl acetate (50 mL) and washed with water (50 mL). The aqueous layer was extracted with ethyl acetate (50 mL). The combined organic layers were washed with water (50 mL×2)

and brine (50 mL). The organic layer was separated and dried over sodium sulfate. After filtration and concentration, the crude product was purified by flash column chromatography (Biotage Flash 40M) gradually eluting with 30-100% ethyl acetate in hexane (with 2% TEA) to afford ethyl [(2-amino-1,3-thiazol-5-yl)sulfanyl]acetate as a yellow oil (1.72 g, 68%), which solidified after refrigeration.

Preparation of ethyl 2-[(2-amino-1,3-thiazol-5-yl)sulfanyl]-2-methylpropanoate

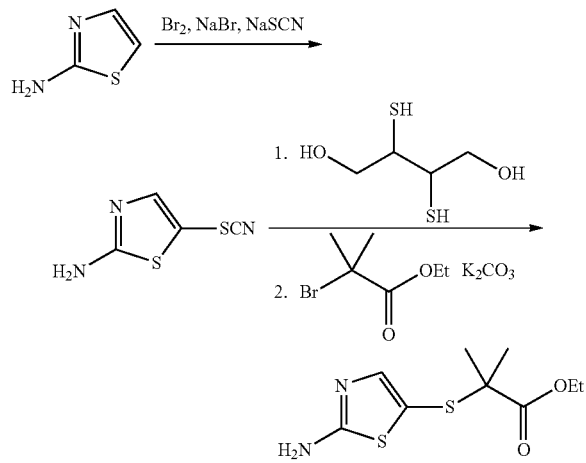

A solution of 2-aminothiazole (3.5 g, 35 mmol) and sodium thiocyanate (8.9 g, 110 mmol) in methanol (40 mL) was stirred in an ice-acetone bath (−10° C.) for 5 min A solution of bromine (1.8 mL, 34.9 mmol) in methanol (10 mL) saturated with sodium bromide was added dropwise by a glass pipette over 20 min keeping the internal temperature between −5 to 0° C. Some off-white precipitations were formed at the end of addition. The suspension was stirred at 0° C. for another 30 min, and then it was kept in a refrigerator overnight. The mixture was stirred at 0° C. for 2.5 h before it was poured into 150 mL ice-water. The suspension was stirred for 10 min and precipitations were collected by filtration followed by rinsing with ice-water (10 mL) three times. The yellow solid was dried at 60° C. under vacuum for 1 h to afford 2-amino-1,3-thiazol-5-yl thiocyanate (1.58 g, 29%).

In a 50 mL flask was charged with a stirring bar, DTT (491 mg, 3.18 mmol) and 2-amino-5-thiocyanato-thiazole (500 mg, 3.18 mmol). The flask was sealed and purged with nitrogen. Methanol (15 mL) was added to it and the mixture was stirred at room temperature for 1.5 h. Potassium carbonate (527 mg, 3.82 mmol) and ethyl 2-bromoisobutyrate (682, 3.50 mmol) were added to the reaction and stirred under nitrogen overnight. Most of the solvent was evaporated and the residue was partitioned between water and ethyl acetate. The organic layer was washed once with water and then brine. It was separated and dried over sodium sulfate. After concentration in vacuo the residue was purified by flash column chromatography eluting with 1:1 ethyl acetate:hexane. The fractions were combined and concentrated. The residue was dissolved in diethyl ether and washed with water three times. The organic layer was dried over sodium sulfate and concentrated to afford the title compound as a yellow oil (423 mg, 54%).

Preparation of ethyl 3-[(2-amino-1,3-thiazol-5-yl)sulfanyl]-2,2-dimethylpropanoate

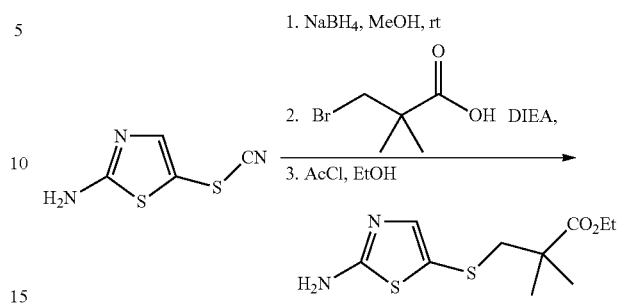

The solution of 5-thiocyanato-thiazol-2-ylamine (4.00 g, 25.4 mmol) in methanol (100 mL, degassed by bubbling nitrogen for 15 min) was added sodium borohydride (1.155 g, 30.5 mmol) in one portion. The reaction was stirred for 30 min under nitrogen and was added 3-bromo-2,2-dimethyl-propionic acid (6.91 g, 38.2 mmol) in one portion followed by diisopropylethylamine (4.54 mL, 25.4 mmol). The reaction was stirred overnight at rt. It was added about 150 mL of 5% citric acid to adjust the pH to 4. Most organic solvent was removed and the mixture was extracted with 2:1 chloroform:2-propanol four times. The combined organic layers were dried over sodium sulfate and concentrated to give brown glue-like crude product (8.7 g).

Acetyl chloride (5.45 mL, 76.0 mmol) was added slowly to anhydrous ethanol (70 mL) with stirring at 0° C. to generate a solution of HCl in ethanol. The solution was added to a solution of the crude product above in ethanol (30 mL) and stirred for 18 h at 50° C. Most solvent was removed in vacuo and the residue was purified by flash column chromatography to give the title compound as a brown solid (4.58 g, 69%).

Preparation of 5-(3-methoxy-3-oxopropyl)-1,3-thiazol-2-aminium bromide

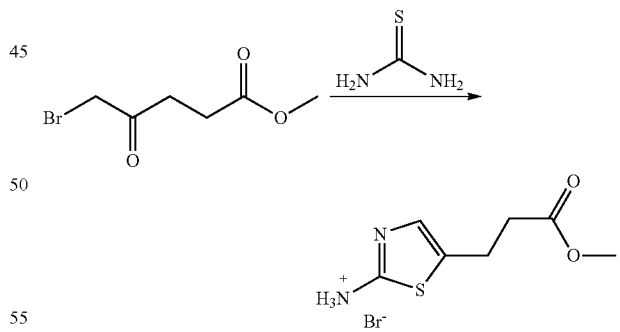

Methyl 5-bromo-4-oxopentanoate (prepared by a literature procedure: Synthesis 2007, 23, 3731-3735) (3.64 g, 17.41 mmol) and thiourea (1.326 g, 17.41 mmol) in ethanol were heated to reflux overnight. The reaction mixture was cooled to room temperature and the white crystals were filtrated and washed with cool ethanol (5 mL×2), ethyl acetate (10 mL) and diethyl ether (20 mL) in the order given. They were collected and dried under vacuum to give 4.2 g of 5-(3-ethoxy-3-oxopropyl)-1,3-thiazol-2-aminium bromide as pink solids (90%). (ES$^+$) parent m/z: 187.18 (M+H)$^+$.

Preparation of ethyl 2-amino-5-chlorothiazole-4-acetate

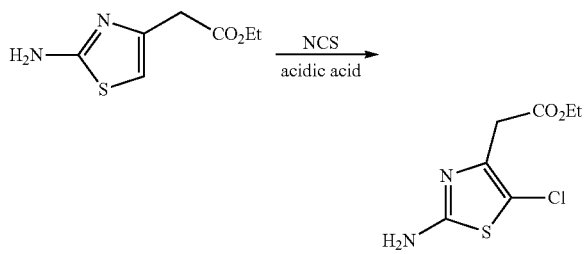

Ethyl 2-aminothiazole-4-acetate (5.48 g, 29.4 mmol) in acetic acid (300 ml) was added NCS (4.32 g, 32.4 mmol) at room temperature. The reaction was stirred for 2 h and it was concentrated to give a red residue. Solids were formed and the mixture was suspended in acetone/diethyl ether (1/1, 20 mL) stirring overnight. The solids were filtrated and washed with acetone/diethyl ether (1/1, 50 mL) in several portions to give ethyl 2-amino-5-chlorothiazole-4-acetate (3.24 g, 14.68 mmol, 49.9% yield) as a brick-red solid.

Preparation of diethyl [(2-amino-1,3-thiazol-5-yl)methyl]phosphonate

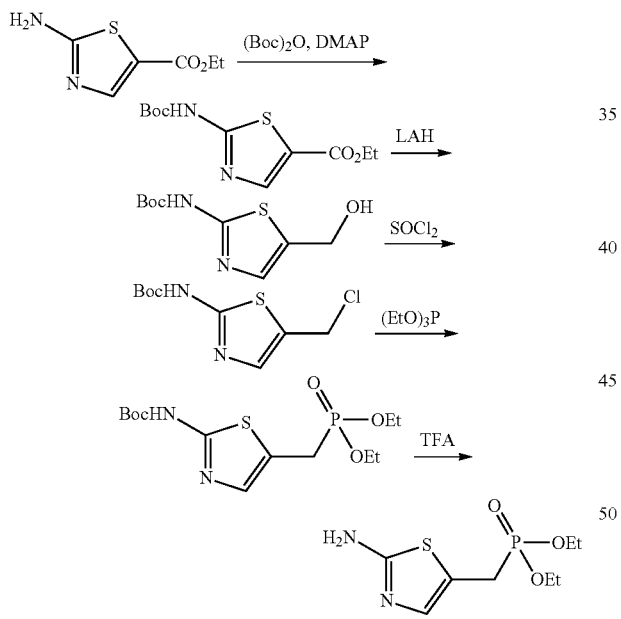

Ethyl 2-amino-1,3-thiazole-5-carboxylate (4.33 g, 25.1 mmol), (Boc)$_2$O (6.13 ml, 26.4 mmol) and DMAP (0.061 g, 0.503 mmol) in THF (50 ml) was stirred overnight. White solids were form, which can barely be dissolved in DMSO or methanol but not in most organic solvent and water. It was filtrated and washed with ethyl acetate, dried under high vacuum to give ethyl 2-[(tert-butoxycarbonyl)amino]-1,3-thiazole-5-carboxylate (5.46 g, 20.12 mmol, 80% yield) as a pale white solid. m/z: 271.10 [M−1]$^-$.

To a clean dry 500 mL flask was charged with a magnetic stirring bar, ethyl 2-[(tert-butoxycarbonyl)amino]-1,3-thiazole-5-carboxylate (5.46 g, 20.12 mmol) and anhydrous THF (100 ml). The solution was cooled to 0° C. by an ice-bath and was slowly added 1 M LiAlH$_4$ in diethyl ether (24.15 ml, 24.15 mmol) over 5 min. The mixture was stirred for 20 min and the ice-bath was removed to allow the reaction warmed to room temperature, stirring for another 2 h. It was cooled to 0° C. and quenched carefully with water (1 mL), then 15% NaOH (3 mL). The mixture was stirred vigorously for 2 h. The white solids were removed by filtration through Celite. To the filtrate was added about 15 g of silica gel and it was concentrated in vacuo. The silica gel was dried and loaded on a Biotage column and eluted with 0-100% ethyl acetate to give tert-butyl [5-(hydroxymethyl)-1,3-thiazol-2-yl]carbamate (2.9 g, 12.59 mmol, 62.6% yield) as a white solid. $^1$H-NMR (500 MHz, DMSO-d$_6$): δ (ppm)=11.28 (s, 1H), 7.18 (s, 1H), 5.32 (t, J=6 Hz, 2H), 4.55 (d, J=6 Hz, 1H), 1.49 (s, 9H). (ES$^+$) m/z: 230.92 (M+H)$^+$.

Thionyl chloride (3.68 ml, 50.4 mmol) was added to the suspension of tert-butyl [5-(hydroxymethyl)-1,3-thiazol-2-yl]carbamate (2.9 g, 12.59 mmol) in DCM (10 ml) at 0° C. The reaction was stirred for 1 h, then it was concentrated in vacuo. The residue was used in the next step without further purification. $^1$H-NMR (500 MHz, DMSO-d$_6$): δ (ppm)=7.41 (s, 1H), 5.01 (t, J=6 Hz, 2H), 1.50 (s, 9H).

To a 250 mL of flask was charged a magnetic stirring bar, tert-butyl [5-(chloromethyl)-1,3-thiazol-2-yl]carbamate (3.13 g, 12.58 mmol), anhdrous THF (60 ml) and triethyl phosphite (17.52 ml, 101 mmol). The reaction mixture was heated to reflux overnight. Cooled to rt. Concentrated and purified by Biotage (Flash 40M, 0-100% ethyl acetate in hexane) to give diethyl ({2-[(tert-butoxycarbonyl)amino]-1,3-thiazol-5-yl}methyl)phosphonate (4.28 g, 12.22 mmol, 97% yield) as a colorless oil. (ES$^+$) m/z: 350.18 (M+H)$^+$.

A solution of diethyl ({2-[(tert-butoxycarbonyl)amino]-1,3-thiazol-5-yl}methyl)phosphonate (4.23 g, 12.07 mmol) in DCM (45 ml) was added TFA (25 ml, 324 mmol) and stirred for 2 h at rt. It was concentrated and diluted with DCM, washed with sodium bicarbonate and then brine. The organic layer was dried over sodium sulfate and concentrated. The residue was purified by Biotage (Flash 40 M, 0-8% methanol in DCM) to give diethyl [(2-amino-1,3-thiazol-5-yl)methyl]phosphonate (1.35 g, 5.39 mmol, 44.7% yield) as white crystals. (ES$^+$) m/z: 250.96 (M+H)$^+$.

EXAMPLES

Example 1

Ethyl ({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetate

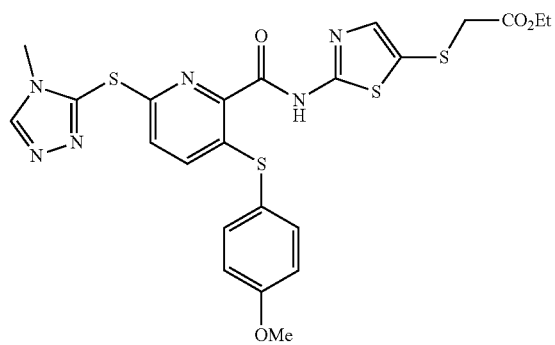 [SMILES: CCOC(=O)CSc1cnc(NC(=O)c2nc(Sc3nncn3C)ccc2Sc2ccc(OC)cc2)s1]

Method A

Step 1

Preparation of tert-butyl 6-chloro-3-fluoropyridine-2-carboxylate

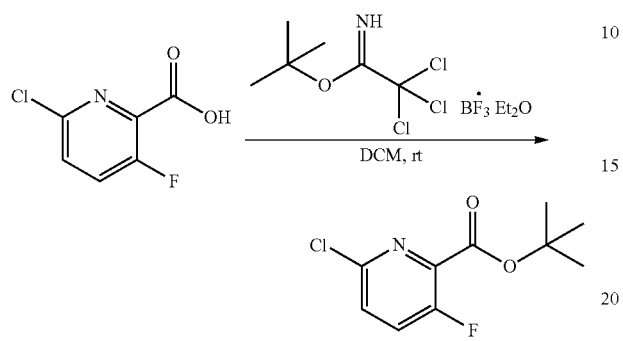

The suspension of 6-chloro-3-fluoropyridine-2-carboxylic acid (3.51 g, 20.0 mmol) and tert-butyl 2,2,2-trichloroacetimidate (7.16 mL, 40.0 mmol) in anhydrous DCM (80 mL) was added $BF_3$ etherate (0.507 mL, 4.0 mmol) at ambient temperature. After stirred vigorously for 36 h, The suspension was diluted with diethyl ether and washed with sodium carbonate (100 mL×2) and brine (100 mL). The organic layer was dried over sodium sulfate and concentrated in vacuo. The residue was purified by flash column chromatography (Biotage Flash 40 M) eluting gradually with 10-50% ethyl acetate to afford the title compound as a colorless oil (3.27 g, 71%).

Step 2

Preparation of tert-butyl 6-chloro-3[(4-methoxyphenyl)sulfanyl]pyridine-2-carboxylate

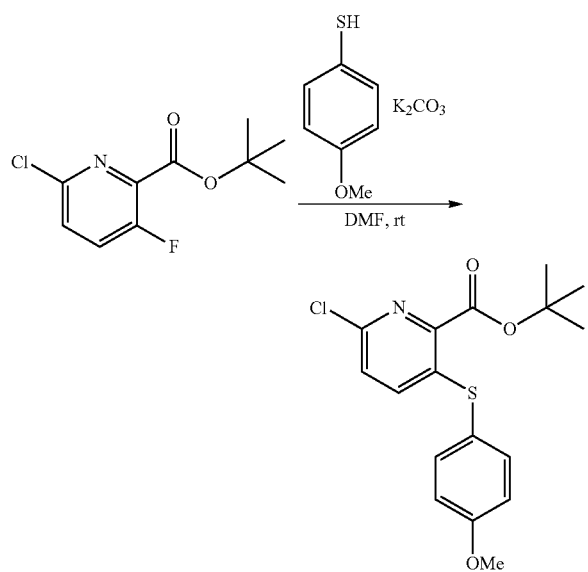

tert-Butyl 6-chloro-3-fluoropyridine-2-carboxylate (3.20 g, 13.81 mmol), potassium carbonate (2.10 g, 15.20 mmol), and 4-methoxythiophenol (1.937 g, 13.81 mmol) were stirred in anhydrous DMF (40 mL) at ambient temperature for 12 h. The mixture was diluted with water (50 mL) and extracted with ethyl acetate three times (50 mL×3). The combined organic layers were washed with water three times (20 mL×3), then with brine once. The organic layer was separated, dried over sodium sulfate, filtrated and concentrated in vacuo. The residue was purified by Biotage (Flash 40M) gradually eluted with 10-40% EtOAc/Hexane to afford the title compound as white crystals (3.63 g, 75%). $^1$HNMR (500 MHz, $CDCl_3$) δ (ppm)=7.49 (dd, J=6.6, 2.1 Hz, 2H), 7.15 (d, J=8.5 Hz, 1H), 7.08 (d, J=8.6 Hz, 1H), 7.00 (dd, J=6.7, 2.1 Hz, 2H), 3.89 (s, 3H), 1.71 (s, 9H).

Step 3

Preparation of tert-butyl 3-[(4-methoxyphenyl)sulfanyl]-6-[(4-methyl-4H-1,2,4-triazol-3-yl)sulfanyl]pyridine-2-carboxylate

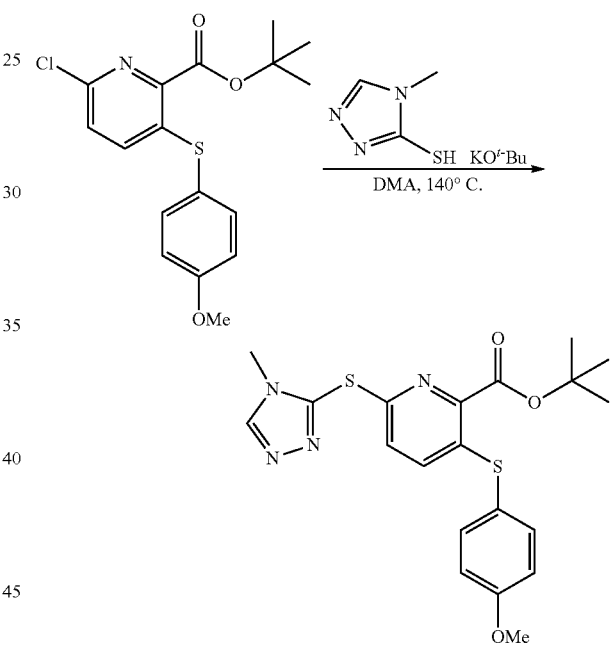

To a clean dry 50 mL flask was charged with a magnetic stirring bar and potassium tert-butoxide (0.58 g, 5.17 mmol) and 4-methyl-4H-1,2,4-triazole-3-thiol (0.638 g, 5.54 mmol). It was sealed and purged with nitrogen. To the solids was added anhydrous DMA (5 mL). It was stirred at 100° C. until the solids completely dissolved. A solution of tert-butyl 6-chloro-3-[(4-methoxyphenyl)sulfanyl]pyridine-2-carboxylate in hot DMA (5 mL, about 100° C.) under nitrogen was transferred to the reaction flask by a syringe and the reaction mixture was stirred in an oil bath at 140° C. for 6 h. It was cooled to rt and diluted with water (50 mL). The aqueous solution was extracted with DCM (50 mL×4). The combined organic layers were washed with sodium carbonate twice and brine once, dried over sodium sulfate, filtrated and concentrated in vacuo. The residue was purified by Biotage (Flash 40M) gradually eluted with 0-6% MeOH in DCM to give the title compound as a yellow solid (1.36 g, 85%). $^1$HNMR (500 MHz, $CDCl_3$) δ (ppm)=8.37 (s, 1H), 7.50-7.42 (m, 2H), 7.11 (d, J=8.5 Hz, 1H), 7.06-6.95 (m, 3H), 3.89 (s, 3H), 3.85 (s, 3H), 1.64 (s, 9H).

Step 4

Preparation of 3-[(4-methoxyphenyl)sulfanyl]-6-[(4-methyl-4H-1,2,4-triazol-3-yl)sulfanyl]pyridine-2-carboxylic acid

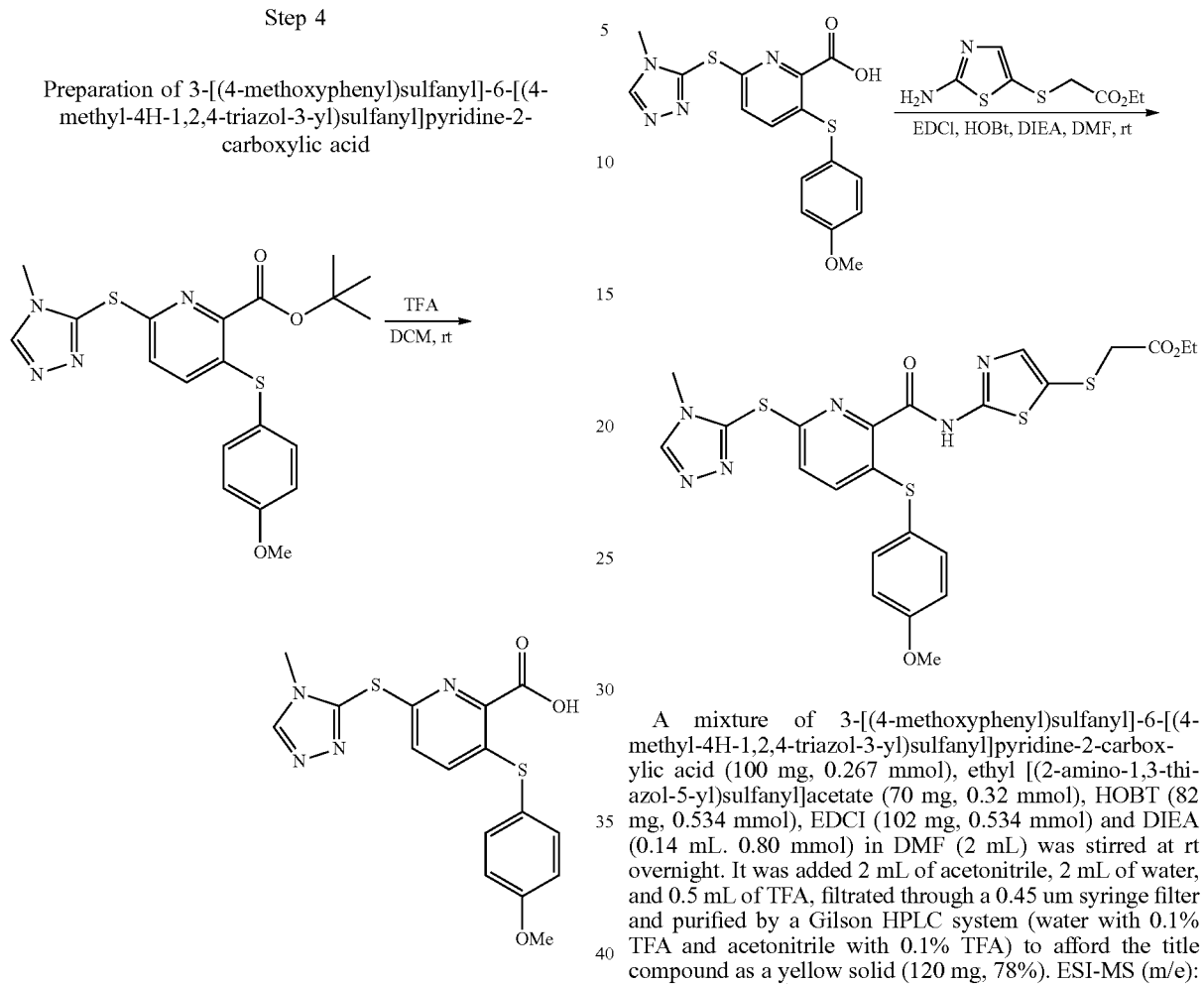

The solution of tert-butyl 3-[(4-methoxyphenyl)sulfanyl]-6-[(4-methyl-4H-1,2,4-triazol-3-yl)sulfanyl]pyridine-2-carboxylate in wet DCM (8 mL) was added TFA (2 mL) stirring for 2 h at rt. Most solvent was removed in vacuo and the residue was purified by Biotage (Flash 25 M) gradually eluted with 100% DCM to 85:7.5:7.5 DCM:MeOH:AcOH to give the title product as an off-white solid (810 mg, 68.5%). $^1$HNMR (500 MHz, methanol-$d_4$) δ (ppm)=8.72 (s, 1H), 7.47 (d, J=8.3 Hz, 2H), 7.11 (s, 2H), 7.05 (d, J=8.3 Hz, 2H), 3.86 (s, 3H), 3.79 (s, 3H).

Step 5

A mixture of 3-[(4-methoxyphenyl)sulfanyl]-6-[(4-methyl-4H-1,2,4-triazol-3-yl)sulfanyl]pyridine-2-carboxylic acid (100 mg, 0.267 mmol), ethyl [(2-amino-1,3-thiazol-5-yl)sulfanyl]acetate (70 mg, 0.32 mmol), HOBT (82 mg, 0.534 mmol), EDCI (102 mg, 0.534 mmol) and DIEA (0.14 mL. 0.80 mmol) in DMF (2 mL) was stirred at rt overnight. It was added 2 mL of acetonitrile, 2 mL of water, and 0.5 mL of TFA, filtrated through a 0.45 um syringe filter and purified by a Gilson HPLC system (water with 0.1% TFA and acetonitrile with 0.1% TFA) to afford the title compound as a yellow solid (120 mg, 78%). ESI-MS (m/e): 575.0 [M+H]$^+$; $^1$HNMR (500 MHz, CDCl$_3$) δ (ppm)=8.81 (s, 1H), 7.66 (s, 1H), 7.49 (m, 2H), 7.37 (d, J=8.5 Hz, 1H), 7.15 (d, J=8.5 Hz, 1H), 7.04 (m, 2H), 4.25 (q, J=7.0 Hz, 2H), 3.90 (s, 3H), 3.86 (s, 3H), 3.54 (s, 2H), 1.32 (t, J=7.0 Hz, 3H).

Example 2

({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetic acid

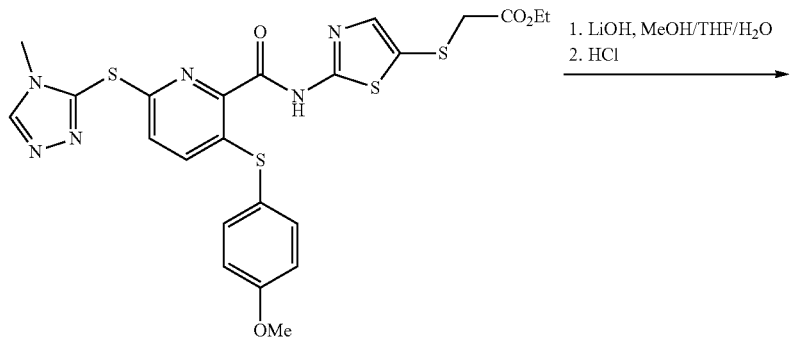

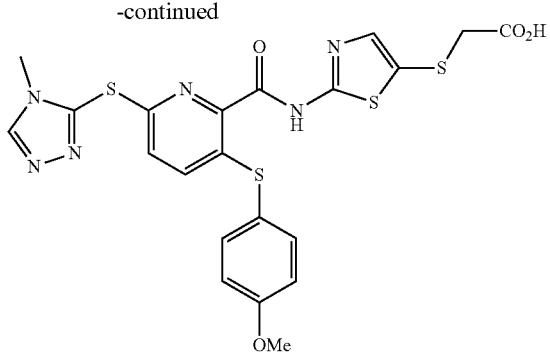

A solution of ethyl ({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetate (120 mg, 0.209 mmol) in methanol (1 mL) and THF (1 mL) was added an aqueous solution of lithium hydroxide (2 N, 1 mL). The reaction mixture was stirred at rt for 1 h and an aqueous solution of HCl (1 N, 2.5 mL) was added. Yellow solids were precipitated. The suspension was stirred for 30 min and the solid was filtrated, rinsed with water (5 mL), then DCM (1 mL). It was collected and dried under vacuum to afford the title compound (80 mg, 70%). ESI-MS (m/e): 547.1 [M+H]⁺.

Example 3

3-[(4-methoxyphenyl)sulfanyl]-N-(5-{[2-(methyl-amino)-2-oxoethyl]sulfanyl}-1,3-thiazol-2-yl)-6-[(4-methyl-4H-1,2,4-triazol-3-yl)sulfanyl]pyridine-2-carboxamide

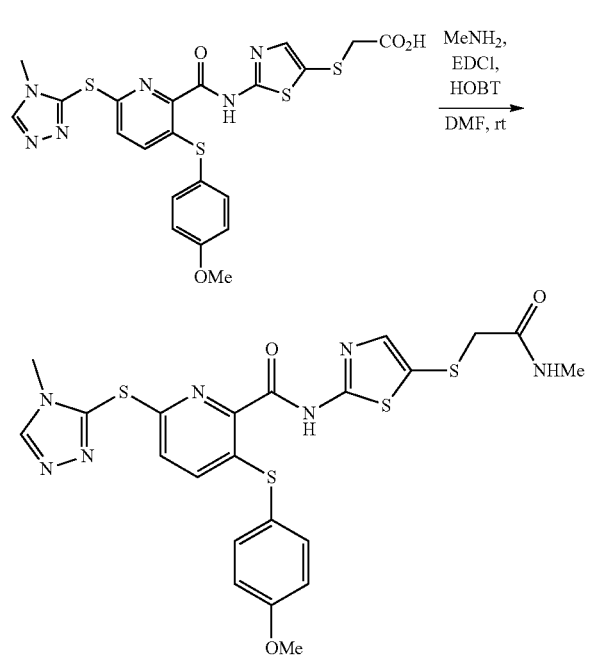

A mixture of ({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetic acid (25 mg, 0.046 mmol), methylamine (2 M in THF, 0.12 mL, 0.24 mmol), HOBT (12.36 mg, 0.091 mmol), EDCI (17.53 mg, 0.091 mmol) in DMF (0.5 mL) was stirred at rt for three days. Yellow precipitations were formed. The reaction mixture was diluted with ethyl acetate (2 mL) and water (2 mL), then it was added 4 drops of 1 M HCl by a glass pipette. The mixture was shaken for a few times and filtrated. The solid was washed in sequence with water (1 mL×2), ethyl acetate (1 mL×2), methanol (0.5 mL×2) then ether (1 mL×2). It was collected and dried over vacuum to give 15 mg of the title compound. The filtrate was purified by HPLC to give 9 mg of the title compound. The combined yield was 24 mg (94%). ESI-MS (m/e): 560.1 [M+H]⁺; ¹HNMR (500 MHz, DMSO-d₆) δ (ppm)=12.0 (s, 1H), 8.83 (s, 1H), 8.02-7.92 (m, 1H), 7.61 (s, 1H), 7.48 (m, 2H), 7.07 (m, 2H), 3.80 (s, 3H), 3.62 (s, 3H), 3.44 (s, 2H), 2.59 (d, J=4.7 Hz, 3H).

Example 4

2-({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)-2-methylpropanoic acid

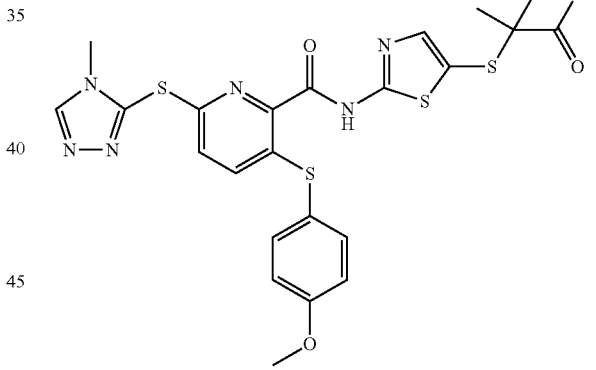

Method B

Step 1

Preparation of ethyl 2-[(2-{[(6-chloro-3-fluoropyridin-2-yl)carbonyl]amino}-1,3-thiazol-5-yl)sulfanyl]-2-methylpropanoate

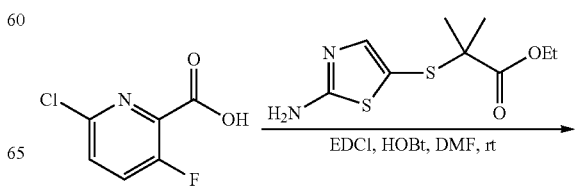

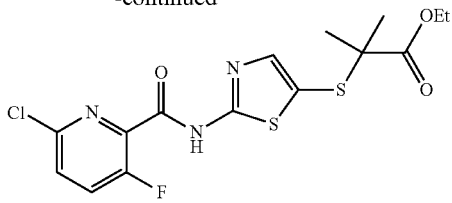

A mixture of 6-chloro-3-fluoropyridine-2-carboxylic acid (314 mg, 1.786 mmol), ethyl 2-[(2-amino-1,3-thiazol-5-yl)sulfanyl]-2-methylpropanoate (400 mg, 1.624 mmol), HOBT (219 mg, 1.624 mmol), EDCI (311 mg, 1.624 mmol) in DMF (5 mL) was stirred at rt overnight. The reaction mixture was partitioned between water and diethyl ether/ethyl acetate (1/1). The aqueous layer was extracted with ether for 3 times and the combined organic layers were washed with water three times and brine once. The organic layer was dried over sodium sulfate and concentrated. The residue was purified by flash column chromatography eluting gradually with 10% to 40% ethyl acetate in hexane to afford the title compound as a slight yellow solid (310 mg, 54%).

Step 2

Preparation of ethyl 2-({2-[({6-chloro-3-[(4-methoxyphenyl)sulfanyl]pyridin-2-yl}carbonyl)amino]-1,3-thiazol-5-yl}sulfanyl)-2-methylpropanoate

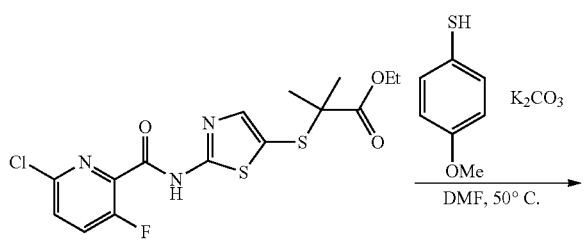

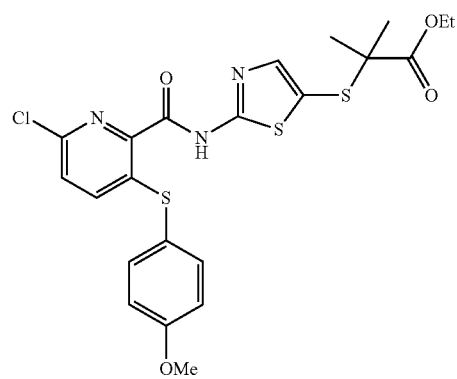

A mixture of ethyl 2-[(2-{[(6-chloro-3-fluoropyridin-2-yl)carbonyl]amino}-1,3-thiazol-5-yl)sulfanyl]-2-methylpropanoate (150 mg, 0.371 mmol), potassium carbonate (61.6 mg, 0.446 mmol), and 4-methoxythiophenol (62.5 mg, 0.446 mmol) were stirred in anhydrous DMF (2 mL) under nitrogen for 1.5 h at 50° C. It was cooled to rt and left for 12 h. The reaction mixture was diluted with water (20 mL) and extracted with ethyl acetate three times (20 mL×3). The combined organic layers were washed with water three times (20 mL×3), then with brine once. The organic layer was separated and dried over sodium sulfate. After concentration the residue was purified by flash column chromatography gradually eluting with 10-40% EtOAc/Hexane to afford the title compound as a yellow glass (195 mg, 100%).

Step 3

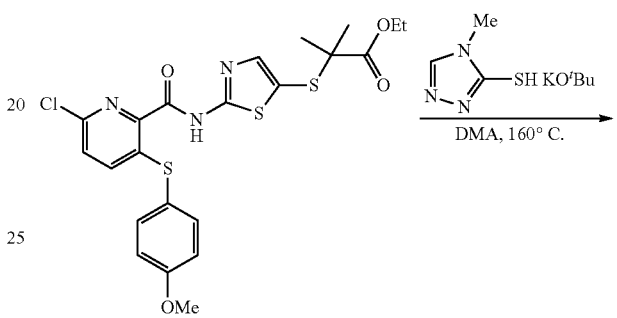

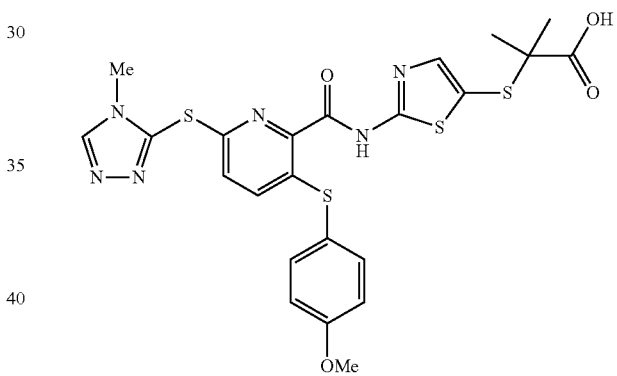

To a flask containing ethyl 2-({2-[({6-chloro-3-[(4-methoxyphenyl)sulfanyl]pyridin-2-yl}carbonyl)amino]-1,3-thiazol-5-yl}sulfanyl)-2-methylpropanoate (195 mg, 0.372 mmol) was added 4-methyl-4H-1,2,4-triazole-3-thiol 214 mg, 1.86 mmol), potassium carbonate (209 mg, 1.86 mmol), and anhydrous DMA (2 mL). It was sealed and purged with nitrogen. The suspension was heated to 160° C. with stirring to give a clear yellow solution. After 5 h, the flask was removed from the oil bath to allow it cooled to rt. The reaction mixture was added saturated aqueous ammonium chloride (2 mL) and 20 mL of water. The mixture was extracted with ethyl acetate (20 mL×2). The aqueous layer was acidified by 1 mL of 1 M HCl to pH 3. Chloroform was used (20 mL×3) to extract the product. The organic layers were combined and washed with brine, dried over sodium sulfate and concentrated in vacuo. LC-MS suggested a roughly equal amount of both ester and free acid were formed. The crude product was purified by Prep-TLC (1000 um) developed with 5% MeOH in DCM to give the title compound (10 mg, 4.7%). ESI-MS (m/e): 575.1 [M+H]$^+$.

Example 5

Ethyl 3-({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)-2,2-dimethylpropanoate

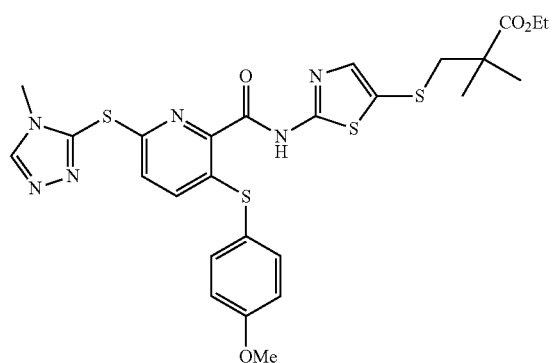 [SMILES: CCOC(=O)C(C)(C)CSc1cnc(NC(=O)c2nc(Sc3nncn3C)ccc2Sc2ccc(OC)cc2)s1]

In the same manner as in Example 1, the title compound (44 mg, 53%) was obtained as yellow solid from the amide coupling of 3-[(4-methoxyphenyl)sulfanyl]-6-[(4-methyl-4H-1,2,4-triazol-3-yl)sulfanyl]pyridine-2-carboxylic acid (50 mg, 0.134 mmol) and ethyl 3-[(2-amino-1,3-thiazol-5-yl)sulfanyl]-2,2-dimethylpropanoate (50 mg, 0.192 mmol) and purified by HPLC. ESI-MS (m/e): 617.2 [M+H]$^+$; $^1$HNMR (500 MHz, CDCl$_3$) δ (ppm)=8.84 (s, 1H), 7.55 (s, 1H), 7.51 (m, 2H), 7.39 (d, J=8.7 Hz, 1H), 7.16 (d, J=8.7 Hz, 1H), 7.05 (m, 2H), 4.19 (q, J=7.1 Hz, 2H), 3.91 (s, 3H), 3.88 (s, 3H), 3.17 (s, 2H), 1.36 (s, 6H), 1.32 (t, J=7.1 Hz, 3H).

Example 6

3-({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)-2,2-dimethylpropanoic acid

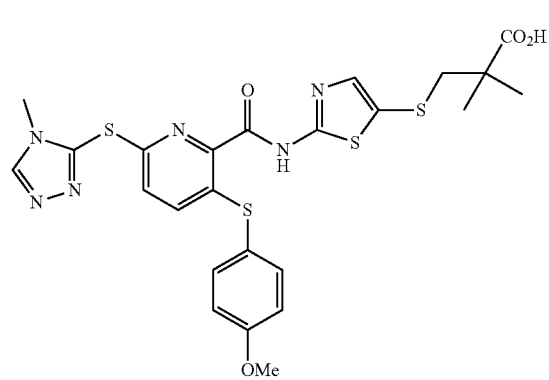 [SMILES: COc1ccc(Sc2ccc(Sc3nncn3C)nc2C(=O)Nc2ncc(SCC(C)(C)C(=O)O)s2)cc1]

In the same manner as in Example 2, the title compound (6.7 mg, 19%) was obtained as a white solid from the saponification of ethyl 3-({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)-2,2-dimethylpropanoate (37 mg, 0.060 mmol) by 1 M lithium hydroxide in methanol/water (1:1) at 80° C. overnight and purified by HPLC. ESI-MS (m/e): 589.0 [M+H]$^+$; $^1$HNMR (500 MHz, CDCl$_3$) δ (ppm)=8.56 (s, 1H), 7.51 (s, 1H), 7.33 (m, 2H), 7.06 (d, J=8.7 Hz, 1H), 7.00 (m, 2H), 6.88 (d, J=8.7 Hz, 1H), 4.01 (s, 3H), 3.91 (s, 3H), 3.21 (s, 2H), 1.46 (s, 6H).

Example 7

Methyl 3-{2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}propanoate

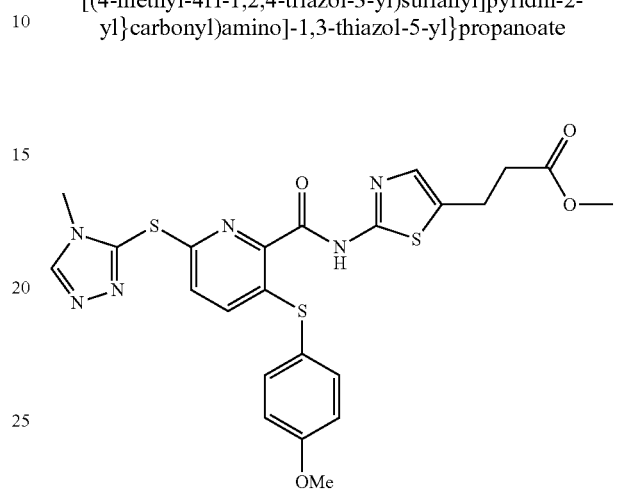

In the same manner as in Example 1, the title compound (33 mg, 76%) was obtained as yellow solid from the amide coupling of 3-[(4-methoxyphenyl)sulfanyl]-6-[(4-methyl-4H-1,2,4-triazol-3-yl)sulfanyl]pyridine-2-carboxylic acid (30.0 mg, 0.080 mmol) and 5-(3-methoxy-3-oxopropyl)-1,3-thiazol-2-aminium bromide (32.2 mg, 0.120 mmol) and purified by HPLC. ESI-MS (m/e): 543.1 [M+H]$^+$.

Example 8

3-{2-[({3-[(4-Methoxyphenyl)sulfanyl]-6-[(4-methyl-4H-1,2,4-triazol-3-yl)sulfanyl]pyridin-2-yl}carbonyl)amino]-1,3-thiazol-5-yl}propanoic acid

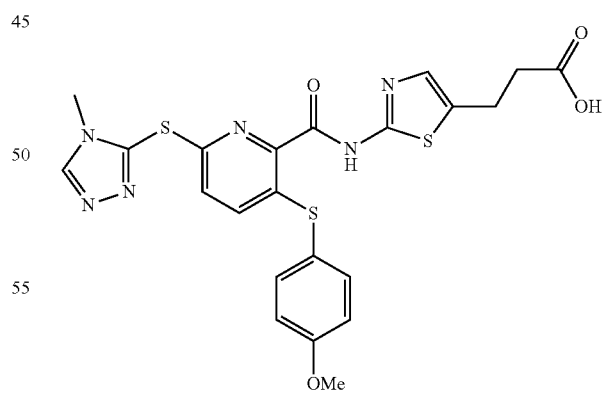

In the same manner as in Example 2, the title compound (20 mg, 79%) was obtained as a yellow solid from the saponification of methyl 3-{2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}propanoate (37 mg, 0.060 mmol), acidification and filtration. ESI-MS (m/e): 529.1 [M+H]$^+$.

Example 9

N-[4-(2-Amino-2-oxoethyl)phenyl]-3-[(4-methoxyphenyl)sulfanyl]-6-[(4-methyl-4H-1,2,4-triazol-3-yl)sulfanyl]pyridine-2-carboxamide

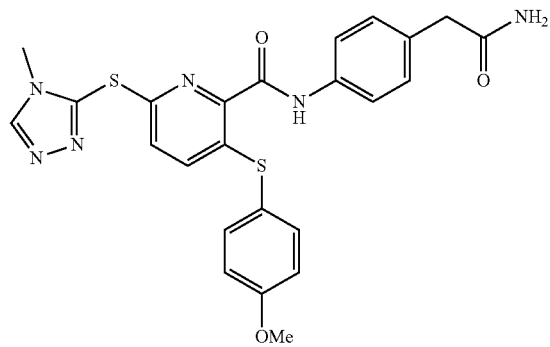 [SMILES: COc1ccc(Sc2ccc(Sc3nncn3C)nc2C(=O)Nc2ccc(CC(N)=O)cc2)cc1]

In the same manner as in Example 1, the title compound was obtained from the amide coupling of 3-[(4-methoxyphenyl)sulfanyl]-6-[(4-methyl-4H-1,2,4-triazol-3-yl)sulfanyl]pyridine-2-carboxylic acid and 2-(4-aminophenyl)acetamide and purified by HPLC. ESI-MS (m/e): 507.1 [M+H]$^+$;

Example 10

Ethyl ({2-[({3-[(4-methoxyphenyl)sulfanyl]-6-(pyridin-2-ylsulfanyl)pyridin-2-yl}carbonyl)amino]-1,3-thiazol-5-yl}sulfanyl)acetate

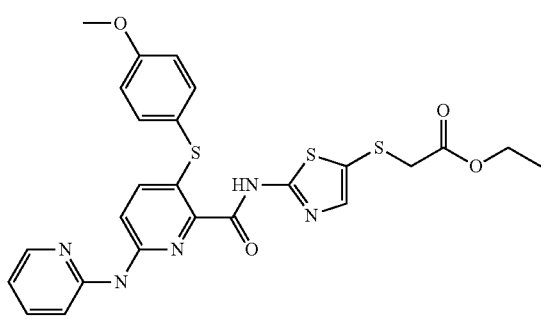 [SMILES: CCOC(=O)CSc1cnc(NC(=O)c2nc(Nc3ccccn3)ccc2Sc2ccc(OC)cc2)s1]

Method A

Step 1

Preparation of tert-butyl 3-[(4-methoxyphenyl)sulfanyl]-6-(pyridin-2-ylsulfanyl)pyridine-2-carboxylate

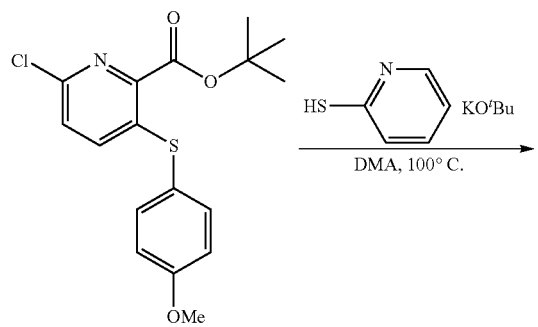

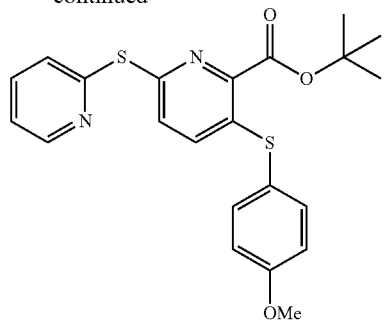

A solution of 2-mercaptopyridine (227 mg, 2.046 mmol) in 2 mL of DMI (dimethyl imidazolidilone) was added potassium tert-butoxide (214 mg, 1.910 mmol) and stirred for 10 min. The solution was slowly added to tert-butyl 6-chloro-3-[(4-methoxyphenyl)sulfanyl]pyridine-2-carboxylate (480 mg, 1.364 mmol) in 2 mL of DMI at 100° C. over 6 h and the mixture was heated for another 6 h. It was diluted with ethyl acetate (30 mL) and washed with water (30 mL×3) then brine, dried over sodium sulfate and concentrated. The residue was purified by Biotage (Flash 25M, 0-60% ethyl acetate in hexane) to give the title compound (580 mg, 1.360 mmol, 100% yield) as a colorless oil.

Step 2

Preparation of 3-[(4-methoxyphenyl)sulfanyl]-6-(pyridin-2-ylsulfanyl)pyridine-2-carboxylic acid

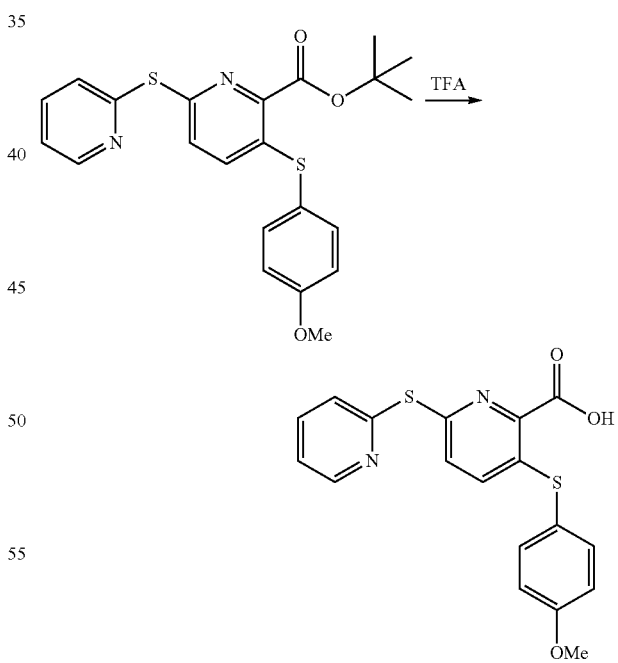

tert-Butyl 3-[(4-methoxyphenyl)sulfanyl]-6-(pyridin-2-ylsulfanyl)pyridine-2-carboxylate (580 mg, 1.360 mmol) in DCM (5 ml) was added TFA (5.00 ml) and stirred for 2 h at rt. It was concentrated and diluted with DCM, washed with brine three times. Dried over sodium sulfate and concentrated to give the title compound (462 mg, 1.247 mmol, 92% yield) as a yellow foam.

Step 3

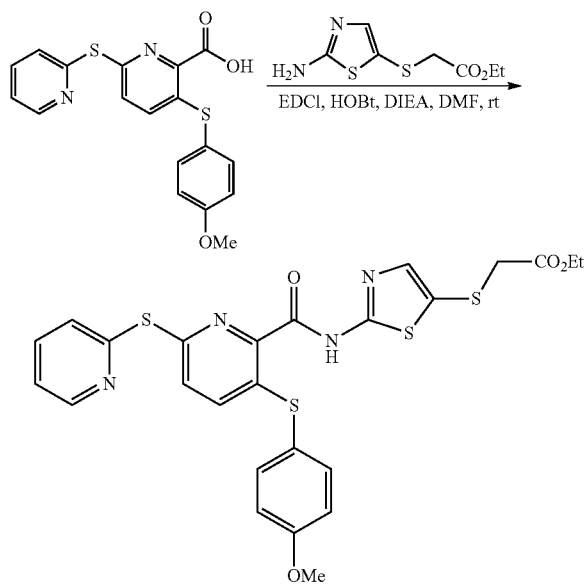

In the same manner as Example 1 Step 5, the title compound (85 mg, 0.149 mmol, 94%) as a pale white solid was obtained from the amide coupling of 3-[(4-methoxyphenyl)sulfanyl]-6-(pyridin-2-ylsulfanyl)pyridine-2-carboxylic acid (59.0 mg, 0.159 mmol) and ethyl [(2-amino-1,3-thiazol-5-yl)sulfanyl]acetate (45.2 mg, 0.207 mmol) and purified by filtration. ESI-MS (m/e): 570.8 [M+H]$^+$.

Example 11

({2-[({3-[(4-Methoxyphenyl)sulfanyl]-6-(pyridin-2-ylsulfanyl)pyridin-2-yl}carbonyl)amino]-1,3-thiazol-5-yl}sulfanyl)acetic acid

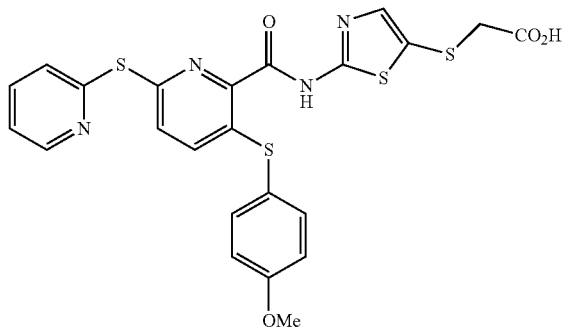 [SMILES: COc1ccc(Sc2ccc(Sc3ccccn3)nc2C(=O)Nc2ncc(SCC(=O)O)s2)cc1]

A solution of ethyl ({2-[({3-[(4-methoxyphenyl)sulfanyl]-6-(pyridin-2-ylsulfanyl)pyridin-2-yl}carbonyl)amino]-1,3-thiazol-5-yl}sulfanyl)acetate (80 mg, 0.140 mmol) in methanol (1 mL) and THF (1 mL) was added an aqueous solution of lithium hydroxide (2 N, 1 mL). The reaction mixture was stirred at rt for 1 h and an aqueous solution of HCl (1 N, 3 mL) was added. Off-white solids were precipitated. The suspension was stirred for 30 min and the solid was filtrated, rinsed with water (5 mL). It was collected and dried under vacuum to afford the title compound (61 mg, 80%) as a yellow solid. ESI-MS (m/e): 542.8 [M+H]$^+$.

Example 12

Ethyl {5-chloro-2-{[3-[(4-methoxyphenyl)sulfanyl]-6-(pyridin-2-ylsulfanyl)pyridin-2-yl}carbonyl)amino]-1,3-thiazol-4-yl}acetate

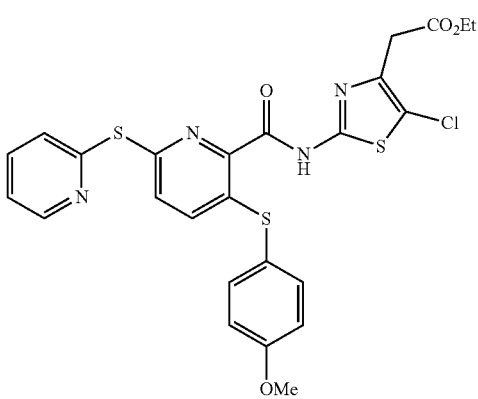 [SMILES: CCOC(=O)Cc1nc(NC(=O)c2nc(Sc3ccccn3)ccc2Sc2ccc(OC)cc2)sc1Cl]

In the same manner as in Example 10, the title compound (47.5 mg, 0.083 mmol, 61%) was obtained as yellow solid from the amide coupling of 3-[(4-methoxyphenyl)sulfanyl]-6-(pyridin-2-ylsulfanyl)pyridine-2-carboxylic acid (50 mg, 0.135 mmol) and ethyl (2-amino-5-chloro-1,3-thiazol-4-yl)acetate (38.7 mg, 0.175 mmol) and purified by HPLC. ESI-MS (m/e): 572.9 [M+H]$^+$.

Example 13

{5-Chloro-2-[({3-[(4-methoxyphenyl)sulfanyl]-6-(pyridin-2-ylsulfanyl)pyridin-2-yl}carbonyl)amino]-1,3-thiazol-4-yl}acetic acid

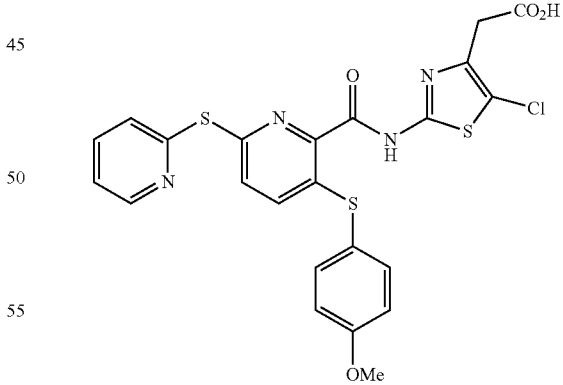

In the same manner as in Example 11, the title compound (28 mg, 74%) was obtained as an yellow solid from the saponification of ethyl ethyl {5-chloro-2-[({3-[(4-methoxyphenyl)sulfanyl]-6-(pyridin-2-ylsulfanyl)pyridin-2-yl}carbonyl)amino]-1,3-thiazol-4-yl}acetate (40 mg, 0.070 mmol) by 0.5 M lithium hydroxide in methanol/water/THF (2:1:1, 2 mL) at rt for 1 h, acidification by 1.5 mL of 1 N HCl and filtration. ESI-MS (m/e): 544.8 [M+H]$^+$.

Example 14

Methyl 3-{2-[({3-[(4-methoxyphenyl)sulfanyl]-6-(pyridin-2-ylsulfanyl)pyridin-2-yl}carbonyl)amino]-1,3-thiazol-5-yl}propanoate

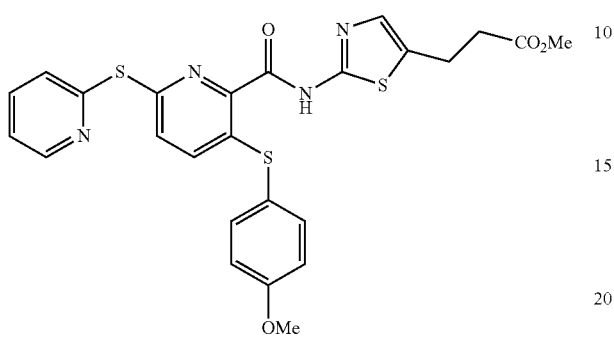

In the same manner as in Example 10, the title compound (65 mg, 0.121 mmol, 89%) was obtained as yellow solid from the amide coupling of 3-[(4-methoxyphenyl)sulfanyl]-6-(pyridin-2-ylsulfanyl)pyridine-2-carboxylic acid (50 mg, 0.135 mmol) and 5-(3-methoxy-3-oxopropyl)-1,3-thiazol-2-aminium bromide (50.5 mg, 0.189 mmol) and purified by HPLC. ESI-MS (m/e): 538.9 [M+H]$^+$.

Example 15

3-{2-[({3-[(4-Methoxyphenyl)sulfanyl]-6-(pyridin-2-ylsulfanyl)pyridin-2-yl}carbonyl)amino]-1,3-thiazol-5-yl}propanoic acid

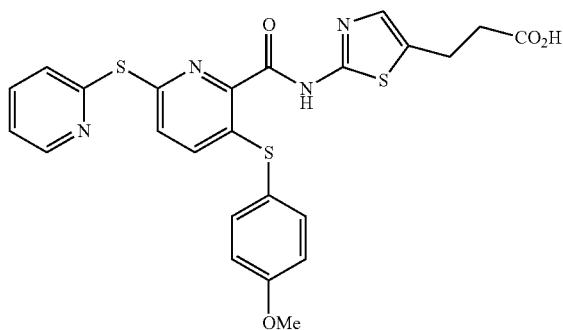 [SMILES: COc1ccc(Sc2ccc(Sc3ccccn3)nc2C(=O)Nc2ncc(CCC(=O)O)s2)cc1]

In the same manner as in Example 11, the title compound (50 mg, 86%) was obtained as an yellow solid from the saponification of methyl 3-{2-[({3-[(4-methoxyphenyl)sulfanyl]-6-(pyridin-2-ylsulfanyl)pyridin-2-yl}carbonyl)amino]-1,3-thiazol-5-yl}propanoate (60 mg, 0.111 mmol) by 0.67 M lithium hydroxide in methanol/water/THF (1:1:1, 1.5 mL) at rt for 1 h, acidification by 1.5 mL of 1 N HCl and filtration. ESI-MS (m/e): 524.9 [M+H]$^+$. $^1$HNMR (500 MHz, DMSO-d$_6$) δ (ppm)=12.2 (bs, 1H), 11.8 (s, 1H), 8.53 (m, 1H), 7.81 (td, J=7.9, 1.9 Hz, 1H), 7.58-7.48 (m, 4H), 7.34 (dd, J=7.5, 4.8 Hz, 1H), 7.12 (m, 3H), 6.95 (s, 1H), 3.83 (s, 3H), 2.89 (t, J=7.4 Hz, 2H), 2.64 (t, J=7.6 Hz, 2H).

Example 16

Ethyl {2-[({3-[(4-methoxyphenyl)sulfanyl]-6-(pyridin-2-ylsulfanyl)pyridin-2-yl}carbonyl)amino]-1,3-thiazol-4-yl}acetate

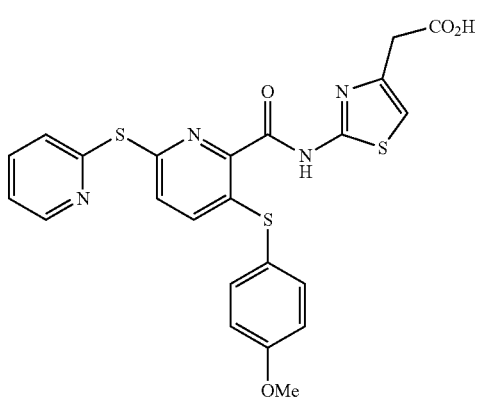 [SMILES: COc1ccc(Sc2ccc(Sc3ccccn3)nc2C(=O)Nc2nc(CC(=O)O)cs2)cc1]

In the same manner as in Example 10, 3-[(4-methoxyphenyl)sulfanyl]-6-(pyridin-2-ylsulfanyl)pyridine-2-carboxylic acid (50 mg, 0.135 mmol) and ethyl (2-amino-1,3-thiazol-4-yl)acetate (35.2 mg, 0.189 mmol) was coupled. The product was precipitated by the addition of 2 mL of water and 0.3 mL of TFA. The solid filtrated and washed with water/acetonitrile (10/1), then diethyl ether in sequence. It was dried under high vacuum to give the title compound (68 mg, 94%) as yellow solid. ESI-MS (m/e): 538.8 [M+H]$^+$.

Example 17

{2-[({3-[(4-Methoxyphenyl)sulfanyl]-6-(pyridin-2-ylsulfanyl)pyridin-2-yl}carbonyl)amino]-1,3-thiazol-4-yl}acetic acid In the same manner as in Example 11, the title compound (48 mg, 84%) was obtained as an yellow solid from the saponification of ethyl {2-[({3-[(4-methoxyphenyl)sulfanyl]-6-(pyridin-2-ylsulfanyl)pyridin-2-yl}carbonyl)amino]-1,3-thiazol-4-yl}acetate (60 mg, 0.111 mmol) by 0.67 M lithium hydroxide in methanol/water/THF (1:1:1, 1.5 mL) at rt for 1 h, acidification by 1.5 mL of 1 N HCl and filtration. ESI-MS (m/e): 510.8 [M+H]$^+$.

Example 18

Ethyl ({5-[({3-[(4-fluorophenyl)sulfanyl]-6-[(4-methyl-4H-1,2,4-triazol-3-yl)sulfanyl]pyridin-2-yl}carbonyl)amino]thiophen-2-yl}sulfanyl)acetate

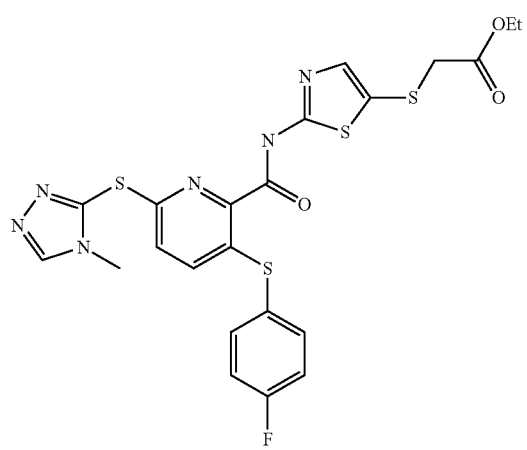 [SMILES: CCOC(=O)CSc1cnc(NC(=O)c2nc(Sc3nncn3C)ccc2Sc2ccc(F)cc2)s1]

Step 1

Preparation of tert-butyl 3,6-dichloropyridine-2-carboxylate

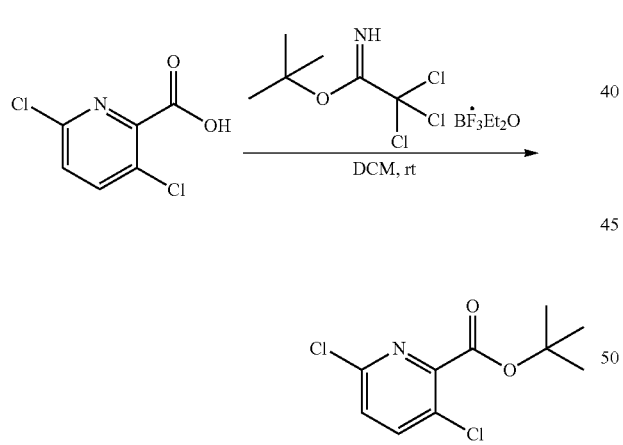

A solution of 3,6-dichloropyridine-2-carboxylic acid (25 g, 130 mmol) and tert-butyl 2,2,2-trichloroacetimidate (25 ml, 140 mmol) in DCM (200 ml) was added BF$_3$.OEt$_2$ (1 mL, 7.89 mmol) and the mixture was stirred for 2 d. TLC showed that starting material ("SM") remained. One more equiv of -butyl 2,2,2-trichloroacetimidate (25 ml, 140 mmol) was added stirring for 2 d. TLC showed the completion of the reaction. To the mixture was added 2 mL of TEA. The mixture was filtrated through Celite and the filtrate was washed with sodium bicarbonate, then brine. Dried over sodium sulfate and concentrated. The residue was purified by Biotage (Flash 65M, 0-30% ethyl acetate in hexane with 2% TEA) to give the title compound (31.0 g, 125 mmol, 96% yield) as white crystals.

Step 2

Preparation of tert-butyl 6-chloro-3[(4-fluorophenyl)sulfanyl]pyridine-2-carboxylate

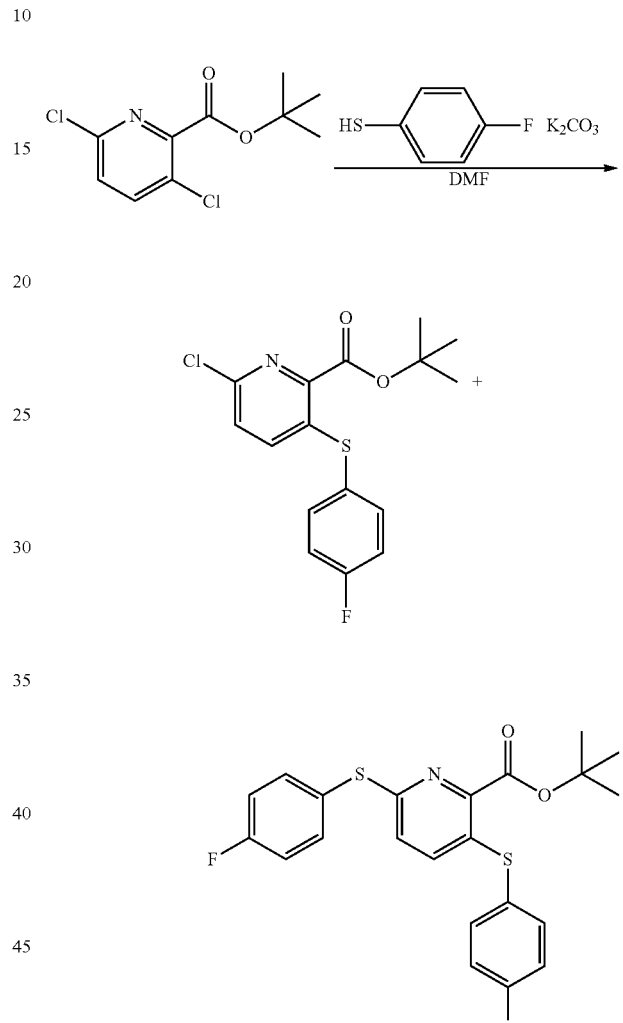

The suspension of potassium carbonate (4.27 g, 30.9 mmol), 4-fluorothiophenol (3.29 ml, 30.9 mmol) and tert-butyl 3,6-dichloropyridine-2-carboxylate (5.11 g, 20.60 mmol) in DMF (20 ml) was stirred overnight at rt. TLC showed significant amount of starting material left. The reaction mixture was heated at 50° C. for 1 h. It was diluted with 200 mL of water and extracted with diethyl ether twice. The combined organic layers were washed with water five times (100 mL) and brine once. It was dried over sodium sulfate and concentrated. The residue was purified by Biotage (Flash 65M, 0-30% ethyl acetate in hexane) to afford tert-butyl 6-chloro-3-[(4-fluorophenyl)sulfanyl]pyridine-2-carboxylate (2.53 g, 7.45 mmol, 36.1% yield) as white crystals and tert-butyl 3,6-bis[(4-fluorophenyl)sulfanyl]pyridine-2-carboxylate (4.30 g, 9.96 mmol, 48.4% yield) as white crystals.

Step 3

Preparation of tert-butyl 3-[(4-fluorophenyl)sulfanyl]-6-[(4-methyl-4H-1,2,4-triazol-3-yl)sulfanyl]pyridine-2-carboxylate

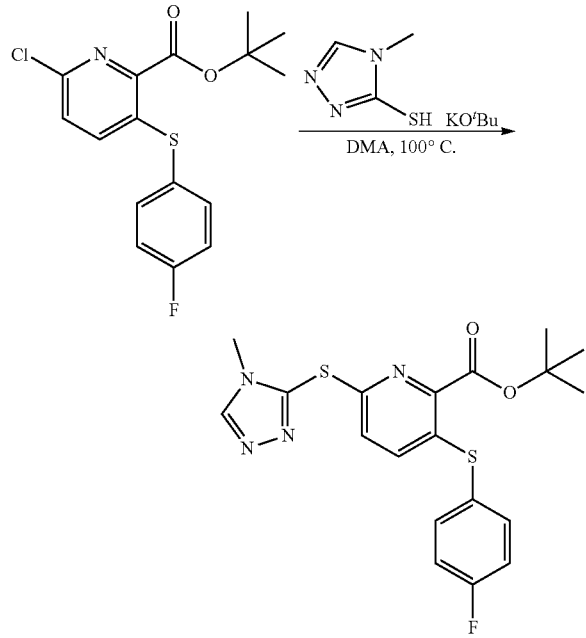

A solution of 3-mercapto-4-methyl-4H-1,2,4-triazole (136 mg, 1.177 mmol) in 2.5 mL of DMI was added potassium tert-Butoxide (132 mg, 1.177 mmol) stirring for 20 min. The solution was slowly added to a solution of tert-butyl 6-chloro-3-[(4-fluorophenyl)sulfanyl]pyridine-2-carboxylate (200 mg, 0.589 mmol) in 2.5 mL of DMI at 100° C. by a syringe pump over 6 h. It was heated for another 6 h after the addition. The reaction mixture was cooled to rt, diluted with 50 mL of water, extracted with ethyl acetate twice. The organic layers were washed with water three times and brine once, dried over sodium sulfate, filtrated and concentrated in vacuo. The residue was purified by Biotage (ethyl acetate) to give the title compound (224 mg, 0.535 mmol, 91% yield) as a pale white solid.

Step 4

Preparation of 3-[(4-fluorophenyl)sulfanyl]-6-[(4-methyl-4H-1,2,4-triazol-3-yl)sulfanyl]pyridine-2-carboxylic acid

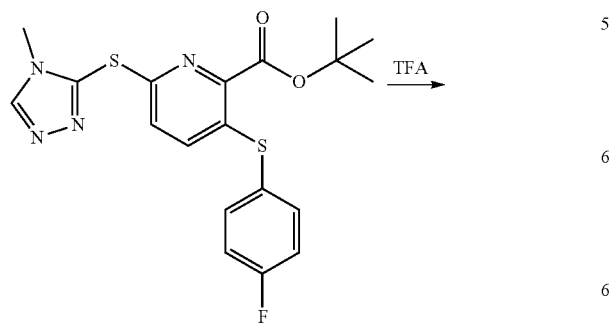

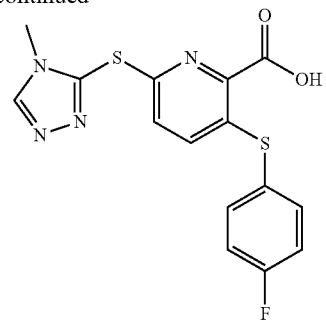

A solution of tert-butyl 3-[(4-fluorophenyl)sulfanyl]-6-[(4-methyl-4H-1,2,4-triazol-3-yl)sulfanyl]pyridine-2-carboxylate (210 mg, 0.502 mmol) in DCM (4 ml) was added TFA (2 mL) at 0° C. The reaction was warmed to rt and stirred for 1 h. It was concentrated in vacuo and diluted with 20 mL DCM. It was washed with brine once. The organic layer was dried over sodium sulfate, filtrated and concentrated in vacuo. The solid was triturated in diethyl ether and filtrated to give the title compound (168 mg, 0.464 mmol, 92% yield) as a white solid.

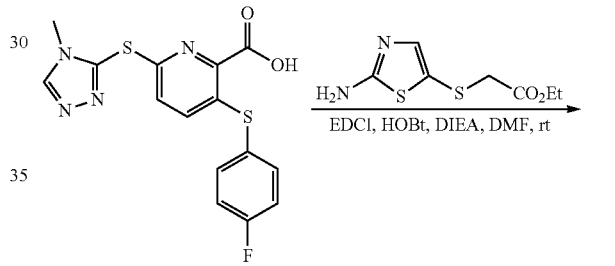

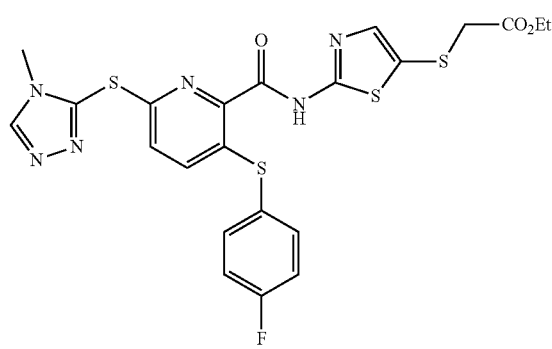

Step 5

In the same manner as Example 1 Step 5, the title compound (63 mg, 0.112 mmol, 68%) as a yellow solid was obtained from the amide coupling of 3-[(4-fluorophenyl)sulfanyl]-6-[(4-methyl-4H-1,2,4-triazol-3-yl)sulfanyl]pyridine-2-carboxylic acid (60.0 mg, 0.166 mmol) and ethyl [(2-amino-1,3-thiazol-5-yl)sulfanyl]acetate (47.0 mg, 0.215 mmol) and purified by HPLC. ESI-MS (m/e): 562.9 [M+H]$^+$.

Example 19

({2-[({3-[(4-Fluorophenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetic acid

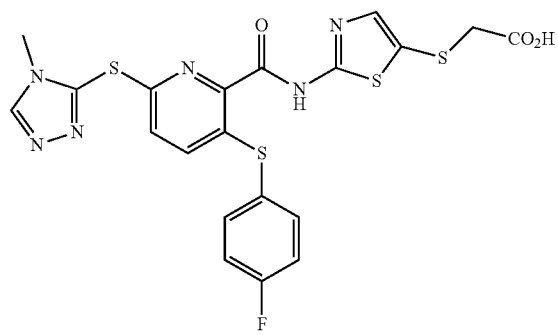 [SMILES: Cn1cnnc1Sc1ccc(Sc2ccc(F)cc2)c(C(=O)Nc2ncc(SCC(=O)O)s2)n1]

A solution of ethyl ({5-[({3-[(4-fluorophenyl)sulfanyl]-6-[(4-methyl-4H-1,2,4-triazol-3-yl)sulfanyl]pyridin-2-yl}carbonyl)amino]thiophen-2-yl}sulfanyl)acetate (58 mg, 0.103 mmol) in methanol (1 mL) and THF (1 mL) was added an aqueous solution of lithium hydroxide (2 N, 1 mL). The reaction mixture was stirred at rt for 1 h and an aqueous solution of HCl (1 N, 3 mL) was added. Yellow solids were precipitated. The suspension was stirred for 30 min and the solid was filtrated, rinsed with water (5 mL). It was collected and dried under vacuum to afford the title compound (47.6 mg, 86%) as a yellow solid. ESI-MS (m/e): 535.1 [M+H]$^+$.

Example 20

Ethyl 3-({5-[({3-[(4-fluorophenyl)sulfanyl]-6-[(4-methyl-4H-1,2,4-triazol-3-yl)sulfanyl]pyridin-2-yl}carbonyl)amino]thiophen-2-yl}sulfanyl)-2,2-dimethylpropanoate

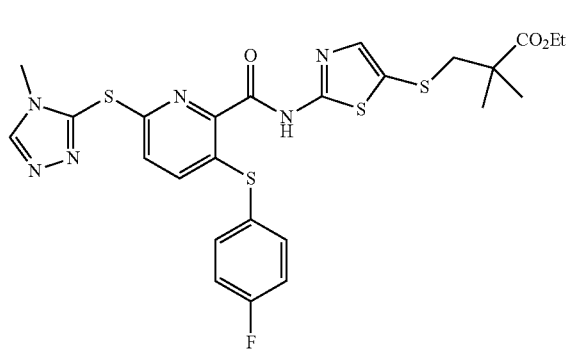 [SMILES: CCOC(=O)C(C)(C)CSc1cnc(NC(=O)c2nc(Sc3nncn3C)ccc2Sc2ccc(F)cc2)s1]

In the same manner as in Example 1, the title compound (62 mg, 0.103 mmol, 62%) was obtained as yellow solid from the amide coupling of 3-[(4-fluorophenyl)sulfanyl]-6-[(4-methyl-4H-1,2,4-triazol-3-yl)sulfanyl]pyridine-2-carboxylic acid (60.0 mg, 0.166 mmol) and ethyl 3-[(2-amino-1,3-thiazol-5-yl)sulfanyl]-2,2-dimethylpropanoate (56 mg, 0.215 mmol) and purified by HPLC. ESI-MS (m/e): 605.0 [M+H]$^+$.

Example 21

3-({2-[({3-[(4-Fluorophenyl)sulfanyl]-6-[(4-methyl-4H-1,2,4-triazol-3-yl)sulfanyl]pyridin-2-yl}carbonyl)amino]-1,3-thiazol-5-yl}sulfanyl)-2,2-dimethylpropanoic acid

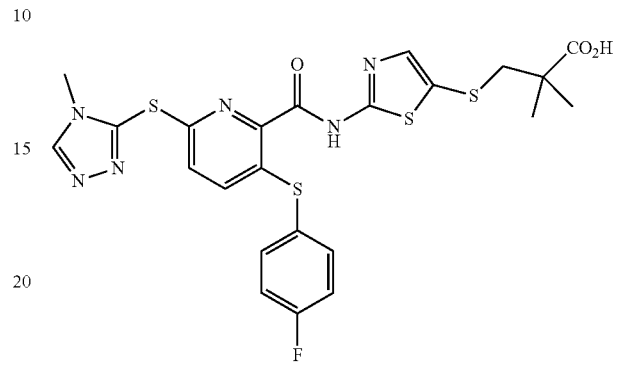

In the same manner as in Example 2, the title compound (37 mg, 72%) was obtained as a white solid from the saponification of ethyl ethyl 3-({5-[({3-[(4-fluorophenyl)sulfanyl]-6-[(4-methyl-4H-1,2,4-triazol-3-yl)sulfanyl]pyridin-2-yl}carbonyl)amino]thiophen-2-yl}sulfanyl)-2,2-dimethylpropanoate (54 mg, 0.089 mmol) by 0.67 M lithium hydroxide in methanol/water/THF (1:1:1) at 70° C. for 1 h and purified by HPLC. ESI-MS (m/e): 576.8 [M+H]$^+$.

Example 22

Ethyl {2-[({3-[(4-fluorophenyl)sulfanyl]-6-[(4-methyl-4H-1,2,4-triazol-3-yl)sulfanyl]pyridin-2-yl}carbonyl)amino]-1,3-thiazol-5-yl}acetate

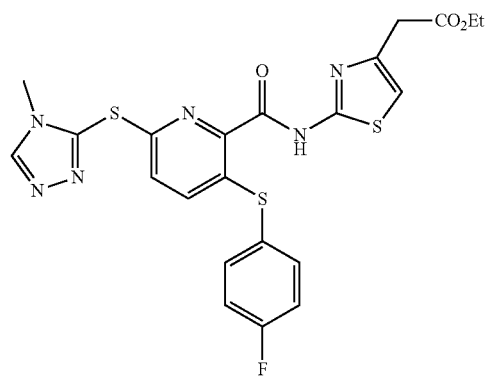 [SMILES: CCOC(=O)Cc1csc(NC(=O)c2nc(Sc3nncn3C)ccc2Sc2ccc(F)cc2)n1]

In the same manner as in Example 1, the title compound (31 mg, 0.058 mmol, 76%) was obtained as a yellow solid from the amide coupling of 3-[(4-fluorophenyl)sulfanyl]-6-[(4-methyl-4H-1,2,4-triazol-3-yl)sulfanyl]pyridine-2-carboxylic acid (28.0 mg, 0.077 mmol) and ethyl (2-amino-1,3-thiazol-4-yl)acetate (18.7 mg, 0.100 mmol) and purified by HPLC. ESI-MS (m/e): 531.0 [1\4+H]$^+$.

Example 23

{2-[({3-[(4-Fluorophenyl)sulfanyl]-6-[(4-methyl-4H-1,2,4-triazol-3-yl)sulfanyl]pyridin-2-yl}carbonyl)amino]-1,3-thiazol-5-yl}acetic acid

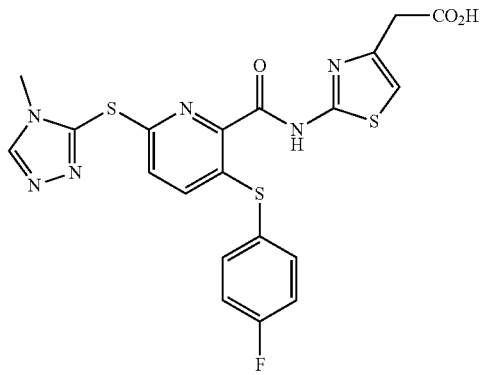 [SMILES: Cn1cnnc1Sc1ccc(Sc2ccc(F)cc2)c(C(=O)Nc2nc(CC(=O)O)cs2)n1]

In the same manner as in Example 11, the title compound (23 mg, 93%) was obtained as an off-white solid from the saponification of ethyl {2-[({3-[(4-fluorophenyl)sulfanyl]-6-[(4-methyl-4H-1,2,4-triazol-3-yl)sulfanyl]pyridin-2-yl}carbonyl)amino]-1,3-thiazol-5-yl}acetate (26 mg, 0.049 mmol) by 0.67 M lithium hydroxide in methanol/water/THF (1:1:1, 1.5 mL) at rt for 1 h, acidification by 1.5 mL of 1 N HCl and filtration. ESI-MS (m/e): 502.8 [1\4+H]+.

Example 24

Ethyl {5-chloro-2-[({3-[(4-fluorophenyl)sulfanyl]-6-[(4-methyl-4H-1,2,4-triazol-3-yl)sulfanyl]pyridin-2-yl}carbonyl)amino]-1,3-thiazol-4-yl}acetate

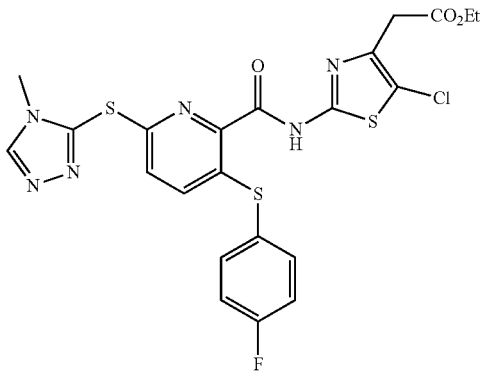 [SMILES: CCOC(=O)Cc1nc(NC(=O)c2nc(Sc3nncn3C)ccc2Sc2ccc(F)cc2)sc1Cl]

In the same manner as in Example 1, the title compound (27.6 mg, 30%) was obtained as a yellow solid from the amide coupling of 3-[(4-fluorophenyl)sulfanyl]-6-[(4-methyl-4H-1,2,4-triazol-3-yl)sulfanyl]pyridine-2-carboxylic acid (60.0 mg, 0.166 mmol) and ethyl (2-amino-5-chloro-1,3-thiazol-4-yl)acetate (47.5 mg, 0.215 mmol) and purified by HPLC. ESI-MS (m/e): 564.8 [M+H]+.

Example 25

{5-Chloro-2-[({3-[(4-fluorophenyl)sulfanyl]-6-[(4-methyl-4H-1,2,4-triazol-3-yl)sulfanyl]pyridin-2-yl}carbonyl)amino]-1,3-thiazol-4-yl}acetic acid

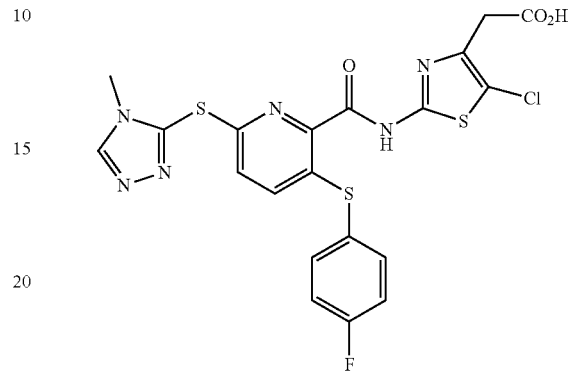

In the same manner as in Example 11, the title compound (19.3 mg, 81%) was obtained as a slight yellow solid from the saponification of ethyl {5-chloro-2-[({3-[(4-fluorophenyl)sulfanyl]-6-[(4-methyl-4H-1,2,4-triazol-3-yl)sulfanyl]pyridin-2-yl}carbonyl)amino]-1,3-thiazol-4-yl}acetate (25 mg, 0.044 mmol) by 0.1 M lithium hydroxide in methanol/water/THF (1:1:1, 2 mL) at rt for 1 h, acidification by 3 mL of 1 N HCl and filtration. ESI-MS (m/e): 536.7 [M+H]+.

Example 26

Diethyl ({2-[({3-[(4-fluorophenyl)sulfanyl]-6-[(4-methyl-4H-1,2,4-triazol-3-yl)sulfanyl]pyridin-2-yl}carbonyl)amino]-1,3-thiazol-5-yl}methyl)phosphonate

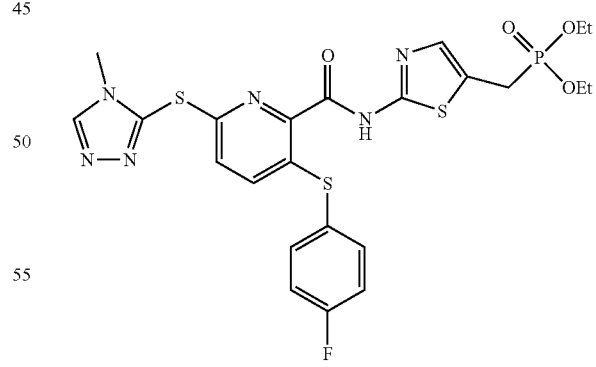

In the same manner as in Example 1, the title compound (57.4 mg, 87%) was obtained as a white solid from the amide coupling of 3-[(4-fluorophenyl)sulfanyl]-6-[(4-methyl-4H-1,2,4-triazol-3-yl)sulfanyl]pyridine-2-carboxylic acid (40.0 mg, 0.110 mmol) and ethyl (2-amino-5-chloro-1,3-thiazol-4-yl)acetate (30.4 mg, 0.121 mmol) and purified by filtration. ESI-MS (m/e): 594.8 [1\4+H]+.

Example 27

Ethyl ({5-[({3,6-bis[(4-fluorophenyl)sulfanyl]pyridin-2-yl}carbonyl)amino]thiophen-2-yl}sulfanyl)acetate

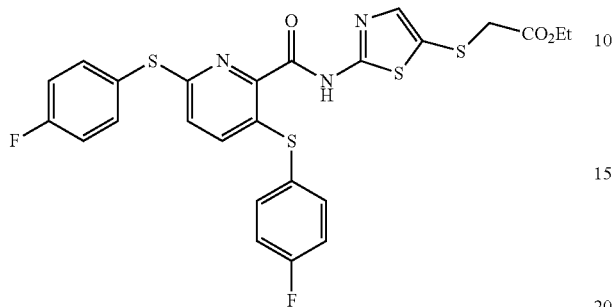

Step 1

A solution of tert-butyl 3,6-bis[(4-fluorophenyl)sulfanyl] pyridine-2-carboxylate (4.38 g, 10.15 mmol) in DCM (40 ml) and TFA (20 ml) was stirred for 6 h at rt. TLC showed the completion of the reaction. Solvents were removed in vacuo. The yellow residue was purified by Biotage (Flash 65M, 0-10% DCM:methanol/acetic acid (1/1)). The fractions were concentrated to give a white solid, which was triturated in 30 mL of diethyl ether and filtrated, rinsed with diethyl ether to give 3,6-bis[(4-fluorophenyl)sulfanyl]pyridine-2-carboxylic acid (2.4 g, 6.39 mmol, 63.0% yield) as a yellow solid.

Step 2

In the same manner as in Example 1, the title compound (56 mg, 64%) was obtained as a pale yellow solid from the amide coupling of 3,6-bis[(4-fluorophenyl)sulfanyl]pyridine-2-carboxylic acid (57.0 mg, 0.152 mmol) and ethyl [(2-amino-1,3-thiazol-5-yl)sulfanyl]acetate (33.1 mg, 0.152 mmol) and purified by filtration. ESI-MS (m/e): 576.0 [H+H]$^+$.

Example 28

({2-[({3,6-Bis[(4-fluorophenyl)sulfanyl]pyridin-2-yl}carbonyl)amino]-1,3-thiazol-5-yl}sulfanyl)acetic acid

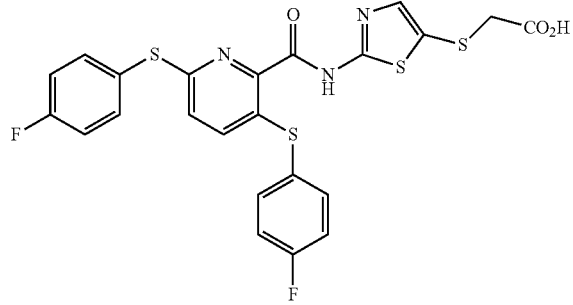 [SMILES: O=C(O)CSc1cnc(NC(=O)c2nc(Sc3ccc(F)cc3)ccc2Sc2ccc(F)cc2)s1]

In the same manner as in Example 11, the title compound (49 mg, 99%) was obtained as a slight yellow solid from the saponification of ethyl ({5-[({3,6-bis[(4-fluorophenyl)sulfanyl]pyridin-2-yl}carbonyl)amino]thiophen-2-yl}sulfanyl)acetate (52 mg, 0.090 mmol) by 0.67 M lithium hydroxide in methanol/water/THF (1:1:1, 3 mL) at rt for 1 h, acidification by 2.5 mL of 1 N HCl and filtration. ESI-MS (m/e): 548.0 [M±H]$^+$.

Example 29

Ethyl {2-[({3,6-bis[(4-fluorophenyl)sulfanyl]pyridin-2-yl}carbonyl)amino]-5-chloro-1,3-thiazol-4-yl}acetate

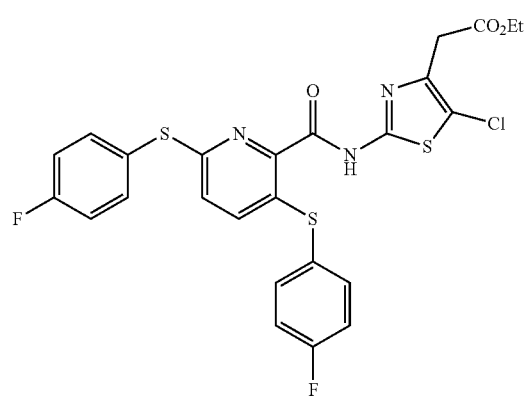 [SMILES: CCOC(=O)Cc1nc(NC(=O)c2nc(Sc3ccc(F)cc3)ccc2Sc2ccc(F)cc2)sc1Cl]

In the same manner as in Example 1, the title compound (74 mg, 80%) was obtained as a pale yellow solid from the amide coupling of 3,6-bis[(4-fluorophenyl)sulfanyl]pyridine-2-carboxylic acid (60.0 mg, 0.160 mmol) and ethyl (2-amino-5-chloro-1,3-thiazol-4-yl)acetate (49.4 mg, 0.224 mmol) and purified by HLPC. ESI-MS (m/e): 577. [M±H]$^+$.

Example 30

{2-[({3,6-Bis[(4-fluorophenyl)sulfanyl]pyridin-2-yl}carbonyl)amino]-5-chloro-1,3-thiazol-4-yl}acetic acid

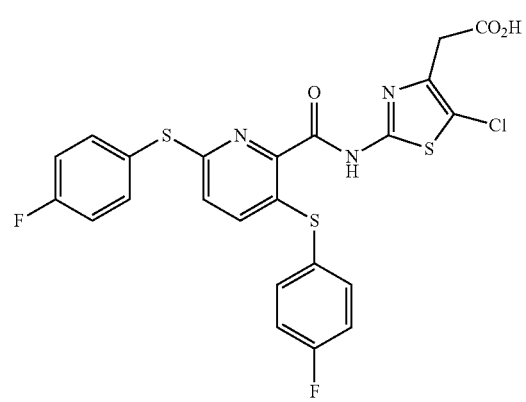 [SMILES: O=C(O)Cc1nc(NC(=O)c2nc(Sc3ccc(F)cc3)ccc2Sc2ccc(F)cc2)sc1Cl]

In the same manner as in Example 11, the title compound (60 mg, 94%) was obtained as a slight yellow solid from the saponification of ethyl 12-[({3,6-bis[(4-fluorophenyl)sulfanyl]pyridin-2-yl}carbonyl)amino]-5-chloro-1,3-thiazol-4-yl}acetate (67 mg, 0.116 mmol) by 0.67 M lithium hydroxide in methanol/water/THF (1:1:1, 3 mL) at rt for 1 h, acidification by 2.5 mL of 1 N HCl and filtration. ESI-MS (m/e): 549.8 [M+H]+.

Example 31

Ethyl {5-chloro-2-[({3-[(4-fluorophenyl)sulfanyl]-6-(pyridin-2-ylsulfanyl)pyridin-2-yl}carbonyl)amino]-1,3-thiazol-4-yl}acetate

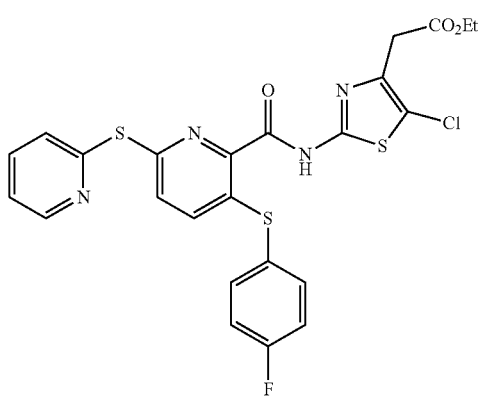 [SMILES: CCOC(=O)Cc1nc(NC(=O)c2nc(Sc3ccccn3)ccc2Sc2ccc(F)cc2)sc1Cl]

In the same manner as in Example 10, the title compound (56.5 mg, 72%) was obtained as a pale yellow solid from the amide coupling of 3-[(4-fluorophenyl)sulfanyl]-6-(pyridin-2-ylsulfanyl)pyridine-2-carboxylic acid (50.0 mg, 0.140 mmol) and ethyl (2-amino-5-chloro-1,3-thiazol-4-yl)acetate (43.1 mg, 0.195 mmol) and purified by HLPC. ESI-MS (m/e): 560.8 [M+H]+.

Example 32

{5-Chloro-2-[({3-[(4-fluorophenyl)sulfanyl]-6-(pyridin-2-ylsulfanyl)pyridin-2-yl}carbonyl)amino]-1,3-thiazol-4-yl}acetic acid

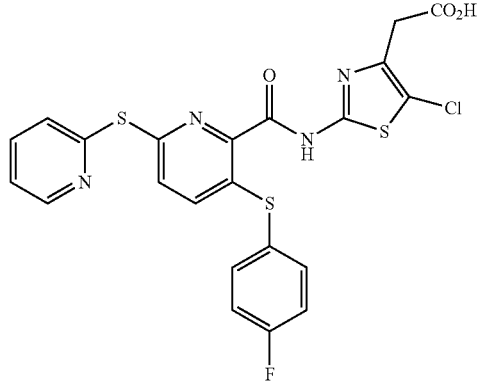 [SMILES: O=C(O)Cc1nc(NC(=O)c2nc(Sc3ccccn3)ccc2Sc2ccc(F)cc2)sc1Cl]

In the same manner as in Example 11, the title compound (60 mg, 94%) was obtained as a yellow solid from the saponification of ethyl {2-[({3,6-bis[(4-fluorophenyl)sulfanyl]pyridin-2-yl}carbonyl)amino]-5-chloro-1,3-thiazol-4-yl}acetate (67 mg, 0.116 mmol) by 0.67 M lithium hydroxide in methanol/water/THF (1:1:1, 3 mL) at rt for 1 h, acidification by 2.5 mL of 1 N HCl and filtration. ESI-MS (m/e): 532.7 [M+H]+.

Example 33

Ethyl {2-[({3-[(4-fluorophenyl)sulfanyl]-6-(pyridin-2-ylsulfanyl)pyridin-2-yl}carbonyl)amino]-1,3-thiazol-4-yl}acetate

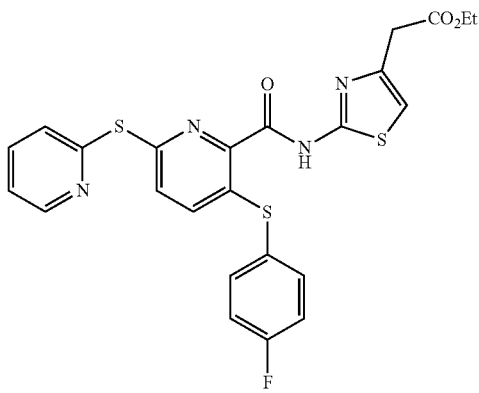 [SMILES: CCOC(=O)Cc1csc(NC(=O)c2nc(Sc3ccccn3)ccc2Sc2ccc(F)cc2)n1]

In the same manner as in Example 10, the title compound (40 mg, 68%) was obtained as a pale yellow solid from the amide coupling of 3-[(4-fluorophenyl)sulfanyl]-6-(pyridin-2-ylsulfanyl)pyridine-2-carboxylic acid (40.0 mg, 0.112 mmol) and ethyl (2-amino-1,3-thiazol-4-yl)acetate (29.1 mg, 0.156 mmol) and purified by HLPC. ESI-MS (m/e): 526.9 [M+H]+.

Example 34

{2-[({3-[(4-Fluorophenyl)sulfanyl]-6-(pyridin-2-ylsulfanyl)pyridin-2-yl}carbonyl)amino]-1,3-thiazol-4-yl}acetic acid

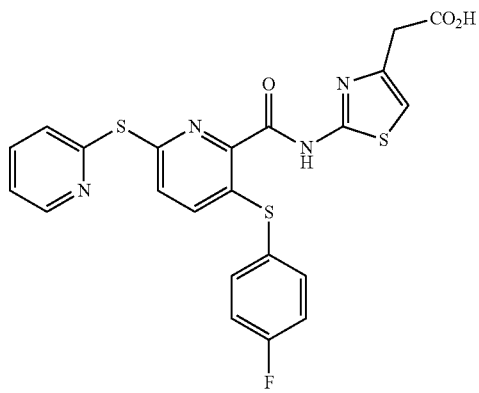 [SMILES: O=C(O)Cc1csc(NC(=O)c2nc(Sc3ccccn3)ccc2Sc2ccc(F)cc2)n1]

In the same manner as in Example 11, the title compound (21 mg, 65%) was obtained as a yellow solid from the saponification of ethyl {2-[({3-[(4-fluorophenyl)sulfanyl]-6-(pyridin-2-ylsulfanyl)pyridin-2-yl}carbonyl)amino]-1,3-thiazol-4-yl}acetate (34 mg, 0.065 mmol) by 1 M lithium hydroxide in water/THF (1:1, 2 mL) at rt for 1 h, acidification by 2.5 mL of 1 N HCl and filtration. ESI-MS (m/e): 498.8 [M+H]+.

Example 35

Ethyl ({2-[({3-[(4-fluorophenyl)sulfanyl]-6-(pyridin-2-ylsulfanyl)pyridin-2-yl}carbonyl)amino]-1,3-thiazol-5-yl}sulfanyl)acetate

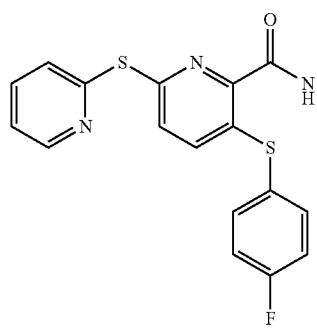

In the same manner as in Example 10, the title compound (45 mg, 72%) was obtained as a pale yellow solid from the amide coupling of 3-[(4-fluorophenyl)sulfanyl]-6-(pyridin-2-ylsulfanyl)pyridine-2-carboxylic acid (40.0 mg, 0.112 mmol) and ethyl [(2-amino-1,3-thiazol-5-yl)sulfanyl]acetate (34.1 mg, 0.156 mmol) and purified by HLPC. ESI-MS (m/e): 558.8 [M+H]+.

Example 36

({2-[({3-[(4-Fluorophenyl)sulfanyl]-6-(pyridin-2-ylsulfanyl)pyridin-2-yl}carbonyl)amino]-1,3-thiazol-5-yl}sulfanyl)acetic acid

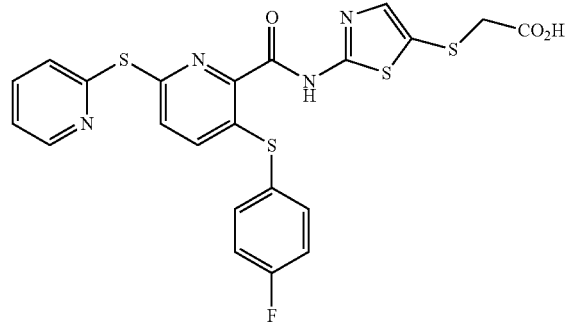 [SMILES: O=C(O)CSc1cnc(NC(=O)c2nc(Sc3ccccn3)ccc2Sc2ccc(F)cc2)s1]

In the same manner as in Example 11, the title compound (38 mg, 100%) was obtained as a yellow solid from the saponification of ethyl ({2-[({3-[(4-fluorophenyl)sulfanyl]-6-(pyridin-2-ylsulfanyl)pyridin-2-yl}carbonyl)amino]-1,3-thiazol-5-yl}sulfanyl)acetate (40 mg, 0.072 mmol) by 0.67 M lithium hydroxide in MeOH/water/THF (1:1:1, 1.5 mL) at rt for 1 h, acidification by 2.5 mL of 1 N HCl and filtration. ESI-MS (m/e): 530.8 [M+H]+.

Example 37

Ethyl 3-({2-[({3-[(4-fluorophenyl)sulfanyl]-6-(pyridin-2-ylsulfanyl)pyridin-2-yl}carbonyl)amino]-1,3-thiazol-5-yl}sulfanyl)-2,2-dimethylpropanoate

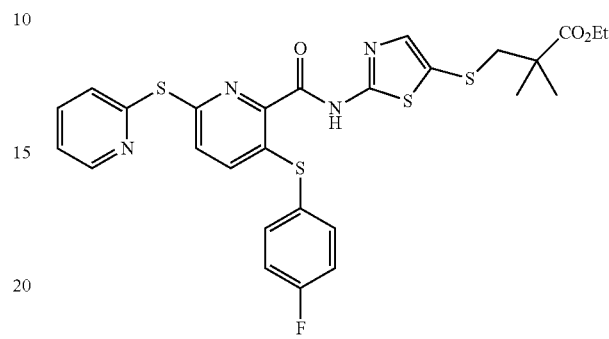

In the same manner as in Example 10, the title compound (45 mg, 67%) was obtained as a pale yellow solid from the amide coupling of 3-[(4-fluorophenyl)sulfanyl]-6-(pyridin-2-ylsulfanyl)pyridine-2-carboxylic acid (40.0 mg, 0.112 mmol) and ethyl 3-[(2-amino-1,3-thiazol-5-yl)sulfanyl]-2,2-dimethylpropanoate (40.7 mg, 0.156 mmol) and purified by HLPC. ESI-MS (m/e): 600.9 [M+H]+.

Example 38

3-({2-[({3-[(4-Fluorophenyl)sulfanyl]-6-(pyridin-2-ylsulfanyl)pyridin-2-yl}carbonyl)amino]-1,3-thiazol-5-yl}sulfanyl)-2,2-dimethylpropanoic acid

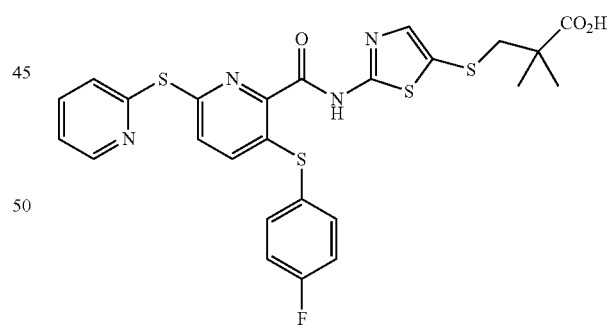

In the same manner as in Example 2, the title compound (26 mg, 72%) was obtained as a yellow solid from the saponification of ethyl 3-({2-[({3-[(4-fluorophenyl)sulfanyl]-6-(pyridin-2-ylsulfanyl)pyridin-2-yl}carbonyl)amino]-1,3-thiazol-5-yl}sulfanyl)-2,2-dimethylpropanoate (38 mg, 0.063 mmol) by 0.67 M lithium hydroxide in MeOH/water/THF (1:1:1, 1.5 mL) at 50° C. for 2 h, acidification by 2.5 mL of 1 N HCl and purification by HPLC. ESI-MS (m/e): 572.9 [M+H]+.

Example 39

Methyl 3-{2-[({3-[(4-fluorophenyl)sulfanyl]-6-(pyridin-2-ylsulfanyl)pyridin-2-yl}carbonyl)amino]-1,3-thiazol-5-yl}propanoate

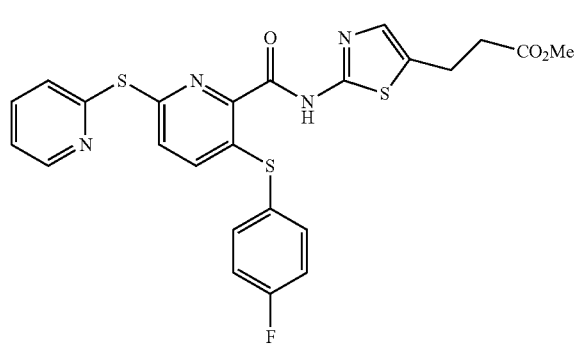 [SMILES: COC(=O)CCc1cnc(NC(=O)c2nc(Sc3ccccn3)ccc2Sc2ccc(F)cc2)s1]

In the same manner as in Example 10, the title compound (54 mg, 92%) was obtained as a pale yellow solid from the amide coupling of 3-[(4-fluorophenyl)sulfanyl]-6-(pyridin-2-ylsulfanyl)pyridine-2-carboxylic acid (40.0 mg, 0.112 mmol) and 5-(3-methoxy-3-oxopropyl)-1,3-thiazol-2-aminium bromide (29.8 mg, 0.112 mmol) and purified by HLPC. ESI-MS (m/e): 526.9 [M+H]$^+$.

Example 40

3-{2[({3-[(4-Fluorophenyl)sulfanyl]-6-(pyridin-2-ylsulfanyl)pyridin-2-yl}carbonyl)amino]-1,3-thiazol-5-yl}propanoic acid

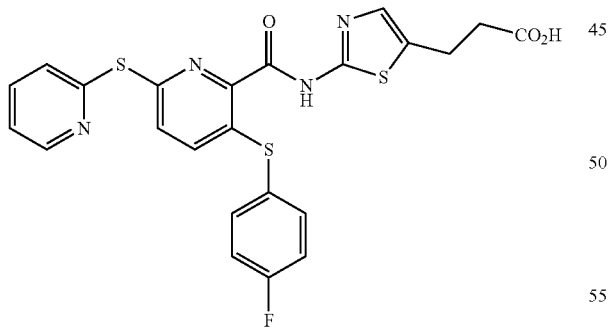

In the same manner as in Example 2, the title compound (31 mg, 66%) was obtained as a yellow solid from the saponification of methyl 3-{2-[({3-[(4-fluorophenyl)sulfanyl]-6-(pyridin-2-ylsulfanyl)pyridin-2-yl}carbonyl)amino]-1,3-thiazol-5-yl}propanoate (48 mg, 0.091 mmol) by 0.67 M lithium hydroxide in MeOH/water/THF (1:1:1, 1.5 mL) at rt for 1 h, acidification by 2.5 mL of 1 N HCl and purification by HPLC. ESI-MS (m/e): 512.8 [M+H]$^+$.

Example 41

Ethyl (5-chloro-2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-4-yl)acetate

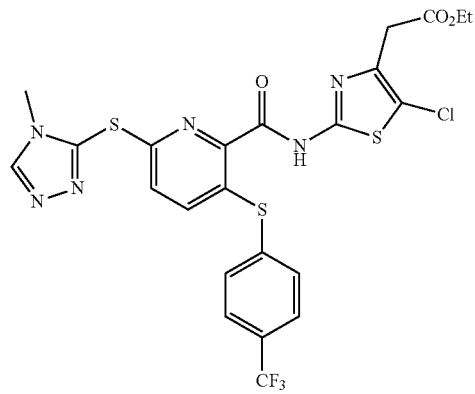 [SMILES: CCOC(=O)Cc1nc(NC(=O)c2nc(Sc3nncn3C)ccc2Sc2ccc(C(F)(F)F)cc2)sc1Cl]

In the same manner as in Example 1, the title compound (31 mg, 52%) was obtained as a yellow solid from the amide coupling of 6[(4-methyl-4H-1,2,4-triazol-3-yl)sulfanyl]-3-{[4-(trifluoromethyl)phenyl]sulfanyl}pyridine-2-carboxylic acid (40.0 mg, 0.097 mmol) and ethyl (2-amino-5-chloro-1,3-thiazol-4-yl)acetate (32 mg, 0.145 mmol) and purified by HLPC. ESI-MS (m/e): 614.8 [M+H]$^+$.

Example 42

(5-Chloro-2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-4-yl)acetic acid

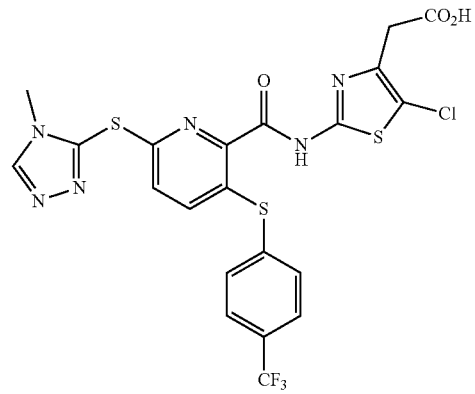 [SMILES: Cn1cnnc1Sc1ccc(Sc2ccc(C(F)(F)F)cc2)c(C(=O)Nc2nc(CC(=O)O)c(Cl)s2)n1]

In the same manner as in Example 11, the title compound (22.6 mg, 62%) was obtained as a yellow solid from the saponification of ethyl (5-chloro-2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-4-yl)acetate (29 mg, 0.047 mmol) by 1 M lithium hydroxide in MeOH/water (1:1, 1 mL) at rt for 1 h, acidification by 1.5 mL of 1 N HCl and filtration. ESI-MS (m/e): 587.1 [M+H]$^+$.

Example 43

Ethyl [(2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)sulfanyl]acetate

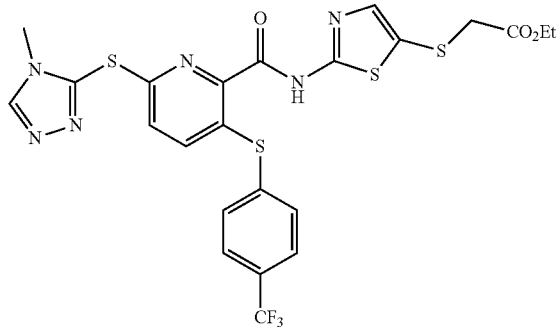 [SMILES: CCOC(=O)CSc1cnc(NC(=O)c2nc(Sc3nncn3C)ccc2Sc2ccc(C(F)(F)F)cc2)s1]

In the same manner as in Example 1, the title compound (41.8 mg, 70.3%) was obtained as a yellow solid from the amide coupling of 6-[(4-methyl-4H-1,2,4-triazol-3-yl)sulfanyl]-3-{[4-(trifluoromethyl)phenyl]sulfanyl}pyridine-2-carboxylic acid (40.0 mg, 0.097 mmol) and ethyl [(2-amino-1,3-thiazol-5-yl)sulfanyl]acetate (27.5 mg, 0.126 mmol) and purified by HLPC. ESI-MS (m/e): 612.8 [M+H]$^+$.

Example 44

[(2-{[(6-[(4-Methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)sulfanyl]acetic acid

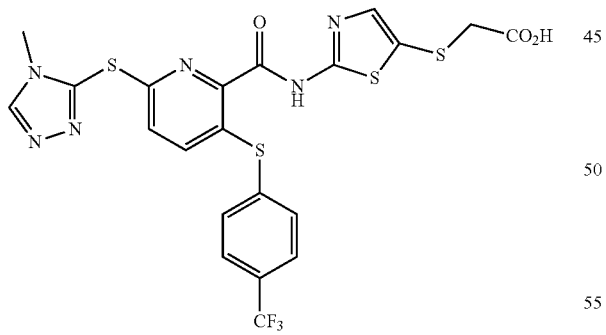

In the same manner as in Example 11, the title compound (32 mg, 88%) was obtained as a yellow solid from the saponification of ethyl [(2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)sulfanyl]acetate (38 mg, 0.062 mmol) by 1 M lithium hydroxide in MeOH/water (1:1, 1 mL) at rt for 1 h, acidification by 1.5 mL of 1 N HCl and filtration. ESI-MS (m/e): 585.1 [M+H]$^+$.

Example 45

Diethyl [(2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)methyl]phosphonate

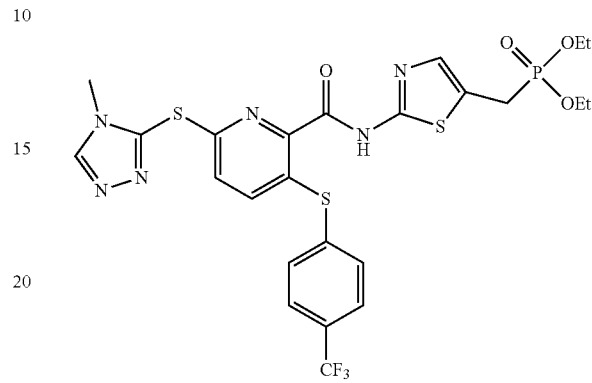

In the same manner as in Example 1, the title compound (53 mg, 85%) was obtained as a yellow solid from the amide coupling of 6-[(4-methyl-4H-1,2,4-triazol-3-yl)sulfanyl]-3-{[4-(trifluoromethyl)phenyl]sulfanyl}pyridine-2-carboxylic acid (40.0 mg, 0.097 mmol) and diethyl [(2-amino-1,3-thiazol-5-yl)methyl]phosphonate (26.7 mg, 0.107 mmol) and purified by HLPC. ESI-MS (m/e): 644.8 [M+H]$^+$.

Example 46

Ethyl (2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-4-yl)acetate

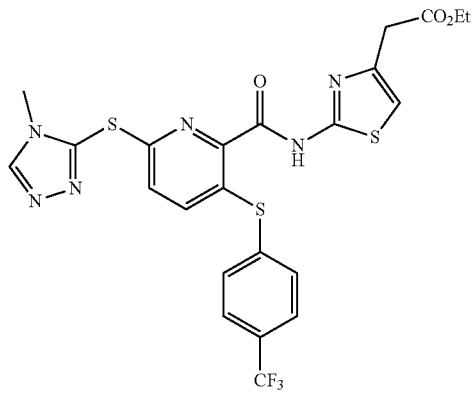 [SMILES: CCOC(=O)Cc1csc(NC(=O)c2nc(Sc3nncn3C)ccc2Sc2ccc(C(F)(F)F)cc2)n1]

In the same manner as in Example 1, the title compound (56 mg, 99%) was obtained as a pale white solid from the amide coupling of 6-[(4-methyl-4H-1,2,4-triazol-3-yl)sulfanyl]-3-{[4-(trifluoromethyl)phenyl]sulfanyl}pyridine-2-carboxylic acid (40.0 mg, 0.097 mmol) and ethyl (2-amino-1,3-thiazol-4-yl)acetate (25.3 mg, 0.136 mmol) and purified by filtration. ESI-MS (m/e): 580.9 [M+H]$^+$.

Example 47

(2-{[(6-[(4-Methyl-4H-1,2,4-triazol-3-yl)sulfanyl]-3-{[4-(trifluoromethyl)phenyl]sulfanyl}pyridin-2-yl)carbonyl]amino}-1,3-thiazol-4-yl)acetic acid

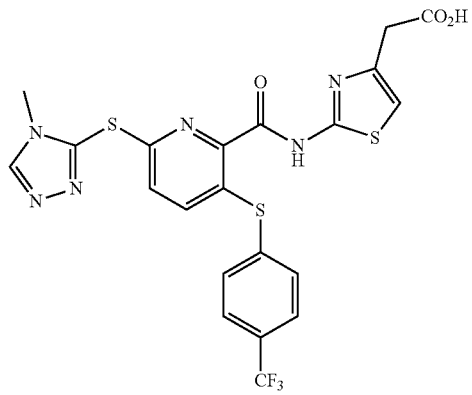 [SMILES: Cn1cnnc1Sc1ccc(Sc2ccc(C(F)(F)F)cc2)c(C(=O)Nc2nc(CC(=O)O)cs2)n1]

In the same manner as in Example 11, the title compound (36.5 mg, 77%) was obtained as a yellow solid from the saponification of ethyl (2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-4-yl)acetate (50 mg, 0.086 mmol) by 0.67 M lithium hydroxide in MeOH/water (1:1:1, 1.5 mL) at rt for 1 h, acidification by 1.5 mL of 1 N HCl and purification by HPLC. ESI-MS (m/e): 552.8 [M+H]$^+$.

Example 48

Methyl 3-(2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)propanoate

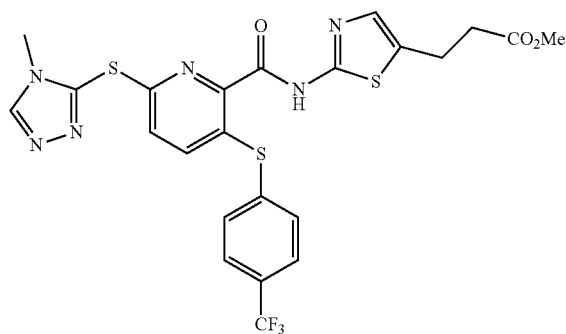 [SMILES: COC(=O)CCc1cnc(NC(=O)c2nc(Sc3nncn3C)ccc2Sc2ccc(C(F)(F)F)cc2)s1]

In the same manner as in Example 1, the title compound (39.4 mg, 70%) was obtained as a pale yellow solid from the amide coupling of 6[(4-methyl-4H-1,2,4-triazol-3-yl)sulfanyl]-3-{[4-(trifluoromethyl)phenyl]sulfanyl}pyridine-2-carboxylic acid (40.0 mg, 0.097 mmol) and 5-(3-methoxy-3-oxopropyl)-1,3-thiazol-2-aminium bromide (36.3 mg, 0.136 mmol) and purified by HPLC. ESI-MS (m/e): 580.9 [M+H]$^+$.

Example 49

3-(2-{[(6-[(4-Methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)propanoic acid

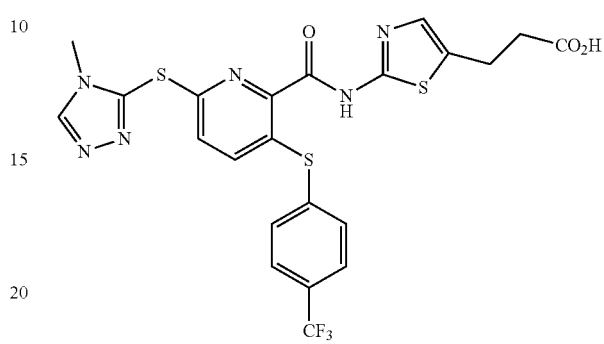

In the same manner as in Example 11, the title compound (22.5 mg, 70%) was obtained as a yellow solid from the saponification of methyl 3-(2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)propanoate (33 mg, 0.057 mmol) by 0.67 M lithium hydroxide in MeOH/water (1:1:1, 1.5 mL) at rt for 1 h, acidification by 1.5 mL of 1 N HCl and purification by HPLC. ESI-MS (m/e): 566.8 [M+H]$^+$.

Example 50

Diethyl ({2-[{3-[(3,4-dichlorophenyl)sulfanyl]-6-[(4-methyl-4H-1,2,4-triazol-3-yl)sulfanyl]pyridin-2-yl}carbonyl)amino]-1,3-thiazol-5-yl}methyl)phosphonate

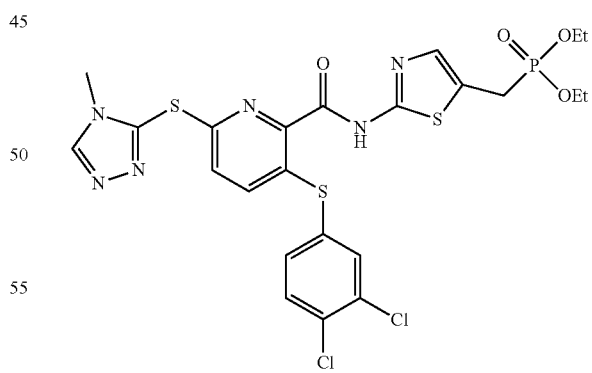

In the same manner as in Example 1, the title compound (59 mg, 94%) was obtained as a yellow solid from the amide coupling of 3-[(3,4-dichlorophenyl)sulfanyl]-6-[(4-methyl-4H-1,2,4-triazol-3-yl)sulfanyl]pyridine-2-carboxylic acid (40.0 mg, 0.097 mmol) and diethyl [(2-amino-1,3-thiazol-5-yl)methyl]phosphonate (26.6 mg, 0.106 mmol) and purified by HPLC. ESI-MS (m/e): 644.9 [M+H]$^+$.

Example 51

Ethyl ({2-[({3-[(3,4-dichlorophenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetate

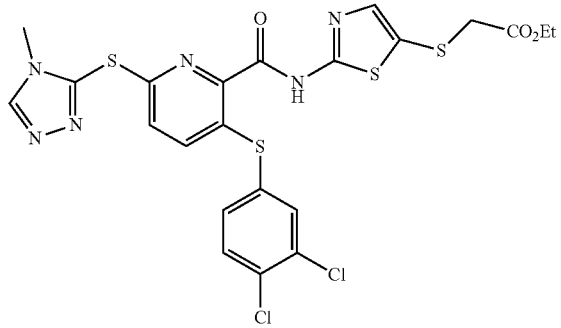 [SMILES: CCOC(=O)CSc1cnc(NC(=O)c2nc(Sc3nncn3C)ccc2Sc2ccc(Cl)c(Cl)c2)s1]

In the same manner as in Example 1, 3-[(3,4-dichlorophenyl)sulfanyl]-6-[(4-methyl-4H-1,2,4-triazol-3-yl)sulfanyl]pyridine-2-carboxylic acid (40.0 mg, 0.097 mmol) and ethyl [(2-amino-1,3-thiazol-5-yl)sulfanyl]acetate (27.5 mg, 0.126 mmol) was coupled in 1 mL of DMF. The reaction mixture was diluted with 2 mL of water and 0.3 mL of TFA to precipitate the desired product. It was filtrated and rinsed with 5 mL of water and 3 mL of acetonitrile. The pale white solid was collected and dried under high vacuum to give the title compound (50.3 mg, 85%). ESI-MS (m/e): 612.9 [M+H]$^+$.

Example 52

({2-[({3-[(3,4-Dichlorophenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetic acid

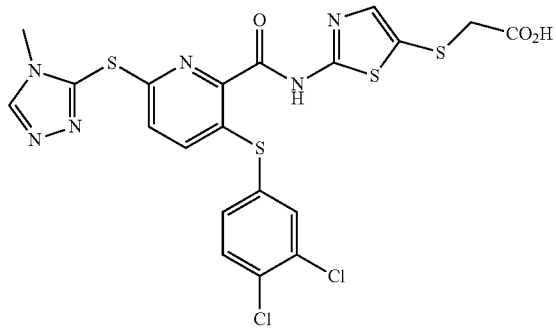 [SMILES: Cn1cnnc1Sc1ccc(Sc2ccc(Cl)c(Cl)c2)c(C(=O)Nc2ncc(SCC(=O)O)s2)n1]

In the same manner as in Example 11, the title compound (22.5 mg, 70%) was obtained as a yellow solid from the saponification of ethyl ({2-[({3-[(3,4-dichlorophenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetate (35 mg, 0.057 mmol) by 0.67 M lithium hydroxide in MeOH/water (1:1:1, 3 mL) at rt for 1 h, acidification by 2.5 mL of 1 N HCl and filtration. ESI-MS (m/e): 584.7 [M+H]$^+$.

Example 53

Ethyl {5-chloro-2-[({3-[(3,4-dichlorophenyl)sulfanyl]-6-[(4-methyl-4H-1,2,4-triazol-3-yl)sulfanyl]pyridin-2-yl}carbonyl)amino]-1,3-thiazol-4-yl}acetate

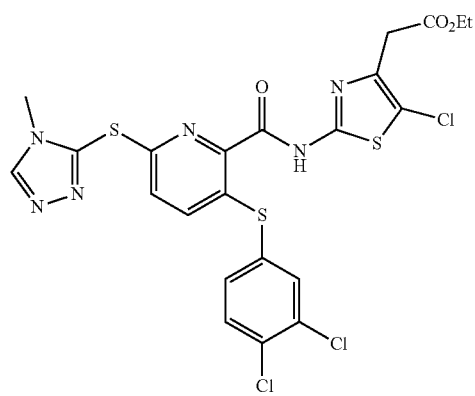 [SMILES: CCOC(=O)Cc1nc(NC(=O)c2nc(Sc3nncn3C)ccc2Sc2ccc(Cl)c(Cl)c2)sc1Cl]

In the same manner as in Example 1, the title compound (45 mg, 75%) was obtained as a yellow solid from the amide coupling of 3-[(3,4-dichlorophenyl)sulfanyl]-6-[(4-methyl-4H-1,2,4-triazol-3-yl)sulfanyl]pyridine-2-carboxylic acid (40.0 mg, 0.097 mmol) and ethyl (2-amino-5-chloro-1,3-thiazol-4-yl)acetate (27.8 mg, 0.126 mmol) and purified by HPLC. ESI-MS (m/e): 614.7 [M+H]$^+$.

Example 54

{5-Chloro-2-[({3-[(3,4-dichlorophenyl)sulfanyl]-6-[(4-methyl-4H-1,2,4-triazol-3-yl)sulfanyl]pyridin-2-yl}carbonyl)amino]-1,3-thiazol-4-yl}acetic acid

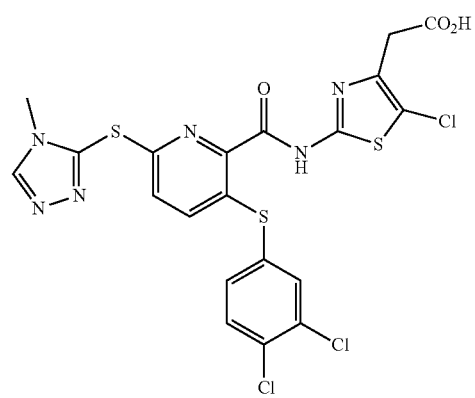 [SMILES: Cn1cnnc1Sc1ccc(Sc2ccc(Cl)c(Cl)c2)c(C(=O)Nc2nc(CC(=O)O)c(Cl)s2)n1]

In the same manner as in Example 11, the title compound (31 mg, 79%) was obtained as a yellow solid from the saponification of ethyl {5-chloro-2-[({3-[(3,4-dichlorophenyl)sulfanyl]-6-[(4-methyl-4H-1,2,4-triazol-3-yl)sulfanyl]pyridin-2-yl}carbonyl)amino]-1,3-thiazol-4-yl}acetate (41 mg, 0.067 mmol) by 0.67 M lithium hydroxide in MeOH/water (1:1:1, 1.5 mL) at rt for 1 h, acidification by 1.5 mL of 1 N HCl and filtration. ESI-MS (m/e): 586.7 [M+H]$^+$.

While the invention has been described and illustrated in reference to specific embodiments thereof, various changes, modifications, and substitutions can be made therein without departing from the invention. For example, alternative effective dosages may be applicable, based upon the responsiveness of the patient being treated. Likewise, the pharmacologic response may vary depending upon the particular active compound selected, formulation and mode of administration. All such variations are included within the present invention.

What is claimed is:

1. A compound of formula I:

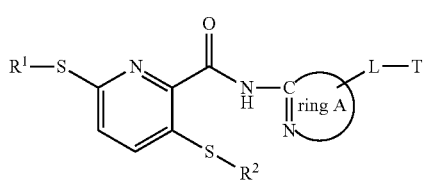

(I)

or a pharmaceutically acceptable salt thereof, wherein:
$R^1$ is triazol, pyridyl or phenyl, optionally substituted with 1-4 substituents independently selected from: halogen, hydroxy, oxo, $C_{1-6}$alkyl, $C_{1-6}$alkylO$C_{1-6}$alkyl, $C_{1-6}$alkoxy, CN, $NR^3R^4$, $C(O)_{1-2}C_{1-6}$alkyl, $C_{1-6}$alkylC(O)$_{1-2}C_{1-6}$alkyl or aryl$C_{1-6}$alkyl, wherein the alkyl and alkoxy substituents are further optionally substituted by 1-4 substituents independently selected from: halogen or $C_{1-6}$alkyl where said $C_{1-6}$alkyl is optionally substituted by 1-6 halogens;
$R^2$ is phenyl, optionally substituted with 1-4 substituents independently selected from: halogen, hydroxy, oxo, $C_{1-6}$alkyl, $C_{1-6}$alkylO$C_{1-6}$alkyl, $C_{1-6}$alkoxy, CN, $NR^3R^4$, $C(O)_{1-2}C_{1-6}$alkyl, $C_{1-6}$alkylC(O)$_{1-2}C_{1-6}$alkyl or aryl$C_{1-6}$alkyl, wherein the alkyl and alkoxy substituents are further optionally substituted by 1-4 substituents independently selected from: halogen or $C_{1-6}$alkyl where said $C_{1-6}$alkyl is optionally substituted by 1-6 halogens;
ring A is thiazolyl which, in addition to the -L-T substituent, is further optionally substituted with 1-4 substituents independently selected from: halogen, hydroxy, $C_{1-6}$alkyl, $C_{1-6}$alkylO$C_{1-6}$alkyl, $C_{1-6}$alkoxy, CN, $NR^3R^4$, $C(O)_{1-2}C_{1-6}$alkyl or $C_{1-6}$alkylC(O)$_{1-2}C_{1-6}$alkyl, wherein the alkyl and alkoxy substituents are further optionally substituted by 1-4 substituents independently selected from: halogen, $C_{1-6}$alkyl or $C_{1-6}$alkoxy where the alkyl and alkoxy substituents are optionally substituted by 1-6 halogens,
L represents $C_{1-6}$alkyl, $C_{1-6}$alkylO$C_{1-6}$alkyl, $C_{1-6}$alkoxy, $NR^3R^4$, $C_{1-6}$alkyl$NR^3R^4$ or $S(O)_{0-2}C_{1-6}$alkyl, wherein the alkyl and alkoxy groups are further optionally substituted by 1-4 substituents independently selected from: halogen or $C_{1-6}$alkyl where said $C_{1-6}$alkyl is optionally substituted by 1-6 halogens,
T represents $CO_2R$, $CONR^3R^4$, or $P(O)(OR^5)_2$,
R is hydrogen, and
$R^3$, $R^4$, and $R^5$ are individually selected from hydrogen or $C_{1-6}$alkyl.

2. The compound of claim 1, wherein $R^1$ is triazolyl, substituted with $C_{1-6}$alkyl optionally substituted by 1-3 halogen; or a pharmaceutically acceptable salt thereof.

3. The compound of claim 1, wherein $R^1$ is pyridyl; or a pharmaceutically acceptable salt thereof.

4. The compound of claim 1, wherein $R^1$ is phenyl, optionally substituted with 1-4 substituents independently selected from: halogen or $C_{1-6}$alkyl, wherein the alkyl is further optionally substituted by 1-6 halogen substituents; or a pharmaceutically acceptable salt thereof.

5. The compound of claim 1, wherein $R^2$ is phenyl, optionally substituted with 1-4 substituents independently selected from: halogen, $C_{1-6}$alkoxy, or $C_{1-6}$alkyl, wherein the alkyl and alkoxy substituents are further optionally substituted by 1-6 halogen substituents; or a pharmaceutically acceptable salt thereof.

6. The compound of claim 1, wherein L represents $C_{1-6}$alkyl or $S(O)_{0-2}C_{1-6}$alkyl, further optionally substituted by 1-6 halogen substituents; or a pharmaceutically acceptable salt thereof.

7. The compound of claim 1, wherein L represents —SCH$_2$—, SC(CH$_3$)$_2$—, —SCH$_2$C(CH$_3$)$_2$—, —CH$_2$CH$_2$— or —CH$_2$—; or a pharmaceutically acceptable salt thereof.

8. A compound which is:
Ethyl ({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetate;
({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetic acid;
3-[(4-methoxyphenyl)sulfanyl]-N-(5-{[2-(methylamino)-2-oxoethyl]sulfanyl}-1,3-thiazol-2-yl)-6-[(4-methyl-4H-1,2,4-triazol-3-yl)sulfanyl]pyridine-2-carboxamide;
2-({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)-2-methylpropanoic acid;
Ethyl 3-({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)-2,2-dimethylpropanoate;
3-({2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}sulfanyl)-2,2-dimethylpropanoic acid;
Methyl 3-{2-[({3-[(4-methoxyphenyl)sulfanyl]-6-[(4-methyl-4H-1,2,4-triazol-3-yl)sulfanyl]pyridin-2-yl}carbonyl)amino]-1,3-thiazol-5-yl}propanoate;
3-{2-[({3-[(4-Methoxyphenyl)sulfanyl]-6-[(4-methyl-4H-1,2,4-triazol-3-yl)sulfanyl]pyridin-2-yl}carbonyl)amino]-1,3-thiazol-5-yl}propanoic acid;
N-[4-(2-Amino-2-oxoethyl)phenyl]-3-[(4-methoxyphenyl)sulfanyl]-6-[(4-methyl-4H-1,2,4-triazol-3-yl)sulfanyl]pyridine-2-carboxamide;
Ethyl ({2-[({3-[(4-methoxyphenyl)sulfanyl]-6-(pyridin-2-ylsulfanyl)pyridin-2-yl}carbonyl)amino]-1,3-thiazol-5-yl}sulfanyl)acetate;
({2-[({3-[(4-Methoxyphenyl)sulfanyl]-6-(pyridin-2-ylsulfanyl)pyridin-2-yl}carbonyl)amino]-1,3-thiazol-5-yl}sulfanyl)acetic acid;
Ethyl {5-chloro-2-[({3-[(4-methoxyphenyl)sulfanyl]-6-(pyridin-2-ylsulfanyl)pyridin-2-yl}carbonyl)amino]-1,3-thiazol-4-yl}acetate;
{5-Chloro-2-[({3-[(4-methoxyphenyl)sulfanyl]-6-(pyridin-2-ylsulfanyl)pyridin-2-yl}carbonyl)amino]-1,3-thiazol-4-yl}acetic acid;
Methyl 3-{2-[({3-[(4-methoxyphenyl)sulfanyl]-6-(pyridin-2-ylsulfanyl)pyridin-2-yl}carbonyl)amino]-1,3-thiazol-5-yl}propanoate;
3-{2-[({3-[(4-Methoxyphenyl)sulfanyl]-6-(pyridin-2-ylsulfanyl)pyridin-2-yl}carbonyl)amino]-1,3-thiazol-5-yl}propanoic acid;

Ethyl {2-[({3-[(4-methoxyphenyl)sulfanyl]-6-(pyridin-2-ylsulfanyl)pyridin-2-yl}carbonyl)amino]-1,3-thiazol-4-yl}acetate;

{2-[({3-[(4-Methoxyphenyl)sulfanyl]-6-(pyridin-2-ylsulfanyl)pyridin-2-yl}carbonyl)amino]-1,3-thiazol-4-yl}acetic acid;

Ethyl ({5-[({3-[(4-fluorophenyl)sulfanyl]-6-[(4-methyl-4H-1,2,4-triazol-3-yl)sulfanyl]pyridin-2-yl}carbonyl)amino]thiophen-2-yl}sulfanyl)acetate;

({2-[({3-[(4-Fluorophenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetic acid;

Ethyl 3-({5-[({3-[(4-fluorophenyl)sulfanyl]-6-[(4-methyl-4H-1,2,4-triazol-3-yl)sulfanyl]pyridin-2-yl}carbonyl)amino]thiophen-2-yl}sulfanyl)-2,2-dimethylpropanoate;

3-({2-[({3-[(4-Fluorophenyl)sulfanyl]-6-[(4-methyl-4H-1,2,4-triazol-3-yl)sulfanyl]pyridin-2-yl}carbonyl)amino]-1,3-thiazol-5-yl}sulfanyl)-2,2-dimethylpropanoic acid;

Ethyl {2-[({3-[(4-fluorophenyl)sulfanyl]-6-[(4-methyl-4H-1,2,4-triazol-3-yl)sulfanyl]pyridin-2-yl}carbonyl)amino]-1,3-thiazol-5-yl}acetate;

{2-[({3-[(4-Fluorophenyl)sulfanyl]-6-[(4-methyl-4H-1,2,4-triazol-3-yl)sulfanyl]pyridin-2-yl}carbonyl)amino]-1,3-thiazol-5-yl}acetic acid;

Ethyl {5-chloro-2-[({3-[(4-fluorophenyl)sulfanyl]-6-[(4-methyl-4H-1,2,4-triazol-3-yl)sulfanyl]pyridin-2-yl}carbonyl)amino]-1,3-thiazol-4-yl}acetate;

{5-Chloro-2-[({3-[(4-fluorophenyl)sulfanyl]-6-[(4-methyl-4H-1,2,4-triazol-3-yl)sulfanyl]pyridin-2-yl}carbonyl)amino]-1,3-thiazol-4-yl}acetic acid;

Diethyl ({2-[({3-[(4-fluorophenyl)sulfanyl]-6-[(4-methyl-4H-1,2,4-triazol-3-yl)sulfanyl]pyridin-2-yl}carbonyl)amino]-1,3-thiazol-5-yl}methyl)phosphonate;

Ethyl ({5-[({3,6-bis[(4-fluorophenyl)sulfanyl]pyridin-2-yl}carbonyl)amino]thiophen-2-yl}sulfanyl)acetate;

({2-[({3,6-Bis[(4-fluorophenyl)sulfanyl]pyridin-2-yl}carbonyl)amino]-1,3-thiazol-5-yl}sulfanyl)acetic acid;

Ethyl {2-[({3,6-bis[(4-fluorophenyl)sulfanyl]pyridin-2-yl}carbonyl)amino]-5-chloro-1,3-thiazol-4-yl}acetate;

{2-[({3,6-Bis[(4-fluorophenyl)sulfanyl]pyridin-2-yl}carbonyl)amino]-5-chloro-1,3-thiazol-4-yl}acetic acid;

Ethyl {5-chloro-2-[({3-[(4-fluorophenyl)sulfanyl]-6-(pyridin-2-ylsulfanyl)pyridin-2-yl}carbonyl)amino]-1,3-thiazol-4-yl}acetate;

{5-Chloro-2-[({3-[(4-fluorophenyl)sulfanyl]-6-(pyridin-2-ylsulfanyl)pyridin-2-yl}carbonyl)amino]-1,3-thiazol-4-yl}acetic acid;

Ethyl {2-[({3-[(4-fluorophenyl)sulfanyl]-6-(pyridin-2-ylsulfanyl)pyridin-2-yl}carbonyl)amino]-1,3-thiazol-4-yl}acetate;

{2-[({3-[(4-Fluorophenyl)sulfanyl]-6-(pyridin-2-ylsulfanyl)pyridin-2-yl}carbonyl)amino]-1,3-thiazol-4-yl}acetic acid;

Ethyl ({2-[({3-[(4-fluorophenyl)sulfanyl]-6-(pyridin-2-ylsulfanyl)pyridin-2-yl}carbonyl)amino]-1,3-thiazol-5-yl}sulfanyl)acetate;

({2-[({3-[(4-Fluorophenyl)sulfanyl]-6-(pyridin-2-ylsulfanyl)pyridin-2-yl}carbonyl)amino]-1,3-thiazol-5-yl}sulfanyl)acetic acid;

Ethyl 3-({2-[({3-[(4-fluorophenyl)sulfanyl]-6-(pyridin-2-ylsulfanyl)pyridin-2-yl}carbonyl)amino]-1,3-thiazol-5-yl}sulfanyl)-2,2-dimethylpropanoate;

3-({2-[({3-[(4-Fluorophenyl)sulfanyl]-6-(pyridin-2-ylsulfanyl)pyridin-2-yl}carbonyl)amino]-1,3-thiazol-5-yl}sulfanyl)-2,2-dimethylpropanoic acid;

Methyl 3-{2-[({3-[(4-fluorophenyl)sulfanyl]-6-(pyridin-2-ylsulfanyl)pyridin-2-yl}carbonyl)amino]-1,3-thiazol-5-yl}propanoate;

3-{2-[({3-[(4-Fluorophenyl)sulfanyl]-6-(pyridin-2-ylsulfanyl)pyridin-2-yl}carbonyl)amino]-1,3-thiazol-5-yl}propanoic acid;

Ethyl (5-chloro-2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-4-yl)acetate;

(5-Chloro-2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-4-yl)acetic acid;

Ethyl [(2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)sulfanyl]acetate;

[(2-{[(6-[(4-Methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)sulfanyl]acetic acid;

Diethyl [(2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)methyl]phosphonate;

Ethyl (2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-4-yl)acetate;

(2-{[(6-[(4-Methyl-4H-1,2,4-triazol-3-yl)sulfanyl]-3-{[4-(trifluoromethyl)phenyl]sulfanyl}pyridin-2-yl)carbonyl]amino}-1,3-thiazol-4-yl)acetic acid;

Methyl 3-(2-{[(6-[(4-methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)propanoate;

3-(2-{[(6-[(4-Methyl-4H-1,2,4-triazol-3-yl)sulfanyl]-3-{[4-(trifluoromethyl)phenyl]sulfanyl}pyridin-2-yl)carbonyl]amino}-1,3-thiazol-5-yl)propanoic acid;

Diethyl ({2-[({3-[(3,4-dichlorophenyl)sulfanyl]-6-[(4-methyl-4H-1,2,4-triazol-3-yl)sulfanyl]pyridin-2-yl}carbonyl)amino]-1,3-thiazol-5-yl}methyl)phosphonate;

Ethyl ({2-[({3-[(3,4-dichlorophenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetate;

({2-[({3-[(3,4-Dichlorophenyl)sulfanyl]-6-[(4-methyl-4H-1,2,4-triazol-3-yl)sulfanyl]pyridin-2-yl}carbonyl)amino]-1,3-thiazol-5-yl}sulfanyl)acetic acid;

Ethyl {5-chloro-2-[({3-[(3,4-dichlorophenyl)sulfanyl]-6-[(4-methyl-4H-1,2,4-triazol-3-yl)sulfanyl]pyridin-2-yl}carbonyl)amino]-1,3-thiazol-4-yl}acetate;

{5-Chloro-2-[({3-[(3,4-dichlorophenyl)sulfanyl]-6-[(4-methyl-4H-1,2,4-triazol-3-yl)sulfanyl]pyridin-2-yl}carbonyl)amino]-1,3-thiazol-4-yl}acetic acid; or a pharmaceutically acceptable salt thereof.

9. A pharmaceutical composition comprising the compound of claim 1, and a pharmaceutically acceptable carrier.

10. A method for the treatment of a condition selected from obesity or diabetes comprising administering to an individual a pharmaceutical composition comprising the compound or pharmaceutically acceptable salt of claim 1.

11. The method of claim 10 where the compound or pharmaceutically acceptable salt of claim 1 is used in combination with one or more other active ingredients.

12. A method for the treatment of a condition selected from obesity or diabetes comprising administering to an individual a pharmaceutical composition comprising the compound or pharmaceutically acceptable salt of claim 8.

13. The method of claim 12 where the compound or pharmaceutically acceptable salt of claim 12 is used in combination with one or more other active ingredients.

* * * * *